(12) United States Patent
Adam et al.

(10) Patent No.: US 8,507,521 B2
(45) Date of Patent: Aug. 13, 2013

(54) HETEROCYCLIC DERIVATIVES

(75) Inventors: Julia Adam, Lanarkshire (GB);
Jonathan Gillespie, Wishaw (GB);
Steven Laats, Lanarkshire (GB); John Kinnaird Ferguson MacLean, Brookline, MA (US); Duncan Robert McArthur, Lanarkshire (GB)

(73) Assignee: Merck Sharp + Dohme B.V. (NL)

( * ) Notice: Subject to any disclaimer, the term of this patent is extended or adjusted under 35 U.S.C. 154(b) by 0 days.

(21) Appl. No.: 13/505,349

(22) PCT Filed: Nov. 2, 2010

(86) PCT No.: PCT/EP2010/066584
§ 371 (c)(1),
(2), (4) Date: May 1, 2012

(87) PCT Pub. No.: WO2011/051490
PCT Pub. Date: May 5, 2011

(65) Prior Publication Data
US 2012/0220622 A1    Aug. 30, 2012

Related U.S. Application Data

(60) Provisional application No. 61/257,197, filed on Nov. 2, 2009.

(30) Foreign Application Priority Data

Nov. 2, 2009  (EP) ..................... 09174808

(51) Int. Cl.
*A61K 31/437* (2006.01)
*A61K 31/4439* (2006.01)
*A61K 31/422* (2006.01)
*A61K 31/4178* (2006.01)
*C07D 471/04* (2006.01)
*A61P 25/22* (2006.01)
*C07D 401/14* (2006.01)
*C07D 413/10* (2006.01)
*C07D 403/10* (2006.01)
*C07D 405/14* (2006.01)
*A61P 25/18* (2006.01)
*A61K 31/4725* (2006.01)
*C07D 401/10* (2006.01)

(52) U.S. Cl.
USPC ........... 514/300; 514/309; 514/339; 514/376; 514/397; 546/113; 546/141; 546/274.4; 548/229; 548/312.1

(58) Field of Classification Search
None
See application file for complete search history.

(56) References Cited

U.S. PATENT DOCUMENTS 7,868,008 B2 *   1/2011   Van Wagenen et al. . 514/254.09

FOREIGN PATENT DOCUMENTS

| WO | 2007/021309 A1 | 2/2007 |
| WO | 2007/095024 A1 | 8/2007 |
| WO | 2009/004430 A1 | 1/2009 |
| WO | 2011/051490 A3 | 5/2011 |

OTHER PUBLICATIONS

WO2011/051490 Search Report, (Apr. 28, 2011).

* cited by examiner

*Primary Examiner* — Michael Barker
*Assistant Examiner* — Po-Chih Chen
(74) *Attorney, Agent, or Firm* — Susan L. Hess; Gerard M. Devlin

(57) ABSTRACT

The present invention relates to a heterocyclic derivative of formula (I) wherein the variables are as defined in the specification, or to a pharmaceutically acceptable salt or solvate thereof. The present invention further relates to pharmaceutical compositions comprising said heterocyclic derivatives and to their use in therapy, for instance in the treatment or prevention of disorders mediated by glutamate dysfunction, such as schizophrenia and generalised anxiety disorder.

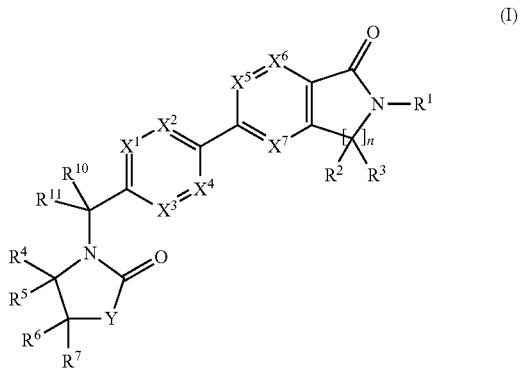

(I)

12 Claims, No Drawings

HETEROCYCLIC DERIVATIVES

CROSS REFERENCE TO RELATED APPLICATIONS

This application is a U.S. National Phase application under 35 U.S.C. §371 of PCT Application No. PCT/EP2010/066584, filed Nov. 2, 2010 which claims priority under 35 U.S.C. §119 from U.S. Provisional Application Ser. Nos. 61/257,197, filed Nov. 2, 2009 and EP09174808.7, filed Nov. 2, 2009.

The present invention relates to heterocyclic derivatives, to pharmaceutical compositions comprising these compounds and to their use in therapy, in particular to their use in the treatment or prevention of diseases or disorders mediated by glutamate dysfunction, such as schizophrenia or generalised anxiety disorder.

Glutamate is the major mediator of excitatory signalling in the mammalian central nervous system (CNS) and plays a role in a wide variety of processes such as learning, plasticity and cognition. Glutamate also plays a pivotal role in CNS development processes including synapse formation and elimination, cell migration, cell differentiation and cell death [Sahai, European Archives of Psychiatry and Clinical Neuroscience 240, 121, (1990)].

Glutamate acts via at least two distinct classes of receptors; ionotropic glutamate receptors (iGluRs), which are glutamate mediated ion channels, and metabotropic glutamate receptors (mGluRs), which are class C G-protein coupled receptors (GPCRs) [Kew and Kemp, Psychopharmacology 179, 4, (2005)]. Activation of the iGluRs mediates fast neuronal transmission at the synapse, whereas mGluRs function as pre- or post-synaptic regulatory mechanisms to control the release of neurotransmitters or modulate neuronal excitability [Niswender et al., Current Topics in Medicinal Chemistry 5, 847, (2005)].

The present invention relates to modulators of mGluRs, in particular mGluR2 receptor positive allosteric modulators (mGluR2 PAMs). At present, eight distinct mGluRs have been identified cloned and their sequences reported. These eight different mGluRs are subdivided into three groups according to their homology, pharmacology [Recasens et al., Current Drug Targets 8, 651, (2007)] and G-protein coupling [Gerber et al., Current Opinion in Pharmacology 7, 56, (2007)]. Group II mGluRs, which include mGluR2 and mGluR3, are located mainly on the presynaptic terminal of neurons in the mammalian CNS [Cartmell and Schoepp, J. Neurochem. 75, 889 (2000)]. mGluR2 and mGluR3 are known to couple to Gi proteins and inhibit cAMP production, thereby modulating synaptic transmission and neurotransmitter release and hence affecting neuronal activity of postsynaptic cells [Anwyl, Brain Research Reviews 29, 83 (1999)]. These receptors can be activated by group II selective mGluR agonists such as 1S,2S,5R,6S-2 aminobicyclo[3.1.0] hexane-2,6-dicarboxylate [Ly354740; Monn et al., J. Med. Chem. 40, 528, (1997)].

As a result of their ability to reduce glutamate release in the synapse and subsequent iGluR activation and neuronal stimulation in brain areas such as the cortex, thalamus, striatum, amygdala and hippocampus, which have been associated with the pathogenesis of psychosis and anxiety [Walker and Davis, Pharmacology, Biochemistry and Behavior 71, 379, (2002)], agonists of group II mGluRs have been linked to the treatment of schizophrenia [Chavez-Noriega et al., Current Neuropharmacology 3, 9, (2005); Conn, Lindsley and Jones, Trends in Pharmacological Sciences 30 25, (2009)] and anxiety related disorders [Chojnacka-Wojcik et al., Current Opinion in Investigational Drugs 2, 1112, (2001); Marino and Conn, Current Opinion in Pharmacology 6, 98, (2006)]. Furthermore, a large body of pre-clinical and clinical studies support targeting group II mGluRs to provide novel treatment strategies for CNS disorders including anxiety and schizophrenia [Moghaddam and Adams, Science 281, 1349, (1998); Schoepp et al., Stress 6, 189, (2003); Swanson et al., Nature Reviews Drug Discovery 4, 131, (2005); Imre, CNS drug reviews 4, 444, (2007); Patil et al., Nature Medicine 13, 1102, 2007; Dunayevich et al., Neuropsychopharmacology 33, 1603, (2008)].

Recent pre-clinical data suggest that mGluR2, not mGluR3, is most likely to underlie the therapeutic effects of mGluR2/3 orthosteric agonists such as Ly354740, Ly379268 and Ly404039 in mouse models predictive of antipsychotic activity [Spooren et al., Eur. J. Pharmacol. 397, R1-R2, (2000); Woolley et al., Psychopharmacology 196, 431, (2008); Fell et al., JPET 326, 209, (2008)]. Additionally, recent studies demonstrated that mGluR2-selective PAMs, structurally distinct from the mGluR2/3 orthosteric agonists, exhibit efficacy similar to that observed for mGluR2/3 orthosteric agonists in animal models that predict for antipsychotic or anxiolytic activity [Galici et al., JPET 315, 1181, (2005); Galici et al., JPET 318, 173, (2006)].

Positive allosteric modulators do not bind at the highly conserved glutamate binding site, termed the orthosteric site, but to an alternative site on the receptor, termed the allosteric site. Through interaction with the allosteric site, PAMs modulate the affinity of the endogenous ligand [Christopoulos, Nature Reviews Drug Discovery 1, 198, (2002)]. A potential advantage to this approach is the opportunity to have a distinct pharmacological profile by enhancing the activity of the endogenous ligand upon its binding to the orthosteric site, rather than continuously activating the receptor with an exogenous agonist. In addition, mGluR2 PAMs may show pharmacological specificity over related receptor types that share the same endogenous ligand, something that has proved difficult with orthosteric agonists [Johnson et al., Biochemical Society Transactions 32, 881, (2004)]. Furthermore, mGluR2 PAMs are suggested to offer an advantage relative to mGluR2/3 orthosteric agonists by preserving the activity dependence of glutamate physiological functions and by reducing receptor desensitization. These properties have led to the hypothesis that mGluR2 PAMs will exhibit reduced side-effect potential compared to mGluR2/3 orthosteric agonists [Marino and Conn, Current Opinion in Pharmacology 6, 98, (2006)].

A number of mGluR2 selective PAMs have been reported in the literature [for a recent review see Fraley, Expert Opin. Ther. Patents 19, 1259, (2009)]. Astra-Zeneca and NPS Pharma have reported isoindolinone derivatives as mGluR2 potentiators useful for treating neurological and psychiatric disorders (WO2007021309; WO2007095024). Despite the availability of these compounds, there remains a need for further mGluR2 selective PAMs which are both safe and effective for use as therapeutic agents.

In a first aspect, the present invention provides heterocyclic derivatives having the general Formula I

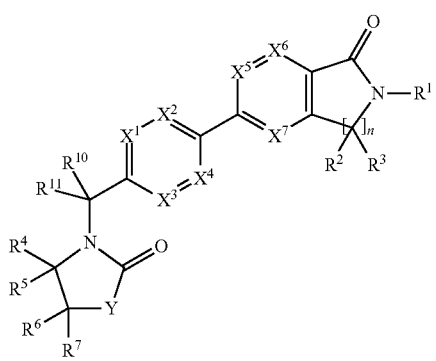

Formula I wherein
R[1] is $C_{1-4}$alkyl, $C_{3-8}$cycloalkyl$C_{0-4}$alkyl, or $Z^1C_0$alkyl, said $C_{1-4}$alkyl and $C_{3-8}$cycloalkyl$C_{0-4}$alkyl being optionally substituted with one or more substituent independently selected from hydroxy, $C_{1-4}$alkyl, $C_{1-4}$alkyloxy, CN and halogen;
$Z^1$ is a 4-7 membered saturated ring containing a heteroatom selected from O, S and $SO_2$;
n is 1 or 2;
each R[2] and R[3] is independently H or $C_{1-4}$alkyl;
Y is O or NR[8];
R[4], R[5], R[6] and R[7] are independently H or $C_{1-4}$alkyl; or when Y is NR[8], either R[4] and R[5], or R[6] and R[7], may together represent oxo;
R[8] is H, $C_{1-4}$alkyl, $C_{3-8}$cycloalkyl$C_{0-4}$alkyl, or $Z^2C_{0-4}$alkyl, said $C_{1-4}$alkyl and $C_{3-8}$cycloalkyl$C_{0-4}$alkyl being optionally substituted with one or more substituent independently selected from hydroxy, $C_{1-4}$alkyl, $C_{1-4}$alkyloxy, oxo, CN and halogen;
$Z^2$ is a 4-7 membered saturated ring containing a heteroatom selected from O, S and $SO_2$;
$X^1$-$X^7$ are CR[9]; or one of $X^1$-$X^7$ may be N;
each R[9] is independently selected from H, $C_{1-4}$alkyl, $C_{1-4}$alkyloxy, $C_{1-4}$alkylsulfonyl, nitrile and halogen, said $C_{1-4}$alkyl and $C_{1-4}$alkyloxy groups being optionally substituted with one or more substituent independently selected from hydroxy and halogen;
R[10] and R[11] are independently H or $C_{1-4}$alkyl; or, when R[10] is alkyl and $X^1$ is CR[9], R[10] and R[9] together with the atoms to which they are bonded may form a fused ring optionally comprising a heteroatomic moiety selected from O, S and $SO_2$;
or a pharmaceutically acceptable salt or solvate thereof.

The term $C_{1-4}$alkyl, as used herein, represents a branched or unbranched alkyl group having 1-4 carbon atoms. Examples of such groups are methyl, ethyl, isopropyl, tertiary butyl and isobutyl.

The term $C_{3-8}$cycloalkyl, as used herein, represents a cyclic alkyl group having 3-8 carbon atoms. Examples of such groups are cyclopropyl, cyclobutyl, cyclopentyl and cyclohexyl.

The term $C_{3-8}$cycloalkyl$C_{0-4}$alkyl, as used herein, represents a $C_{0-4}$alkyl group which is substituted with a $C_{3-8}$cycloalkyl. Examples of such groups are cyclopropyl, cyclopentyl, cyclohexyl, cyclopropylmethyl and 2-cyclobutylethyl. It will be appreciated by the skilled person that $C_{3-8}$cycloalkyl$C_0$alkyl is $C_{3-8}$cycloalkyl.

The terms $Z^1C_{0-4}$alkyl and $Z^2C_{0-4}$alkyl, as used herein, represent $C_{0-4}$alkyl groups which are substituted with $Z^1$ and $Z^2$ respectively. Examples of such groups are oxetan-3-yl, tetrahydrofuran-3-yl and tetrahydropyran-4-ylmethyl. It will be appreciated by the skilled person that $Z^1C_0$alkyl is $Z^1$ and $Z^2C_0$alkyl is $Z^2$.

The term $C_{1-4}$alkyloxy, as used herein, represents a branched or unbranched alkyloxy group having 1-4 carbon atoms. Examples of such groups are methoxy, ethoxy, isopropyloxy and tertiary butyloxy.

The term halogen, as used herein, represents a fluorine, chlorine, bromine or iodine.

In the definition of Formula I, when Y is NR[8], either R[4] and R[5], or R[6] and R[7], may together represent oxo. It will be appreciated by the skilled person that when R[4] and R[5] together represent oxo, R[4] and R[5] together with the carbon atom to which they are bonded form a carbonyl. Likewise when R[6] and R[7] together represent oxo, R[6] and R[7] together with the carbon atom to which they are bonded form a carbonyl.

In the definition of Formula I, when R[10] is alkyl and $X^1$ is CR[9], R[10] and R[9] together with the atoms to which they are bonded may form a fused ring optionally comprising a heteroatomic moiety selected from O, S and $SO_2$. Examples of the fused bicyclic systems thus formed include chroman, isochroman, 1,2,3,4-tetrahydronaphthalene, 2,3-dihydro-1H-indene and 2,3-dihydrobenzofuran.

In the definition of Formula I, $Z^1$ and $Z^2$, when present, are 4-7 membered saturated rings containing a heteroatom selected from O, S and $SO_2$. Examples of such rings include oxetane, tetrahydrofuran, tetrahydropyran and tetrahydrothiopyran.

The term solvate, as used herein, refers to a complex of variable stoichiometry formed by a solvent and a solute (in this invention, a compound of formula I). Such solvents may not interfere with the biological activity of the solute. Examples of suitable solvents include water and ethanol.

In one embodiment of the present invention, R[1] is $C_{1-4}$alkyl or $C_{3-8}$cycloalkyl.

In another embodiment of the present invention, n is 1.

In another embodiment of the present invention, R[2] and R[3] are H.

In another embodiment of the present invention, R[4] and R[5] are independently H or $C_{1-4}$alkyl.

In a further embodiment of the present invention, Y is NR[8] and R[6] and R[7] together represent oxo, i.e. the fragment

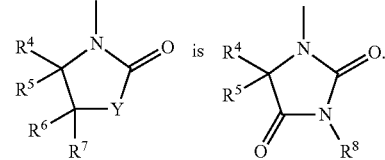

In another embodiment of the present invention, R[8] is $C_{1-4}$alkyl or $C_{3-8}$cycloalkyl.

In another embodiment of the present invention, $X^1$-$X^7$ are CR[9] and each R[9] is independently selected from H, $C_{1-4}$alkyl, $C_{1-4}$alkyloxy, nitrile or halogen, said $C_{1-4}$alkyl or $C_{1-4}$alkyloxy groups being optionally substituted with one or more halogen.

In another embodiment of the present invention, R[10] and R[11] are H.

In another embodiment of the present invention is a compound selected from:
1-(4-(2-cyclopropyl-1-oxoisoindolin-5-yl)benzyl)-3-methylimidazolidine-2,4-dione;

1-(2-chloro-4-(2-cyclopropyl-1-oxoisoindolin-5-yl)benzyl)-3-ethylimidazolidine-2,4-dione;

1-(4-(2-cyclopropyl-1-oxoisoindolin-5-yl)benzyl)-3-ethyl-5,5-dimethylimidazolidine-2,4-dione;

1-(4-(7-chloro-2-(3-hydroxy-2,2-dimethylpropyl)-1-oxoisoindolin-5-yl)benzyl)-3-ethylimidazolidine-2,4-dione;

3-ethyl-1-(4-(1-oxo-2-(2,2,2-trifluoroethyl)isoindolin-5-yl)benzyl)imidazolidine-2,4-dione;

3-(4-(2-cyclopropyl-1-oxoisoindolin-5-yl)benzyl)-1-methylimidazolidine-2,4-dione;

2-cyclopropyl-5-(4-((3-methyl-2-oxoimidazolidin-1-yl)methyl)phenyl)isoindolin-1-one;

1-(2-chloro-4-(2-cyclopropyl-1-oxoisoindolin-5-yl)benzyl)-3-methylimidazolidine-2,4-dione;

1-(2-chloro-4-(1-oxo-2-(2,2,2-trifluoroethyl)isoindolin-5-yl)benzyl)-3-methylimidazolidine-2,4-dione;

1-(2-chloro-4-(2-(3-hydroxy-2,2-dimethylpropyl)-1-oxoisoindolin-5-yl)benzyl)-3-methylimidazolidine-2,4-dione;

1-(2-chloro-4-(2-cyclopropyl-1-oxoisoindolin-5-yl)benzyl)-3,5,5-trimethylimidazolidine-2,4-dione;

1-(2-chloro-4-(1-oxo-2-(2,2,2-trifluoroethyl)isoindolin-5-yl)benzyl)-3,5,5-trimethylimidazolidine-2,4-dione;

1-(3-chloro-4-(2-cyclopropyl-1-oxoisoindolin-5-yl)benzyl)-3-methylimidazolidine-2,4-dione;

1-(3-chloro-4-(2-(3-hydroxy-2,2-dimethylpropyl)-1-oxoisoindolin-5-yl)benzyl)-3-methylimidazolidine-2,4-dione;

3,5,5-trimethyl-1-(4-(1-oxo-2-(2,2,2-trifluoroethyl)isoindolin-5-yl)benzyl)imidazolidine-2,4-dione;

1-(3-chloro-4-(2-cyclopropyl-1-oxoisoindolin-5-yl)benzyl)-3,5,5-trimethylimidazolidine-2,4-dione;

1-(3-chloro-4-(1-oxo-2-(2,2,2-trifluoroethyl)isoindolin-5-yl)benzyl)-3,5,5-trimethylimidazolidine-2,4-dione;

1-(4-(2-(3-hydroxy-2,2-dimethylpropyl)-1-oxoisoindolin-5-yl)benzyl)-3,5,5-trimethylimidazolidine-2,4-dione;

1-(4-(2-isopropyl-1-oxoisoindolin-5-yl)benzyl)-3-methylimidazolidine-2,4-dione;

1-(4-(2-cyclobutyl-1-oxoisoindolin-5-yl)benzyl)-3,5,5-trimethylimidazolidine-2,4-dione;

1-(4-(2-isobutyl-1-oxoisoindolin-5-yl)benzyl)-3,5,5-trimethylimidazolidine-2,4-dione;

1-(4-(2-cyclopropyl-1-oxoisoindolin-5-yl)benzyl)-3-ethylimidazolidine-2,4-dione;

3-methyl-1-(4-(1-oxo-2-(2,2,2-trifluoroethyl)isoindolin-5-yl)benzyl)imidazolidine-2,4-dione;

1-(4-(7-chloro-1-oxo-2-(2,2,2-trifluoroethyl)isoindolin-5-yl)benzyl)-3-methylimidazolidine-2,4-dione;

1-(4-(7-chloro-2-cyclopropyl-1-oxoisoindolin-5-yl)benzyl)-3-methylimidazolidine-2,4-dione;

3-ethyl-1-(4-(2-methyl-1-oxoisoindolin-5-yl)benzyl)imidazolidine-2,4-dione;

3-ethyl-1-(4-(2-isopropyl-1-oxoisoindolin-5-yl)benzyl)imidazolidine-2,4-dione;

3-ethyl-5,5-dimethyl-1-(4-(2-methyl-1-oxoisoindolin-5-yl)benzyl)imidazolidine-2,4-dione;

3-ethyl-1-(4-(2-ethyl-1-oxoisoindolin-5-yl)benzyl)-5,5-dimethylimidazolidine-2,4-dione;

3-ethyl-5,5-dimethyl-1-(4-(1-oxo-2-propylisoindolin-5-yl)benzyl)imidazolidine-2,4-dione;

3-ethyl-1-(4-(2-isopropyl-1-oxoisoindolin-5-yl)benzyl)-5,5-dimethylimidazolidine-2,4-dione;

1-(4-(2-ethyl-1-oxoisoindolin-5-yl)benzyl)-3-methylimidazolidine-2,4-dione;

3-methyl-1-(4-(1-oxo-2-propylisoindolin-5-yl)benzyl)imidazolidine-2,4-dione;

3-ethyl-1-(4-(2-ethyl-1-oxoisoindolin-5-yl)benzyl)imidazolidine-2,4-dione;

3-ethyl-1-(4-(1-oxo-2-propylisoindolin-5-yl)benzyl)imidazolidine-2,4-dione;

1-(4-(2-cyclobutyl-1-oxoisoindolin-5-yl)benzyl)-3-ethylimidazolidine-2,4-dione;

1-(4-(2-cyclobutyl-1-oxoisoindolin-5-yl)benzyl)-3-methylimidazolidine-2,4-dione;

1-(4-(2-isobutyl-1-oxoisoindolin-5-yl)benzyl)-3-methylimidazolidine-2,4-dione;

1-(4-(2-(cyclopropylmethyl)-1-oxoisoindolin-5-yl)benzyl)-3-ethylimidazolidine-2,4-dione;

1-(4-(2-(cyclopropylmethyl)-1-oxoisoindolin-5-yl)benzyl)-3-ethyl-5,5-dimethylimidazolidine-2,4-dione;

1-(4-(2-(cyclopropylmethyl)-1-oxoisoindolin-5-yl)benzyl)-3-methylimidazolidine-2,4-dione;

3,5,5-trimethyl-1-(4-(2-methyl-1-oxoisoindolin-5-yl)benzyl)imidazolidine-2,4-dione;

1-(4-(2-ethyl-1-oxoisoindolin-5-yl)benzyl)-3,5,5-trimethylimidazolidine-2,4-dione;

3,5,5-trimethyl-1-(4-(1-oxo-2-propylisoindolin-5-yl)benzyl)imidazolidine-2,4-dione;

1-(4-(2-isopropyl-1-oxoisoindolin-5-yl)benzyl)-3,5,5-trimethylimidazolidine-2,4-dione;

1-(4-(2-(cyclopropylmethyl)-1-oxoisoindolin-5-yl)benzyl)-3,5,5-trimethylimidazolidine-2,4-dione;

3,5,5-trimethyl-1-(4-(1-oxo-2-propyl-1,2,3,4-tetrahydroisoquinolin-6-yl)benzyl)imidazolidine-2,4-dione;

1-(4-(2-isopropyl-1-oxo-1,2,3,4-tetrahydroisoquinolin-6-yl)benzyl)-3,5,5-trimethylimidazolidine-2,4-dione;

(R)-3-(4-(2-cyclopropyl-1-oxoisoindolin-5-yl)benzyl)-5-methyloxazolidin-2-one;

(R)-3-(4-(2-(3-hydroxy-2,2-dimethylpropyl)-1-oxoisoindolin-5-yl)benzyl)-5-methyloxazolidin-2-one;

(R)-1-(1-(4-(2-cyclopropyl-1-oxoisoindolin-5-yl)phenyl)ethyl)-3-ethylimidazolidine-2,4-dione;

(R)-3-ethyl-1-(1-(4-(1-oxo-2-(2,2,2-trifluoroethyl)isoindolin-5-yl)phenyl)ethyl)imidazolidine-2,4-dione;

1-(5-(2-cyclopropyl-1-oxoisoindolin-5-yl)-2,3-dihydro-1H-inden-1-yl)-3-ethylimidazolidine-2,4-dione;

3-ethyl-1-(5-(1-oxo-2-(2,2,2-trifluoroethyl)isoindolin-5-yl)-2,3-dihydro-1H-inden-1-yl)imidazolidine-2,4-dione;

3-cyclopropyl-1-(4-(2-cyclopropyl-1-oxoisoindolin-5-yl)benzyl)imidazolidine-2,4-dione;

3-cyclopropyl-1-(4-(2-(3-hydroxy-2,2-dimethylpropyl)-1-oxoisoindolin-5-yl)benzyl)imidazolidine-2,4-dione;

3-cyclopropyl-1-(4-(1-oxo-2-(2,2,2-trifluoroethyl)isoindolin-5-yl)benzyl)imidazolidine-2,4-dione;

1-(4-(2-cyclopropyl-1-oxoisoindolin-5-yl)benzyl)-3,5,5-trimethylimidazolidine-2,4-dione;

1-((5-(2-cyclopropyl-1-oxoisoindolin-5-yl)pyridin-2-yl)methyl)-3-methylimidazolidine-2,4-dione;

1-((5-(2-cyclopropyl-1-oxoisoindolin-5-yl)pyridin-2-yl)methyl)-3-isobutylimidazolidine-2,4-dione;

1-((6-(2-cyclopropyl-1-oxoisoindolin-5-yl)pyridin-3-yl)methyl)-3-methylimidazolidine-2,4-dione;

3-methyl-1-((6-(1-oxo-2-(2,2,2-trifluoroethyl)isoindolin-5-yl)pyridin-3-yl)methyl)imidazolidine-2,4-dione;

1-(4-(7-chloro-2-isopropyl-1-oxoisoindolin-5-yl)benzyl)-3-methylimidazolidine-2,4-dione;

1-(2-chloro-4-(7-chloro-2-cyclopropyl-1-oxoisoindolin-5-yl)benzyl)-3-methylimidazolidine-2,4-dione;

1-(3-chloro-4-(7-chloro-2-cyclopropyl-1-oxoisoindolin-5-yl)benzyl)-3-methylimidazolidine-2,4-dione;

(S)-1-(4-(7-chloro-1-oxo-2-(1,1,1-trifluoropropan-2-yl)isoindolin-5-yl)benzyl)-3-methylimidazolidine-2,4-dione;

(S)-1-(4-(7-chloro-2-(1-cyclopropylethyl)-1-oxoisoindolin-5-yl)benzyl)-3-methylimidazolidine-2,4-dione;

1-(3-chloro-4-(7-chloro-2-isopropyl-1-oxoisoindolin-5-yl)benzyl)-3-methylimidazolidine-2,4-dione;

1-(2-chloro-4-(7-chloro-2-isopropyl-1-oxoisoindolin-5-yl)benzyl)-3-methylimidazolidine-2,4-dione;

1-(4-(7-chloro-2-isopropyl-1-oxoisoindolin-5-yl)-3-fluorobenzyl)-3-methylimidazolidine-2,4-dione;

(S)-1-(4-(7-chloro-2-(1-cyclopropylethyl)-1-oxoisoindolin-5-yl)-3-fluorobenzyl)-3-methylimidazolidine-2,4-dione;

3-(4-(2-cyclopropyl-1-oxoisoindolin-5-yl)benzyl)-5,5-dimethyloxazolidin-2-one;

2-isopropyl-6-(4-((3-methyl-2,4-dioxoimidazolidin-1-yl)methyl)phenyl)-3-oxoisoindoline-4-carbonitrile;

or a pharmaceutically acceptable salt or solvate thereof.

The heterocyclic derivatives of the present invention are prepared by methods well known in the art of organic chemistry. See, for example, J. March, 'Advanced Organic Chemistry' 4th Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts '*Protective Groups in Organic Synthesis*' 2<sup>nd</sup> Edition, John Wiley and Sons, 1991. The protective groups are optionally removed at a convenient subsequent stage using methods well known in the art.

General Schemes

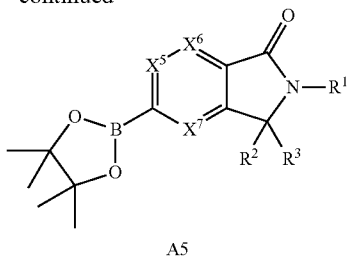

A5

Benzoic acid derivatives such as (A1) can be esterified and subsequently halogenated to give a benzyl halide derivative (A2). Displacement of the halogen with an amine (A3) and ring closure at elevated temperature gives the iso-indolinone derivative (A4). (A4) is either used as the aryl halide or further functionalised to the boronic ester intermediate (A5) via palladium mediated coupling.

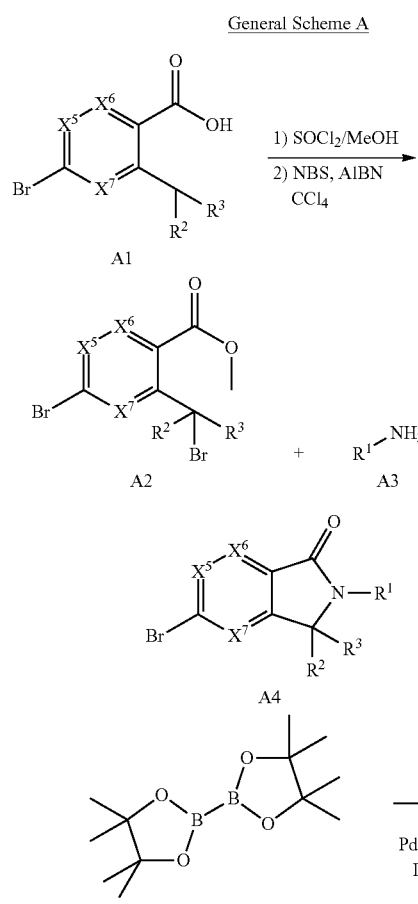

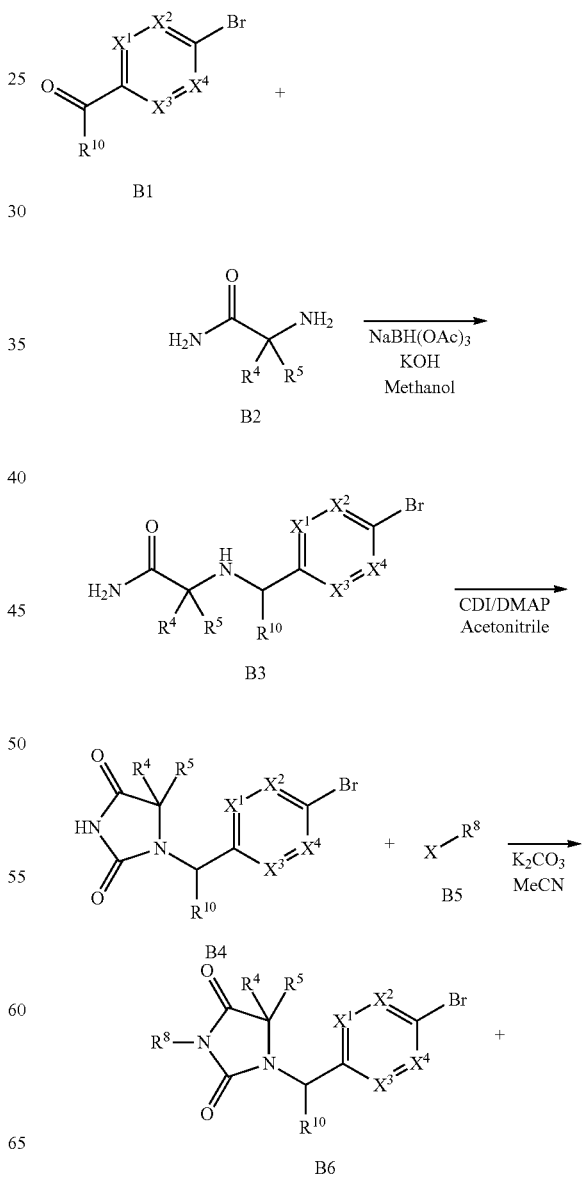

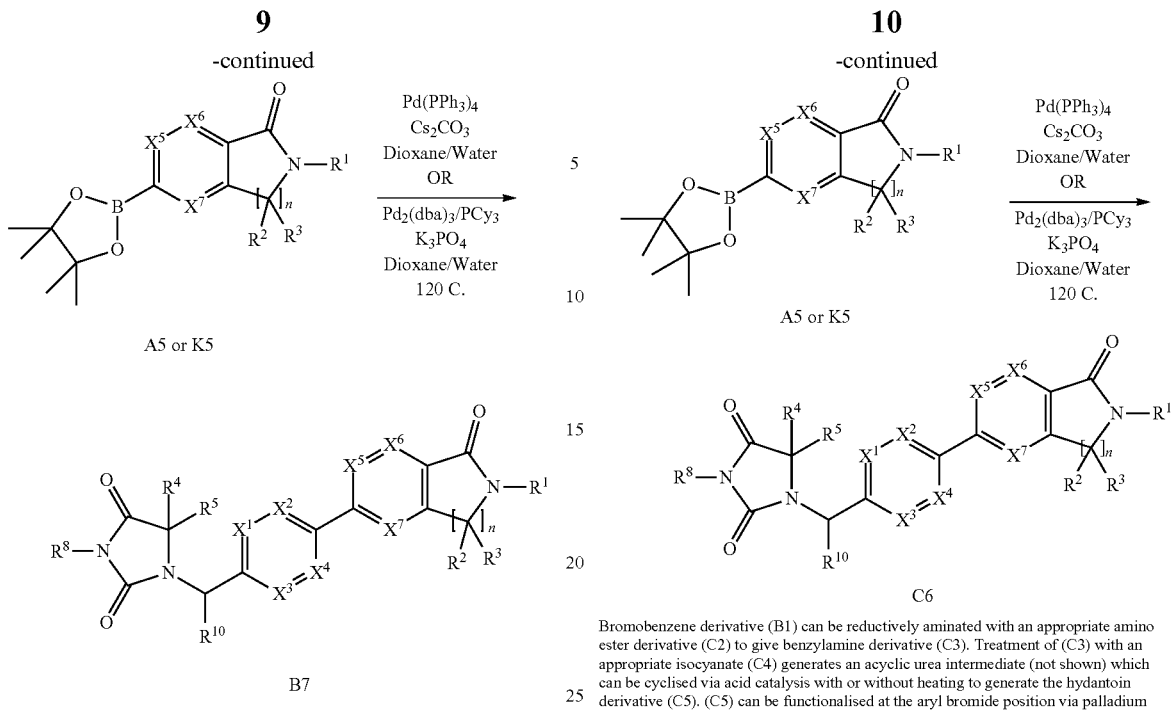

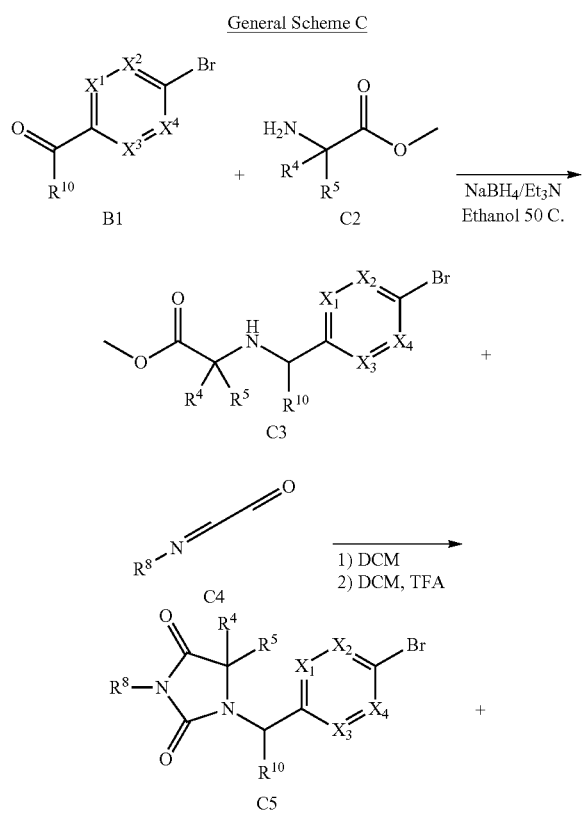

Bromobenzene derivative (B1) can be reductively aminated with a suitable glycineamide derivative (B2) to give amide (B3). Cyclisation mediated by carbonyldiimidazole (CDI) with an appropriate catalyst (e.g. DMAP) gives the unsubstituted hydantoin derivative (B4) which can be functionalised using an appropriate alkylating agent (B5) (X = Cl, Br or I or equivalent) under basic conditions to give hydantoin (B6). (B6) can be functionalised at the aryl bromide position via palladium mediated coupling with a boronic ester derivative (A5 or K5) to give biaryl compound (B7).

Bromobenzene derivative (B1) can be reductively aminated with an appropriate amino ester derivative (C2) to give benzylamine derivative (C3). Treatment of (C3) with an appropriate isocyanate (C4) generates an acyclic urea intermediate (not shown) which can be cyclised via acid catalysis with or without heating to generate the hydantoin derivative (C5). (C5) can be functionalised at the aryl bromide position via palladium mediated coupling with a boronic ester derivative (A5 or K5) to give biaryl compound (C6).

General Scheme C

General Scheme D

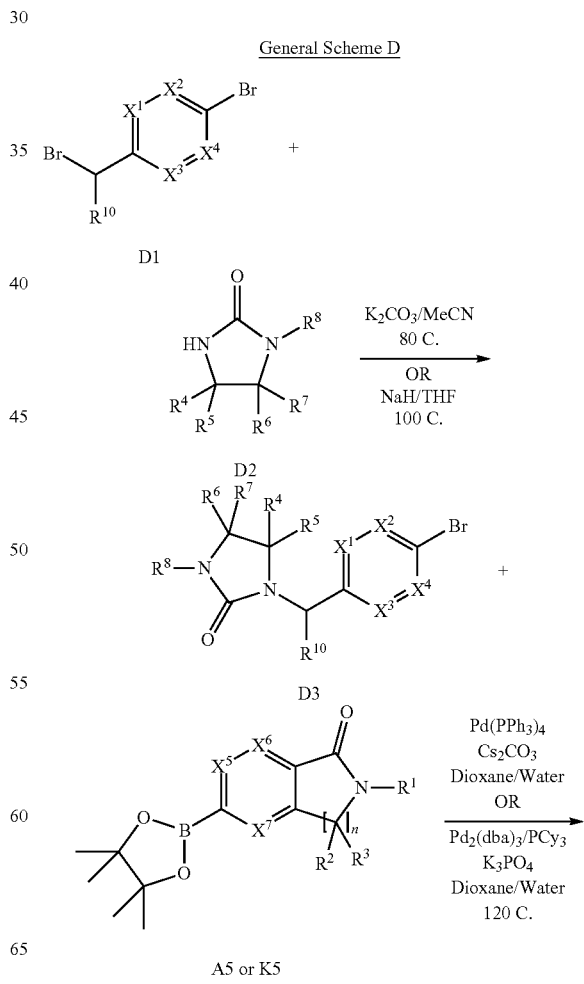

-continued

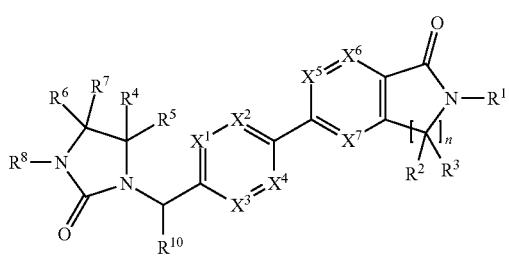

D4

Benzyl bromide (D1) can be reacted with an appropriate urea derivative (D2) (for example a cyclic urea or hydantoin) using base mediated conditions to give the alkylated product (D3). (D3) can be functionalised at the aryl bromide position via palladium mediated coupling with a boronic ester derivative (A5 or K5) to give biaryl compound (D4).

General Scheme E

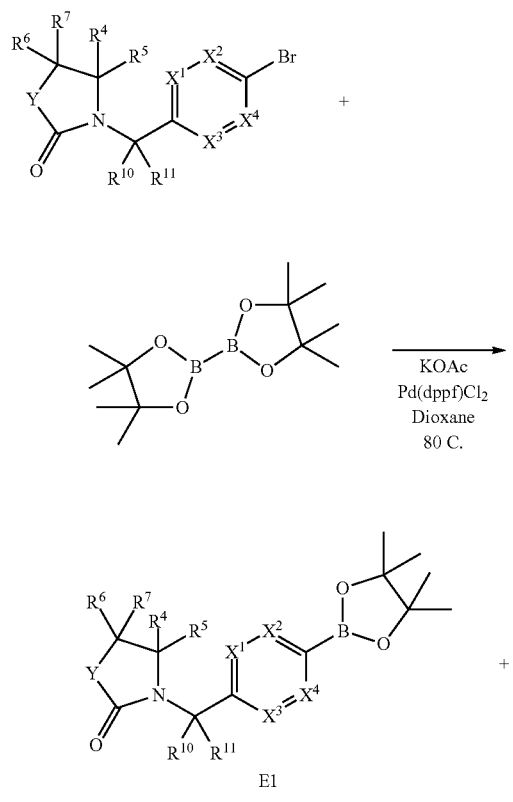

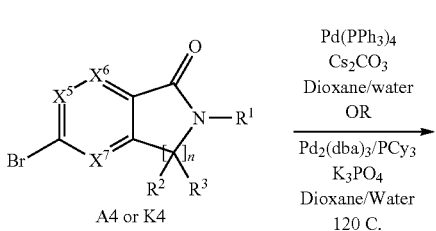

-continued

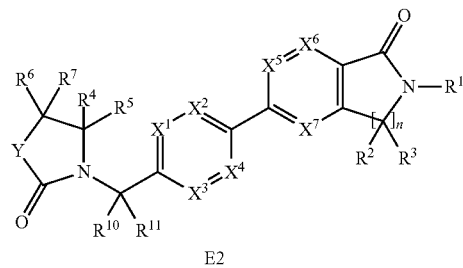

E2

A suitably functionalised aryl bromide derivative (e.g. B6/C5/D3/F3/G4/H5/J5) can be converted to the boronic ester (E1) via palladium mediated coupling. Boronic ester (E1) can be further functionalised with a suitable aryl bromide (A4 or K4) under palladium mediated conditions to give biaryl derivative (E2)

General Scheme F

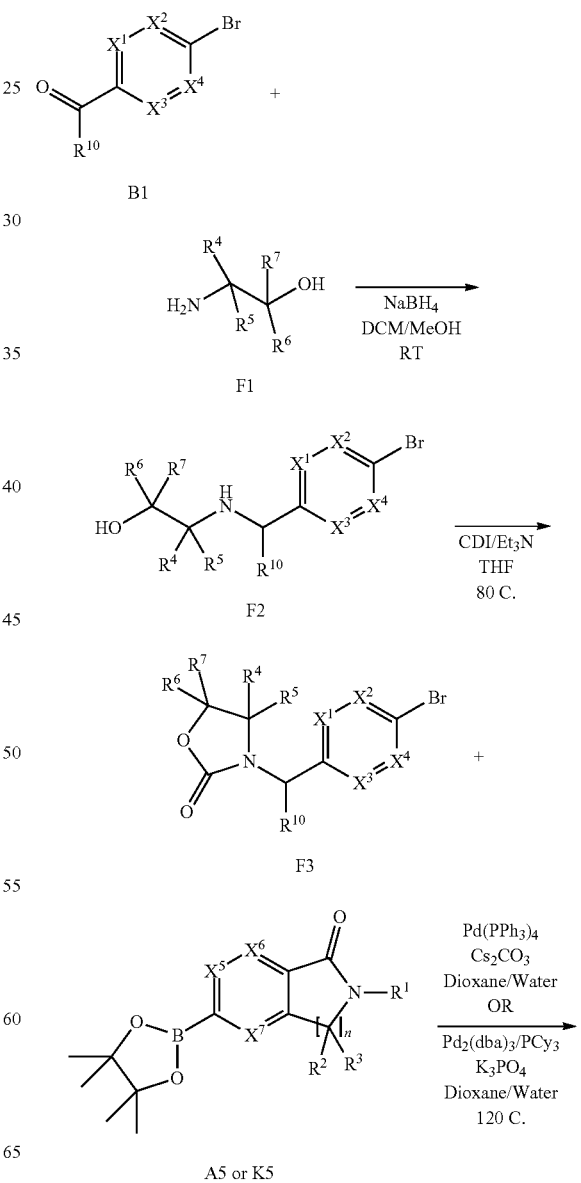

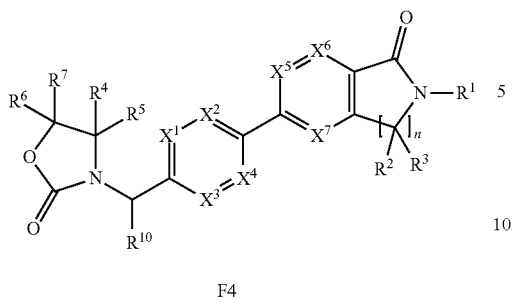

F4

Bromobenzene derivative (B1) can be rductively aminated with an appropriate amino alcohol (F1) to give aminoalcohol derivative (F2). Treatment of (F2) with carbonyldiimidazole (CDI) at elevated temperature gives the corresponding oxazolidinone derivative (F3) which can subsequently be coupled with a boronic ester derivative (A5 or K5) under palladium mediated conditions to give the biaryl derivative (F4)

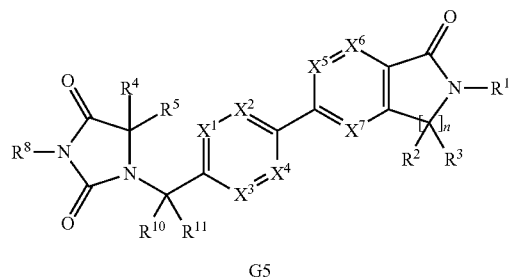

G5

Benzyalmine derivatve (G1) can be alkylated with a suitable alpha-bromo ester (G2) to give the amino ester derivative (G3). Treatment of (G3) with isocyanate (C4) gives an acyclic urea intermediate (not shown) which can be cyclised under acid catalysis with or without heating to give the hydantoin derivative (G4). (G4) can be functionalised at the aryl bromide position via palladium mediated coupling with a boronic ester derivative (A5 or K5) to give biaryl compound (G5).

General Scheme G

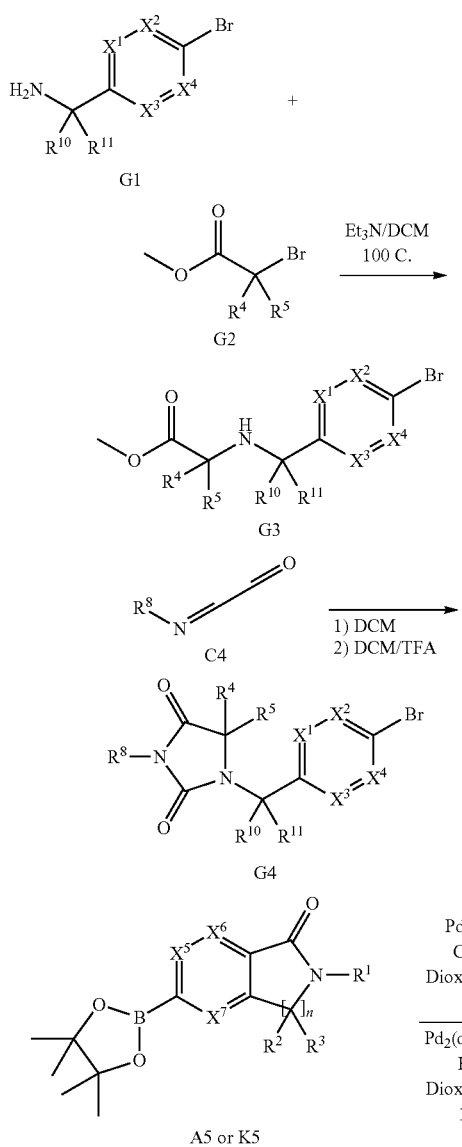

General Scheme H

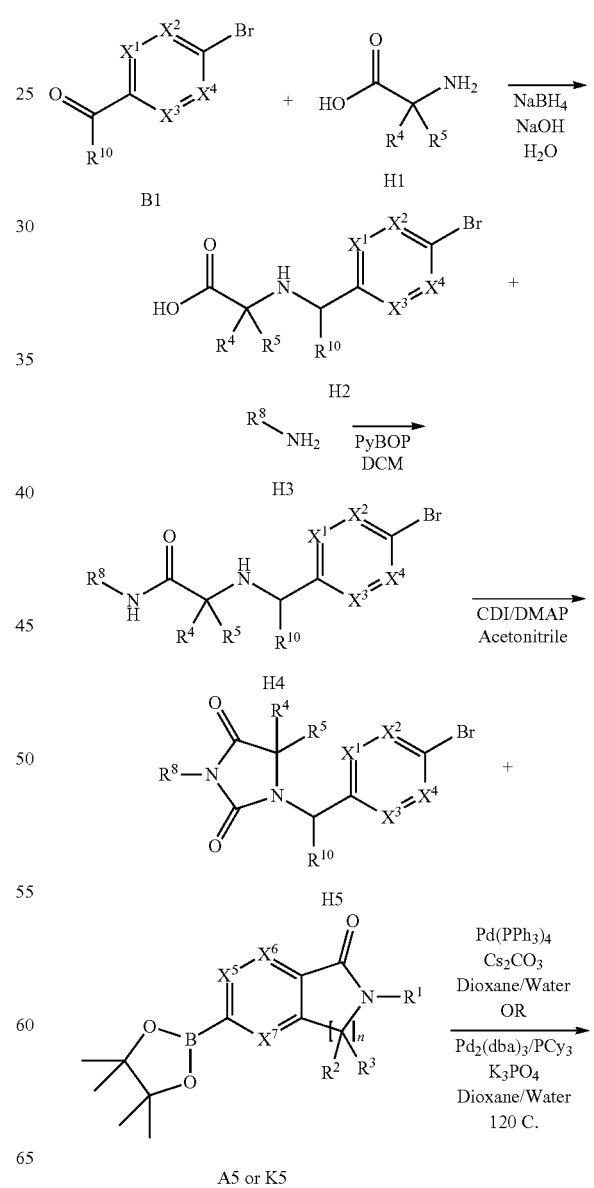

15
-continued

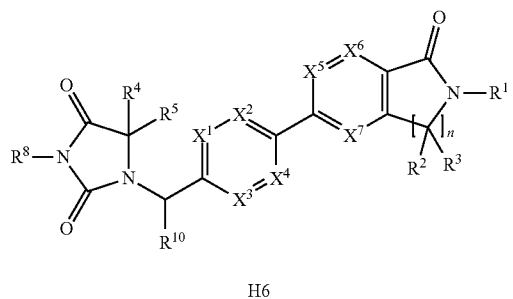

H6

Bromobenzene derivative (B1) can be reductively aminated with a suitable amino acid derivative (H1) to give the amino acid (H2). Treatment of (H2) with suitable coupling reagent and amine (H3) gives amide (H4). Cyclisation of (H4) mediated by carbonyldiimidazole (CDI) and an appropriate catalyst gives the substituted hydantoin derivative (H5) which can be functionalised at the aryl bromide position via palladium mediated coupling with a boronic ester derivative (A5 or K5) to give biaryl compound (H6).

General Scheme I

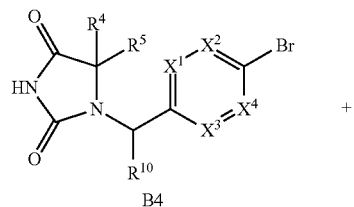

B4

+

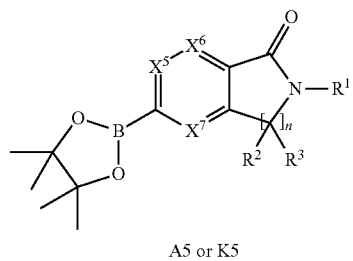

A5 or K5

$$\xrightarrow{\substack{Pd(PPH_3)_4 \\ Cs_2CO_3 \\ Dioxane/water \\ OR \\ Pd_2(dba)_3/PCy_3 \\ K_3PO_4 \\ Dioxane/Water \\ 120\ C.}}$$

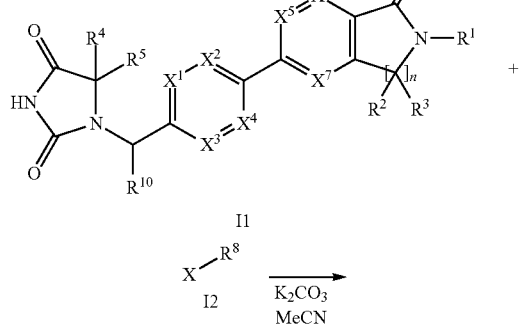

I1

$$\xrightarrow[\substack{K_2CO_3 \\ MeCN}]{X \diagdown R^8 \\ I2}$$

16
-continued

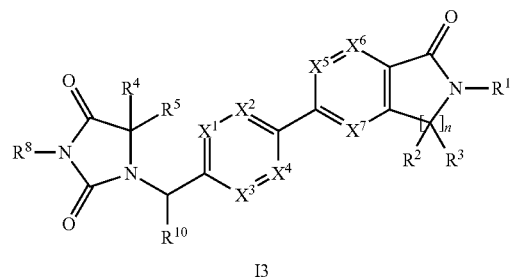

I3

Alternatively (B4) can be first functionalised at the aryl bromide position via palladium mediated coupling with a boronic ester derivative (A5 or K5) to give biaryl compound (I1) which is subsequently functionalised with an appropriate alkylating agent (I2) under basic conditions to give (I3)

General Scheme J

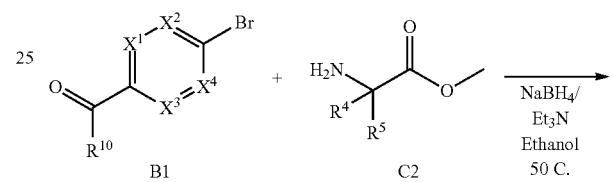

B1     C2

$$\xrightarrow{\substack{NaBH_4/ \\ Et_3N \\ Ethanol \\ 50\ C.}}$$

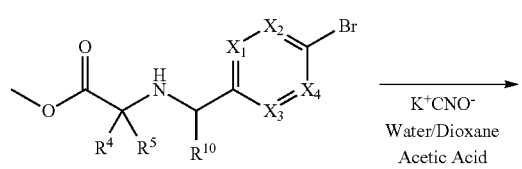

J1

$$\xrightarrow{\substack{K^+CNO^- \\ Water/Dioxane \\ Acetic Acid}}$$

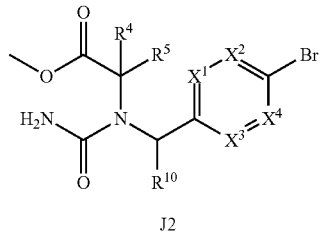

J2

$$\xrightarrow{\substack{NaOMe \\ Methanol}}$$

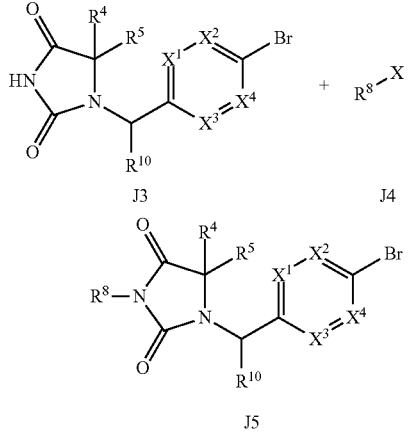

J3     J4

$$\xrightarrow{\substack{K_2CO_3 \\ MeCN}}$$

J5

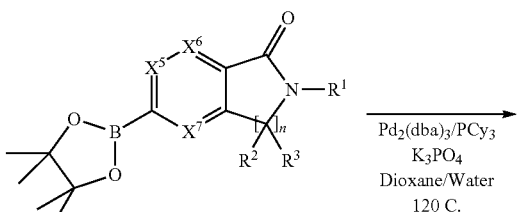

A5 or K5

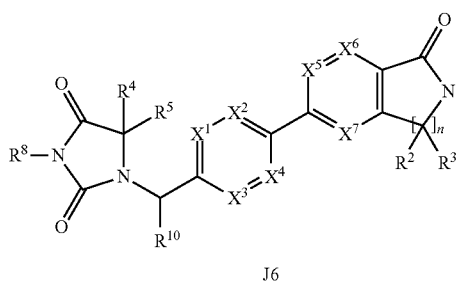

J6

Bromobenzene derivative (B1) can be reductively aminated with a suitable amino ester (C2) to give benzylamine derivative (J1). Reaction of (J1) with potassium cyanate generates urea (J2) which can be cyclised under basic conditions to give the hydantoin (J3). Functionalisation of the hydantoin with an appropriate alkylating agent (J4) gives (J5), which can be further functionalised at the aryl bromide position via palladium mediated coupling with a boronic ester derivative (A5 or K5) to give biaryl compound (J6)

General Scheme K

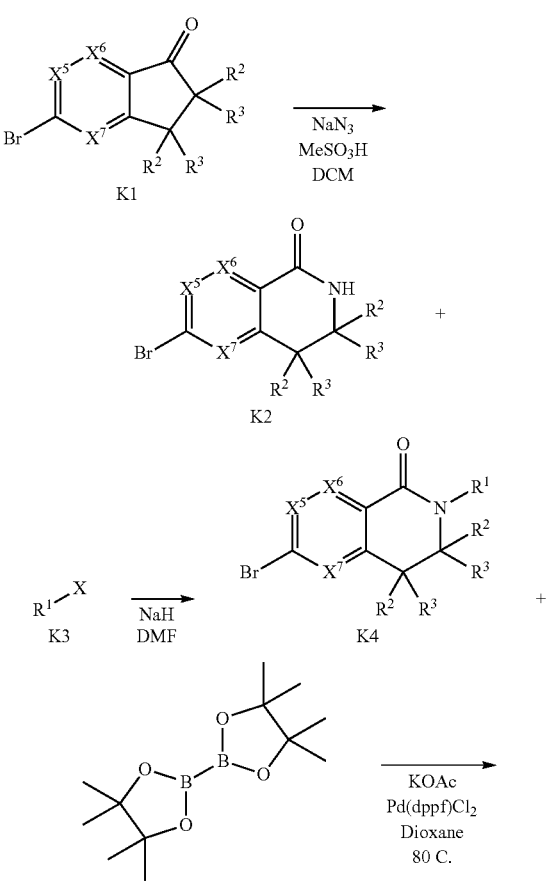

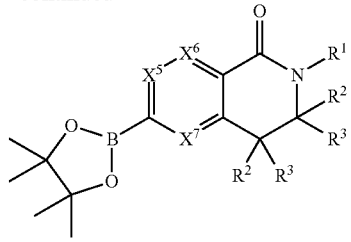

K5

Bromoindanone (K1) undergoes ring expansion using Schmidt methodology to afford bromoisoquinolinone derivative (K2). (K2) can be functionalised with a suitable alkylating agent (K3) to give (K4) which can be used as detailed previously, or further functionalised at the aryl bromide position via palladium mediated coupling to afford the boronic ester inermediate (K5).

The present invention also includes within its scope all stereoisomeric forms of heterocyclic derivatives according to the present invention resulting, for example, from configurational or geometrical isomerism. Such stereoisomeric forms are enantiomers, diastereoisomers, cis and trans isomers etc. In the case of the individual stereoisomers of heterocyclic derivatives of formula I or salts or solvates thereof, the present invention includes the aforementioned stereoisomers substantially free, i.e., associated with less than 5%, preferably less than 2% and in particular less than 1% of the other stereoisomer. Mixtures of stereoisomers in any proportion, for example a racemic mixture comprising substantially equal amounts of two enantiomers are also included within the scope of the present invention.

For chiral compounds, methods for asymmetric synthesis whereby the pure stereoisomers are obtained are well known in the art, e.g., synthesis with chiral induction, synthesis starting from chiral intermediates, enantioselective enzymatic conversions, separation of stereoisomers using chromatography on chiral media. Such methods are described in *Chirality In Industry* (edited by A. N. Collins, G. N. Sheldrake and J. Crosby, 1992; John Wiley). Likewise methods for synthesis of geometrical isomers are also well known in the art.

The heterocyclic derivatives of the present invention, in the form of a free base, may be isolated from reaction mixtures as pharmaceutically acceptable salts. These salts may also be obtained by treatment of said free base with an organic or inorganic acid, for example, hydrogen chloride, hydrogen bromide, hydrogen iodide, sulfuric acid, phosphoric acid, acetic acid, trifluoroacetic acid, propionic acid, glycolic acid, maleic acid, malonic acid, methanesulfonic acid, fumaric acid, succinic acid, tartaric acid, citric acid, benzoic acid and ascorbic acid.

The heterocyclic derivatives of the present invention may also exist as amorphous forms. Multiple crystalline forms are also possible. All these physical forms are included within the scope of the present invention.

Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The present invention also embraces isotopically-labelled compounds of the heterocyclic derivatives described and claimed herein which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{11}$C, $^{13}$C, $^{14}$C, $^{15}$N, $^{18}$O, $^{17}$O, $^{35}$S, $^{18}$F, and $^{36}$Cl, respectively.

Certain isotopically-labelled compounds of Formula I (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Prodrugs of the heterocyclic derivatives of the invention are also contemplated within the scope of the invention. A prodrug is a compound which acts as a drug precursor which, upon administration to a subject, undergoes conversion by metabolic or other chemical processes to yield a heterocyclic derivative of formula I or a solvate or salt thereof. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

In a further aspect, the heterocyclic derivatives of the present invention and their pharmaceutically acceptable salts and solvates are useful in therapy. As such the heterocyclic derivatives of the present invention are useful for the manufacture of a medicament for the treatment or prevention of a neurological or psychiatric disorder associated with glutamate dysfunction, such as for example schizophrenia, anxiety (including generalized anxiety disorder, panic disorder, and obsessive compulsive disorder), dementia (including AIDS-induced dementia), Alzheimer's disease, Huntington's Chorea, cognitive disorders, Parkinson's disease, epilepsy, migraine, deficits associated with traumatic brain injury or stroke, mood disorders (including depression, mania, bipolar disorders), trigeminal neuralgia, pain (including neuropathic pain), tardive dyskinesia, sleep disorders (including narcolepsy), autism, attention deficit hyperactivity disorder, and conduct disorder. The present invention further includes a heterocyclic derivative for use in the treatment of any of the aforementioned diseases or disorders.

The present invention further includes a method for the treatment of a mammal, including a human, suffering from or liable to suffer from any of the aforementioned diseases or disorders, which comprises administering an effective amount of a heterocyclic derivative according to the present invention or a pharmaceutically acceptable salt or solvate thereof. By effective amount or therapeutically effective amount is meant an amount of compound or a composition of the present invention effective in inhibiting the above-noted diseases and thus producing the desired therapeutic, ameliorative, inhibitory or preventative effect.

The amount of a heterocyclic derivative of the present invention or a pharmaceutically acceptable salt or solvate thereof, also referred to herein as the active ingredient, which is required to achieve a therapeutic effect will, of course, vary with the particular compound, the route of administration, the age and condition of the recipient and the particular disorder or disease being treated.

A suitable daily dose for any of the above mentioned disorders will be in the range of 0.001 to 50 mg per kilogram body weight of the recipient (e.g. a human) per day, preferably in the range of 0.01 to 20 mg per kilogram body weight per day. The desired dose may be presented as multiple sub-doses administered at appropriate intervals throughout the day.

Whilst it is possible for the active ingredient to be administered alone, it is preferable to present it as a pharmaceutical composition. The present invention therefore also provides a pharmaceutical composition comprising a heterocyclic derivative according to the present invention in admixture with one or more pharmaceutically acceptable excipients, such as the ones described in Gennaro et. al., Remmington: *The Science and Practice of Pharmacy*, 20$^{th}$ Edition, Lippincott, Williams and Wilkins, 2000; see especially part 5: pharmaceutical manufacturing. Suitable excipients are described e.g., in the Handbook of Pharmaceutical Excipients, 2$^{nd}$ Edition; Editors A. Wade and P. J. Weller, American Pharmaceutical Association, Washington, The Pharmaceutical Press, London, 1994. Compositions include those suitable for oral, nasal, topical (including buccal, sublingual and transdermal), parenteral (including subcutaneous, intravenous and intramuscular) or rectal administration.

The mixtures of a heterocyclic derivative according to the present invention and one or more pharmaceutically acceptable excipient or excipients may be compressed into solid dosage units, such as tablets, or be processed into capsules or suppositories. By means of pharmaceutically suitable liquids the compounds can also be applied as an injection preparation in the form of a solution, suspension, emulsion, or as a spray, e.g., a nasal or buccal spray. For making dosage units e.g., tablets, the use of conventional additives such as fillers, colorants, polymeric binders and the like is contemplated. In general, any pharmaceutically acceptable additive can be used. The heterocyclic derivatives of the invention are also suitable for use in an implant, a patch, a gel or any other preparation for immediate and/or sustained release.

Suitable fillers with which the pharmaceutical compositions can be prepared and administered include lactose, starch, cellulose and derivatives thereof, and the like, or mixtures thereof used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The present invention further includes a pharmaceutical composition, as hereinbefore described, in combination with packaging material suitable for said composition, said packaging material including instructions for the use of the composition for the use as hereinbefore described.

The utility of the compounds in accordance with the present invention as modulators of metabotropic glutamate receptor activity, in particular mGluR2 activity, may be demonstrated by methodology known in the art. The compounds of the present invention may be tested in a fluorescence laser imaging plate reader tetra (FLIPRTETRA) or FlexStation II (Molecular Devices) based assay. Compounds may be tested in vitro for mGluR2 modulatory activity using calcium mobilization assays in the presence of an EC10 concentration of glutamate. This assay is a common functional assay to monitor Ca2+ mobilization in whole cells expressing recombinant receptor coupled with a promiscuous G-protein. HEK cells stably expressing recombinant human mGluR2 receptor, EAAT1 and Gα16 loaded with Fluo4 NW dye (Invitrogen) are treated with a range of concentrations of test compound prepared in an EC10 concentration of glutamate (final concentration 1 μM). The ability to induce a Ca2+ mobilization response in the presence of 1 μM glutamate is monitored on a FLIPRTETRA or FlexStation II (Molecular Devices) and compared to the ability to induce a Ca2+ mobilization response without added glutamate. The presence of an EC10 concentration of glutamate resulted in a significant potentiation of the glutamate response with these compounds which is indicative of a positive modulator of mGluR2.

The maximum calcium response at each concentration of compound is plotted as a concentration response curve and the curves are fitted with a four parameters logistic equation giving EC50 and Hill coefficient using the iterative non linear curve fitting software program ActivityBase.

In particular, the compounds of the following examples demonstrated activity in potentiating mGluR2 receptor responses in the FLIPRTETRA or FlexStation assay, generally with an EC50 of less than about 10 μM. Preferred compounds within the present invention had activity in potentiating the mGluR2 receptor in the FLIPRTETRA or FlexStation assay with an EC50 of less than about 1 μM.

The invention is further illustrated by the following examples which are not intended to limit the scope thereof.

Methods

General Chemical Procedures: All reagents were either purchased from commercial sources or synthesised according to literature procedures beginning from commercial reagents. Commercial reagents were used without further purification. Microwave reactions were performed using an Emrys Optimizer™ (Personal Chemistry). Reactions were monitored by thin layer chromatography and/or mass spectrometry. Ion exchange chromatography was performed using Isolute Flash SCX-II (acidic) resin cartridges. Flash column chromatography was performed using pre-packed silica cartridges (RediSep or Biotage) on a Combiflash™ Retrieve™ system or similar.

Semi-preparative high pressure liquid chromatography (semi-prep. HPLC) was performed using the methods outlined below:

Acidic method: Waters Xterra (RP18, 5 μm) 30 mm×100 mm; 10-100% acetonitrile-water over a 25 minute gradient; 25 mL/min; 0.1% trifluoroacetic acid buffer; detection by UV at 214 or 254 nm.

Basic method: Waters Xterra (RP18, 5 μm) 30 mm×100 mm; 10-100% acetonitrile-water over a 25 minute gradient; 25 mL/min; 5 mM ammonium bicarbonate buffer, adjusted to pH 10 with ammonia; detection by UV at 214 or 254 nm.

Mass spectra were recorded on a Shimadzu LC-8A (HPLC) PE Sciex API 150EX LC/MS or on an Agilent 1200 UPLC with Agilent 6140 LC/MS.

Abbreviations

Dimethylformamide (DMF), dichloromethane (DCM), diethylamine (DEA), ethyl acetate (EtOAc), ethanol (EtOH), methanol (MeOH), tetrahydrofuran (THF), high pressure liquid chromatography (HPLC), thin layer chromatography (TLC), hour (hr), liquid chromatography/mass spectroscopy (LC/MS), mass spectroscopy (MS), preparatory (prep), racemic (rac), strong cation exchange (SCX).

Synthesis of Intermediates

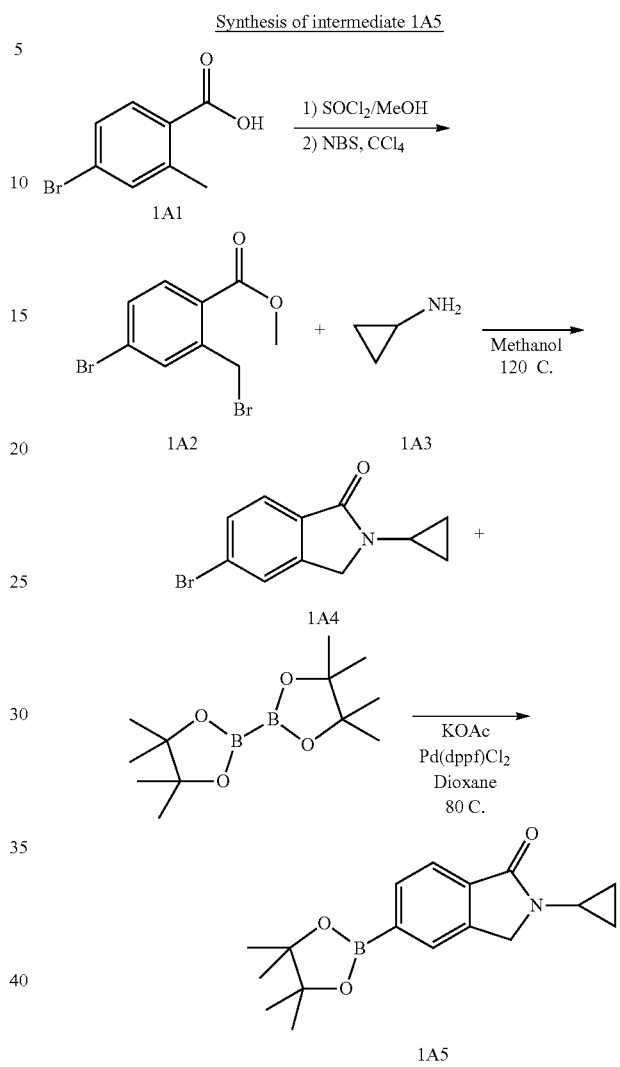

4-Bromo-2-(bromomethyl)benzoate (1A2)

4-Bromo-2-methylbenzoic acid (1A1) was treated according to a literature procedure (WO2008130853) to generate methyl 4-bromo-2-(bromomethyl)benzoate (1A2).

5-Bromo-2-cyclopropylisoindolin-1-one (1A4)

Methyl 4-bromo-2-(bromomethyl)benzoate (1A2) (1.62 mmol, 500 mg) and cyclopropylamine (1A3) (3.25 mmol, 185 mg) in methanol (3 ml) were heated in the microwave at 120° C. for 10 mins. The reaction mixture was concentrated and purified on silica eluting with 50-100% EtOAc/heptane to yield 5-bromo-2-cyclopropylisoindolin-1-one (1A4) 350 mg (84%); ¹H NMR (400 MHz, CDCl₃) δ 7.96 (d, 1H) 7.59 (d, 1H) 7.78 (s, 1H) 4.30 (s, 2H) 2.91 (m, 1H) 0.94-0.85 (m, 4H).

2-Cyclopropyl-5-(4,4,5,5-tetramethyl-1,3,2-dioxaborolan-2-yl)isoindolin-1-one (1A5)

5-bromo-2-cyclopropylisoindolin-1-one (1A4) (20.6 mmol, 5.20 g) bis(pinacolato)diboron (22.69 mmol, 7.57 g), potassium acetate (61.9 mmol, 6.07 g), and dioxane (104 ml) were added to a round bottom flask and sonicated for 10 minutes and then purged with argon for 10 minutes before adding PdCl$_2$dppf (0.619 mmol, 505 mg) The mixture was then heated under nitrogen at 80° C. for 4 hours. The reaction mixture was evaporated to dryness and the residue partitioned between ethyl acetate (100 ml) and water (100 ml). The layers were separated and the aqueous layer extracted further with ethyl acetate (2×75 ml). The organic extracts were combined and washed with water (75 ml) then brine (75 ml). The organic layer was dried over sodium sulphate, filtered and evaporated to dryness to give a dark brown solid which was purified on silica eluting with 0-100% EtOAc in DCM. Desired fractions were combined and evaporated to afford 2-cyclopropyl-5-(4,4,5,5-tetramethyl-1,3,2-dioxaborolan-2-yl)isoindolin-1-one (1A5) 5.82 g (94%); $^1$H NMR (400 MHz, CDCl$_3$) δ 7.89 (d, 1H) 7.85-7.81 (m, 2H) 4.30 (s, 2H) 2.95 (m, 1H) 1.36 (s, 12H) 0.96-0.85 (m, 4H).

Alternative intermediates were prepared in a similar way by replacing either or both of 1A1 and 1A3 with equivalent reagents.

6-Bromo-2-propyl-3,4-dihydroisoquinolin-1(2H)-one (1K4)

Sodium hydride (60% w/w suspension in oil) (1.17 mmol, 46.7 mg) was suspended in DMF (0.5 ml) under argon. The mixture was cooled to 0° C. before dropwise addition of 6-bromo-3,4-dihydroisoquinolin-1(2H)-one (1K2) (1.06 mmol, 240 mg) in DMF (1.5 ml) The reaction was stirred at 0° C. for 30 min before addition of 3-bromopropane (1K3) (1.592 mmol, 196 mg) in DMF (1 ml). Once addition was complete the reaction was allowed to warm to room temperature then heated at 60° C. for 4hrs. The reaction mixture was cooled, quenched with water and extracted three times with diethyl ether. The combined organics were washed with brine, dried (MgSO4) and evaporated to dryness. The residue was purified on silica eluting with 30-100% EtOAc/heptane to give 6-bromo-2-propyl-3,4-dihydroisoquinolin-1(2H)-one (1K4) 202 mg (70.9%); $^1$H NMR (400 MHz, CDCl$_3$) δ 7.94 (d, 1H) 7.47 (d, 1H) 7.33 (s, 1H) 3.54 (m, 4H) 2.96 (t, 2H) 1.65 (m, 2H) 0.96 (t, 3H).

Alternative intermediates were prepared in a similar way by replacing either or both of 1K1 and 1K3 with equivalent reagents.

EXAMPLES

Example 1a 1-(4-(2-Cyclopropyl-1-oxoisoindolin-5-yl)benzyl)-3-methylimidazolidine-2,4-dione

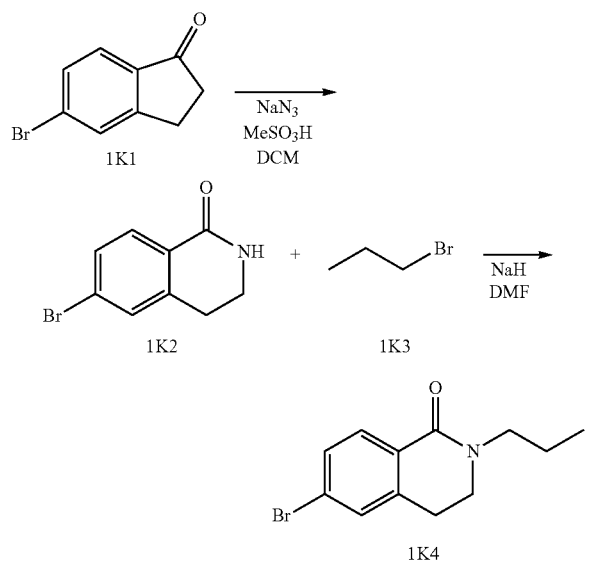

Synthesis of Intermediate 1K4

6-Bromo-3,4-dihydroisoquinolin-1(2H)-one (1K2)

5-bromo-2,3-dihydro-1H-inden-1-one (1K1) (9.48 mmol, 2 g) was dissolved in DCM (35 ml) and methane sulfonic acid (95 mmol, 9.11 g) was added. The reaction mixture was cooled to 0° C. before portionwise addition of sodium azide (28.4 mmol, 1.85 g). Once addition was complete the mixture was allowed to warm to room temperature and stirred overnight. The reaction mixture was partitioned between DCM and NaOH (2M, 50 ml). The phases were separated and the aqueous layer was extracted twice more with DCM. The combined organics were washed with water and brine, dried (MgSO4) and evaporated to dryness before purification on silica eluting with 75-100% EtOAc/heptane to give 6-bromo-3,4-dihydroisoquinolin-1(2H)-one (1K2) 919 mg (42%) $^1$H NMR (400 MHz, CDCl$_3$) δ 7.93 (d, 1H) 7.49 (d, 1H) 7.40 (s, 1H) 6.36 (bs, 1H) 3.58 (t, 2H) 2.99 (t, 2H).

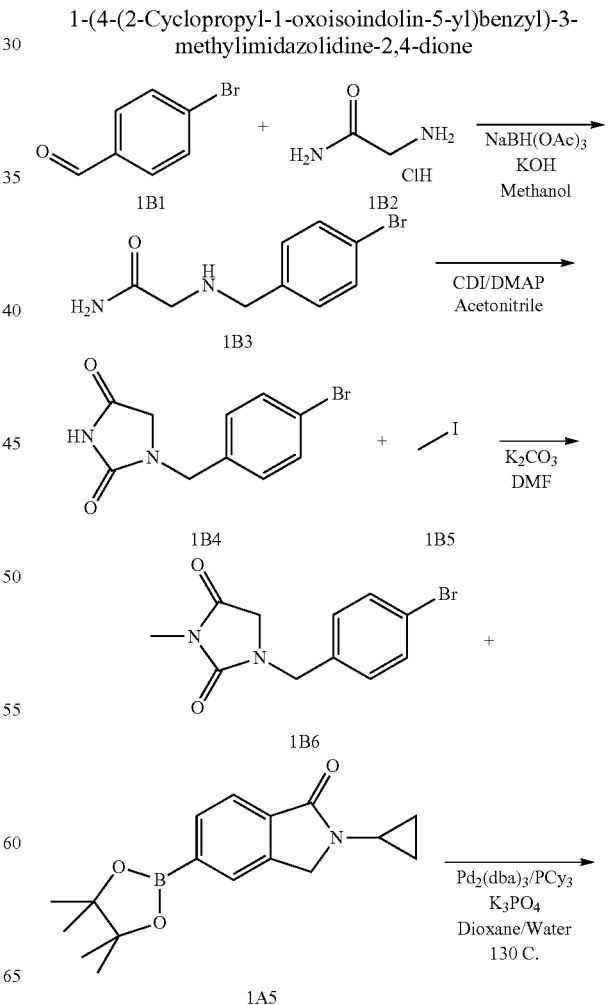

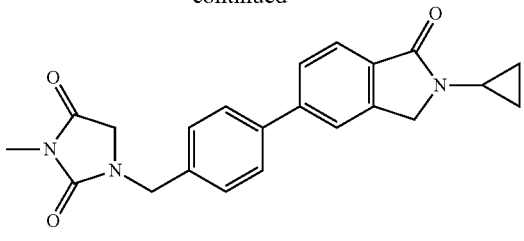

Example 1a

2-(4-Bromobenzylamino)acetamide (1B3)

To glycinamide hydrochloride (1B2) (129 mmol, 15.4 g) in methanol (343 ml) was added potassium hydroxide (9.27 mmol, 0.520 g) followed by 4-bromobenzaldehyde (1B1) (93 mmol, 17.15 g) and the mixture stirred for 15 minutes at 0° C. Sodium triacetoxyborohydride (278 mmol, 58.9 g) was added and stirring continued for 1 h. The reaction was diluted with water (75 ml), DCM (300 ml) and saturated sodium chloride solution (100 ml) and the phases separated. The aqueous layer was washed twice with DCM (100 ml) before addition of sodium hydroxide solution to ~pH10 and the resulting precipitate was collected by filtration to give 2-(4-bromobenzylamino)acetamide (1B3) 13.2 g (58.5%); $^1$H NMR (400 MHz, DMSO$_{d6}$) δ 7.50 (d, 2H) 7.31 (d, 2H) 7.08 (bs, NH$_2$) 3.65 (s, 2H) 3.01 (s, 2H) 2.58 (bs, NH).

1-(4-Bromobenzyl)imidazolidine-2,4-dione (1B4)

A mixture of 2-(4-bromobenzylamino)acetamide (1B3) (45.9 mmol, 11.2 g) and carbonyldiimidazole (68.8 mmol, 11.2 g) in acetonitrile (223 ml) was cooled to 0° C. with stirring and 4-dimethylaminopyridine (45.9 mmol, 5.60 g) was added. The mixture was stirred at 0° C. for 24 h and then heated at 80° C. for 18 h. The reaction mixture was diluted with water and the acetonitrile removed under reduced pressure. The mixture was acidified to pH 4 with aqueous HCl and the precipitate collected by filtration and dried in a vacuum oven to give 1-(4-bromobenzyl)imidazolidine-2,4-dione (1B4) 2.55 g (20.2%); $^1$H NMR (400 MHz, DMSO$_{d6}$) δ 10.94 (bs, NH) 7.55 (d, 2H) 7.24 (d, 2H) 4.42 (s, 2H) 3.86 (s, 2H).

1-(4-Bromobenzyl)-3-methylimidazolidine-2,4-dione (1B6)

1-(4-Bromobenzyl)imidazolidine-2,4-dione (1B4) (1.86 mmol, 500 mg) was dissolved in DMF (7 ml) and potassium carbonate (5.57 mmol, 770 mg) and iodomethane (1B5) (1.86 mmol, 0.116 ml, 264 mg) were added and the reaction mixture was stirred at 50° C. under nitrogen. The reaction was monitored by TLC and after 48 h of heating some starting material remained. An additional 2 equivalents of iodomethane (3.72 mmol, 0.232 ml, 528 mg) was added and the mixture stirred at 75° C. under nitrogen overnight. The reaction mixture was cooled to room temperature, filtrated and concentrated, then purified on silica eluting with heptane/EtOAc/EtOH 5/4/1 to give 1-(4-bromobenzyl)-3-methylimidazolidine-2,4-dione (1B6) 438 mg, (83%); $^1$H NMR (400 MHz, CDCl$_3$) 7.51 (d, 2H) 7.15 (d, 2H) 4.53 (s, 2H) 3.74 (s, 2H) 3.06 (s, 3H).

1-(4-(2-Cyclopropyl-1-oxoisoindolin-5-yl)benzyl)-3-methylimidazolidine-2,4-dione

Example 1a

2-Cyclopropyl-5-(4,4,5,5-tetramethyl-1,3,2-dioxaborolan-2-yl)isoindolin-1-one (1A5) (3.34 mmol, 1.0 g), 1-(4-bromobenzyl)-3-methylimidazolidine-2,4-dione (1B6) (3.34 mmol, 0.946 g), tris(dibenzylidineacetone)dipalladium (0.167 mmol, 153 mg), tricyclohexylphosphine (0.401 mmol, 112 mg) and potassium phosphate (5.68 mmol, 1.2 mg) were suspended in a mixture of dioxane (10 ml) and water (5 ml) and heated at 130° C. in the microwave for 15 min. The reaction was quenched with sat. NaHCO$_3$ and diluted with DCM and then passed through a hydrophobic fritted tube. The combined organic layers were concentrated and the residue purified on silica eluting with 75-100% EtOAc/Heptane to afford 1-(4-(2-cyclopropyl-1-oxoisoindolin-5-yl)benzyl)-3-methylimidazolidine-2,4-dione (Example 1a) (685 mg, 55%) $^1$H NMR (400 MHz, CDCl$_3$) δ 7.99 (d, 1H) 7.65 (d, 1H) 7.62 (d, 2H) 7.59 (s, 1H) 7.36 (d, 2H) 4.63 (s, 2H) 4.38 (s, 2H) 3.79 (s, 2H) 3.08 (s, 3H) 2.95 (m, 1H) 0.98-0.87 (m, 4H) LCMS m/z (M+H) 376.2.

The following compounds were prepared in a similar way replacing one or more of 1B1, 1B2, 1B5 and 1A5 with equivalent reagents:

| Ex. | Structure | Name | M/S |
|---|---|---|---|
| 1b | 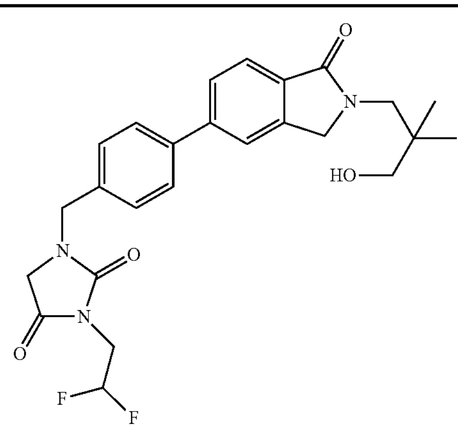 | 3-(2,2-difluoroethyl)-1-(4-(2-(3-hydroxy-2,2-dimethylpropyl)-1-oxoisoindolin-5-yl)benzyl)imidazolidine-2,4-dione | 472.2 |

-continued
| Ex. | Structure | Name | M/S |
|---|---|---|---|
| 1c | 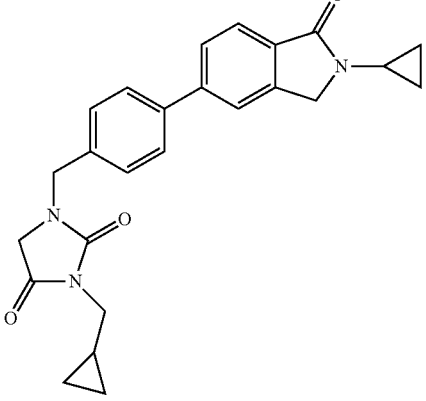 | 1-(4-(2-cyclopropyl-1-oxoisoindolin-5-yl)benzyl)-3-(cyclopropylmethyl)imidazolidine-2,4-dione | 416.2 |
| 1d | 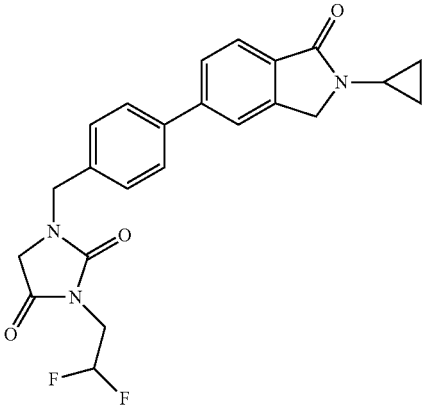 [SMILES: O=C1CN(Cc2ccc(-c3ccc4c(c3)CN(C3CC3)C4=O)cc2)C(=O)N1CC(F)F] | 1-(4-(2-cyclopropyl-1-oxoisoindolin-5-yl)benzyl)-3-(2,2-difluoroethyl)imidazolidine-2,4-dione | 426.0 |
| 1e | 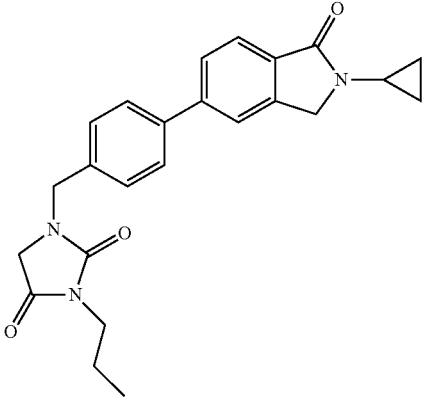 [SMILES: CCCN1C(=O)CN(Cc2ccc(-c3ccc4c(c3)CN(C3CC3)C4=O)cc2)C1=O] | 1-(4-(2-cyclopropyl-1-oxoisoindolin-5-yl)benzyl)-3-propylimidazolidine-2,4-dione | 404.2 |

-continued
| Ex. | Structure | Name | M/S |
|---|---|---|---|
| 1f | 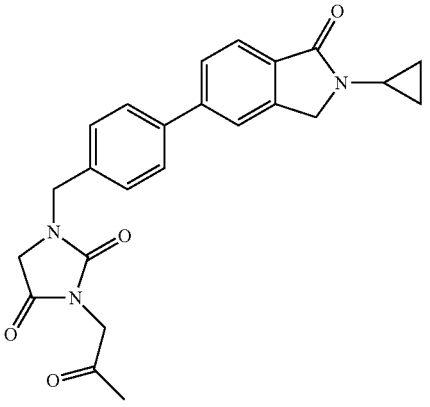 [SMILES: CC(=O)CN1C(=O)CN(Cc2ccc(-c3ccc4c(c3)CN(C3CC3)C4=O)cc2)C1=O] | 1-(4-(2-cyclopropyl-1-oxoisoindolin-5-yl)benzyl)-3-(2-oxopropyl)imidazolidine-2,4-dione | 418.2 |
| 1g | 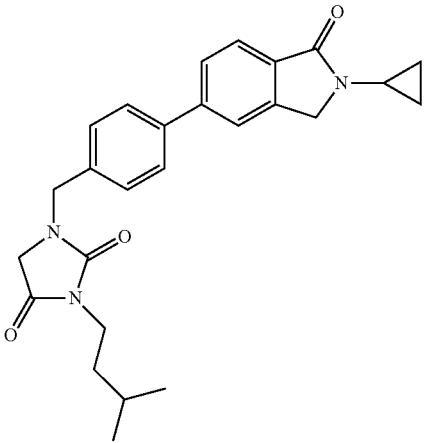 [SMILES: CC(C)CCN1C(=O)CN(Cc2ccc(-c3ccc4c(c3)CN(C3CC3)C4=O)cc2)C1=O] | 1-(4-(2-cyclopropyl-1-oxoisoindolin-5-yl)benzyl)-3-isopentylimidazolidine-2,4-dione | 432.2 |
| 1h | 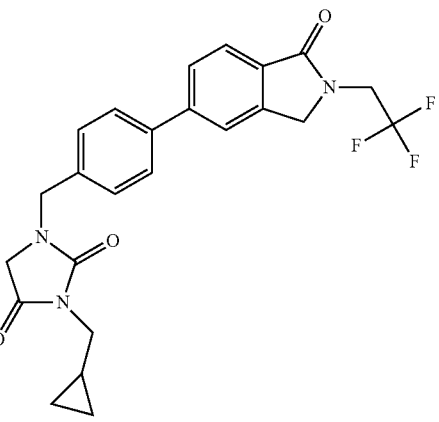 | 3-(cyclopropylmethyl)-1-(4-(1-oxo-2-(2,2,2-trifluoroethyl)isoindolin-5-yl)benzyl)imidazolidine-2,4-dione | 458.0 |

US 8,507,521 B2

| Ex. | Structure | Name | M/S |
|---|---|---|---|
| 1i | 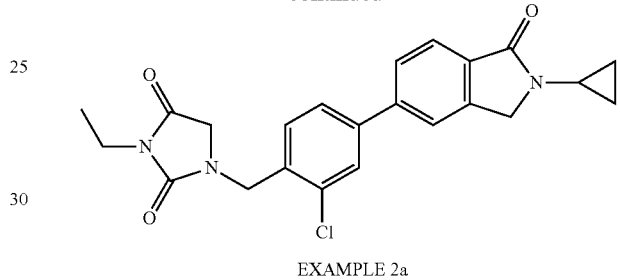 | 3-(2,2-difluoroethyl)-1-(4-(1-oxo-2-(2,2,2-trifluoroethyl)isoindolin-5-yl)benzyl)imidazolidine-2,4-dione | 468.0 |

Example 2a

1-(2-Chloro-4-(2-cyclopropyl-1-oxoisoindolin-5-yl)benzyl)-3-ethylimidazolidine-2,4-dione

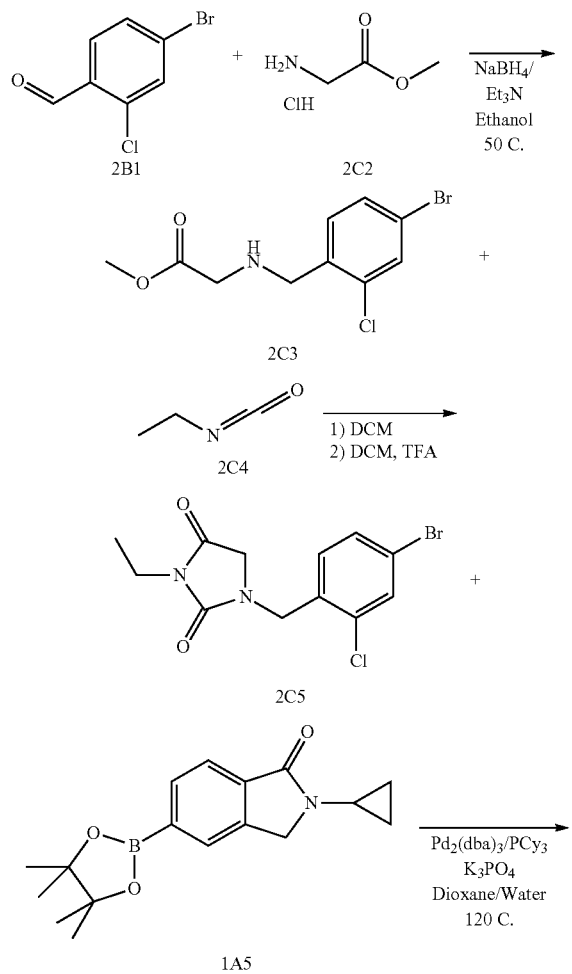

EXAMPLE 2a

Methyl 2-(4-bromo-2-chlorobenzylamino)acetate (2C3)

4-bromo-2-chlorobenzaldehyde (2B1) (4.56 mmol, 1.0 g) and glycine methyl ester hydrochloride (2C2) (4.56 mmol, 572 mg) were dissolved in ethanol (15 ml) under nitrogen with stirring and triethylamine (135 mmol, 19.0 ml, 13.7 g) was added. The reaction mixture was heated to 50° C. for 1 hour, then evaporated to dryness and the residue taken up in methanol (15 ml) and cooled in an ice bath. Sodium borohydride (5.01 mmol, 0.190 g) was added portionwise and stirring continued until no starting material remained as determined by TLC. The reaction mixture was concentrated to dryness and partitioned between DCM and water and the phases separated. The organic layer was dried over sodium sulphate, filtered and concentrated before purification on silica eluting with 15% EtOAc/heptane to yield methyl 2-(4-bromo-2-chlorobenzylamino)acetate (2C3) 420 mg (31%); $^1$H NMR (400 MHz, CDCl$_3$) δ 7.53 (s, 1H) 7.38 (d, 1H) 7.31 (d, 1H) 3.86 (s, 2H) 3.73 (s, 3H) 3.43 (s, 2H).

1-(4-Bromo-2-chlorobenzyl)-3-ethylimidazolidine-2,4-dione (2C5)

Methyl 2-(4-bromo-2-chlorobenzylamino)acetate (2C3) (1.44 mmol, 420 mg) was dissolved in DCM (35 ml) and ethyl isocyanate (2C4) (2.87 mmol, 0.227 ml, 204 mg) added. The mixture was stirred at room temperature overnight. The mixture was concentrated and azeotroped with DCM three times and then re-dissolved in DCM (10 ml) and TFA (3 ml) added. The solution was stirred for 1.5 h then quenched with saturated sodium carbonate solution and the phases separated. The aqueous layer was washed with DCM twice and the combined organics dried over sodium sulphate, filtered and concentrated to give 1-(4-bromo-2-chlorobenzyl)-3-ethylimidazolidine-2,4-dione (2C5) 430 mg (90%); $^1$H NMR (400 MHz, CDCl$_3$) δ 7.58 (s, 1H) 7.42 (d, 1H) 7.22 (d, 1H) 4.65 (s, 2H) 3.79 (s, 2H) 3.59 (q, 2H) 1.23 (t, 3H).

1-(2-Chloro-4-(2-cyclopropyl-1-oxoisoindolin-5-yl)benzyl)-3-ethvlimidazolidine-2,4-dione Example 2a 1-(4-Bromo-2-chlorobenzyl)-3-ethylimidazolidine-2,4-dione (2C5) (0.106 mmol, 35 mg), 2-cyclopropyl-5-(4,4,5,5-tetramethyl-1,3,2-dioxaborolan-2-yl)isoindolin-1-one (1A5) (106 mmol, 31.6 mg), tris(dibenzylidineacetone)dipalladium (0.005 mmol, 4.8 mg), tricyclohexylphosphine (0.013 mmol, 3.6 mg) and potassium phosphate (0.317 mmol, 67 mg) were dissolved in dioxane (2 ml) and water (1 ml) and the mixture was heated at 120° C. in the microwave for 30 min. The sample was concentrated and partitioned between DCM and water and the organic layer collected and dried using a hydrophobic fritted tube before concentration. Purification using basic semi-prep HPLC afforded 1-(2-chloro-4-(2-cyclopropyl-1-oxoisoindolin-5-yl)benzyl)-3-ethylimidazolidine-2,4-dione (Example 2a) 15.1 mg (33%); $^1$H NMR (400 MHz, CDCl$_3$) δ 7.90 (d, 1H) 7.62 (m, 2H) 7.56 (s, 1H) 7.51 (d, 1H) 7.43 (d, 1H) 4.76 (s, 2H) 4.39 (s, 2H) 3.85 (s, 2H) 3.61 (q, 2H) 2.98 (m, 1H) 1.25 (t, 3H) 0.96-89 (m, 4H); LCMS m/z (M+H) 424.0.

The following compounds were prepared in a similar way replacing one or more of 2B1, 2C2, 2C4 and 1A5 with equivalent reagents:

| Ex. | Structure | Name | M/S |
|---|---|---|---|
| 2b | 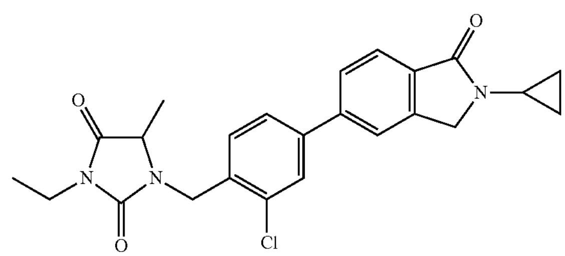 [SMILES: CCN1C(=O)C(C)N(Cc2ccc(-c3ccc4c(c3)CN(C3CC3)C4=O)cc2Cl)C1=O] | 1-(2-chloro-4-(2-cyclopropyl-1-oxoisoindolin-5-yl)benzyl)-3-ethyl-5-methylimidazolidine-2,4-dione | 438.0 |
| 2c | 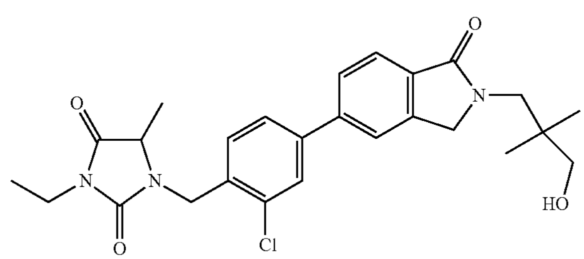 [SMILES: CCN1C(=O)C(C)N(Cc2ccc(-c3ccc4c(c3)CN(CC(C)(C)CO)C4=O)cc2Cl)C1=O] | 1-(2-chloro-4-(2-(3-hydroxy-2,2-dimethylpropyl)-1-oxoisoindolin-5-yl)benzyl)-3-ethyl-5-methylimidazolidine-2,4-dione | 484.2 |
| 2d | 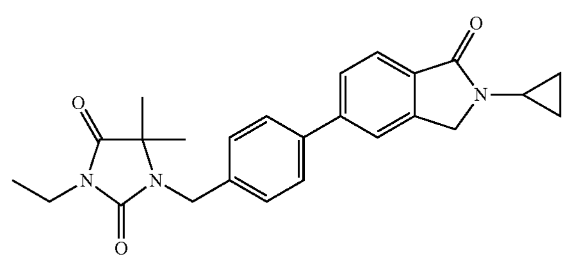 [SMILES: CCN1C(=O)N(Cc2ccc(-c3ccc4c(c3)CN(C3CC3)C4=O)cc2)C(C)(C)C1=O] | 1-(4-(2-cyclopropyl-1-oxoisoindolin-5-yl)benzyl)-3-ethyl-5,5-dimethylimidazolidine-2,4-dione | 418.2 |
| 2e | 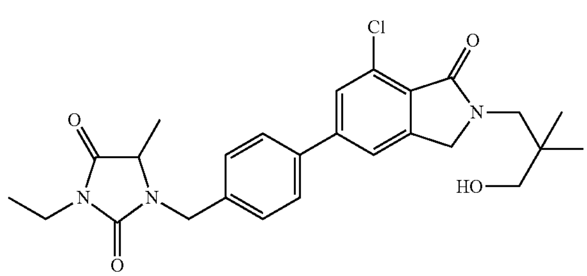 [SMILES: CCN1C(=O)C(C)N(Cc2ccc(-c3cc(Cl)c4c(c3)CN(CC(C)(C)CO)C4=O)cc2)C1=O] | 1-(4-(7-chloro-2-(3-hydroxy-2,2-dimethylpropyl)-1-oxoisoindolin-5-yl)benzyl)-3-ethyl-5-methylimidazolidine-2,4-dione | 484.2 |

| Ex. | Structure | Name | M/S |
|---|---|---|---|
| 2f | 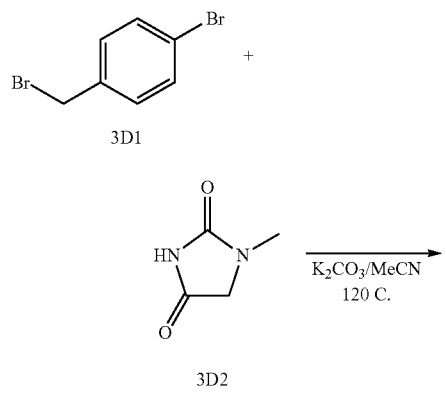 | 1-(4-(7-chloro-2-(3-hydroxy-2,2-dimethylpropyl)-1-oxoisoindolin-5-yl)benzyl)-3-ethylimidazolidine-2,4-dione | 470.2 |
| 2g | 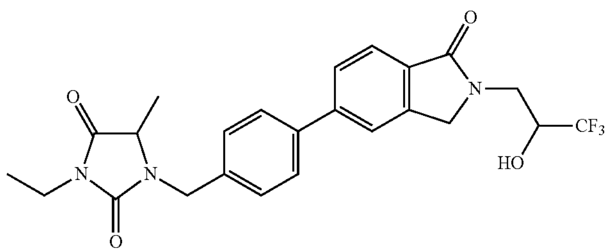 [SMILES: CCN1C(=O)C(C)N(Cc2ccc(-c3ccc4c(c3)CN(CC(O)C(F)(F)F)C4=O)cc2)C1=O] | 3-ethyl-5-methyl-1-(4-(1-oxo-2-(3,3,3-trifluoro-2-hydroxypropyl)isoindolin-5-yl)benzyl)imidazolidine-2,4-dione | 476.2 |
| 2h | 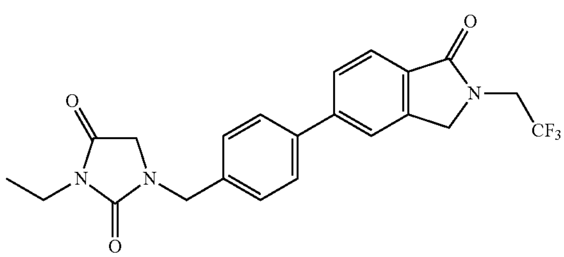 [SMILES: CCN1C(=O)CN(Cc2ccc(-c3ccc4c(c3)CN(CC(F)(F)F)C4=O)cc2)C1=O] | 3-ethyl-1-(4-(1-oxo-2-(2,2,2-trifluoroethyl)isoindolin-5-yl)benzyl)imidazolidine-2,4-dione | 432.0 |

Example 3a

3-(4-(2-Cyclopropyl-1-oxoisoindolin-5-yl)benzyl)-1-methylimidazolidine-2,4-dione

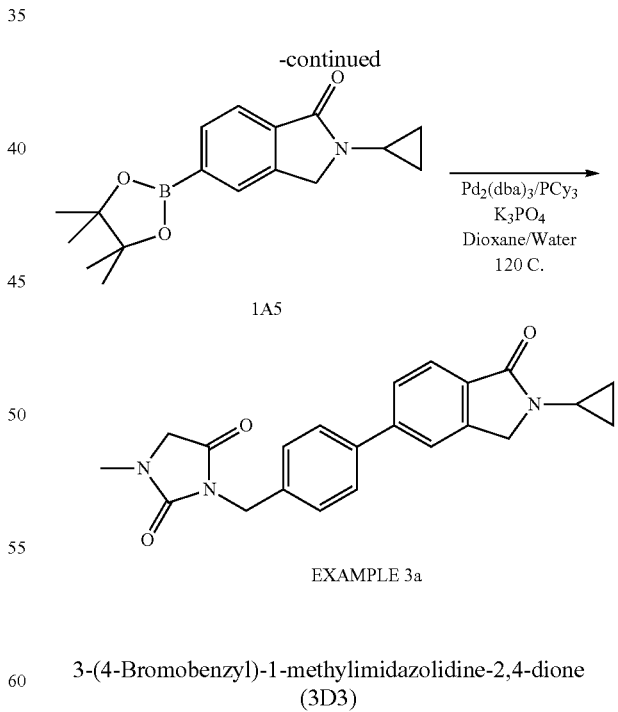

3-(4-Bromobenzyl)-1-methylimidazolidine-2,4-dione (3D3)

1-Methylimidazolidine-2,4-dione (0.876 mmol, 100 mg), 1-bromo-4-(bromomethyl)benzene (0.964 mmol, 241 mg) and potassium carbonate (1.75 mmol, 242 mg) in acetonitrile (3 ml) were heated in the microwave at 120° C. for 1 h. The mixture was partitioned between water and DCM and the organic phase separated using a hydrophobic frit and concentrated to afford 3-(4-bromobenzyl)-1-methylimidazolidine-2,4-dione (3D3); $^1$H NMR (400 MHz, CDCl$_3$) δ 7.44 (d, 2H) 7.29 (d, 2H) 4.59 (s, 2H) 3.85 (s, 2H) 2.98 (s, 3H).

3-(4-(2-Cyclopropyl-1-oxoisoindolin-5-yl)benzyl)-1-methylimidazolidine-2,4-dione Example 3a 2-cyclopropyl-5-(4,4,5,5-tetramethyl-1,3,2-dioxaborolan-2-yl)isoindolin-1-one (1A5) (0.08 mmol, 26.4 mg), 3-(4-bromobenzyl)-1-methylimidazolidine-2,4-dione (3D3) (0.08 mmol, 25.0 mg), tris(dibenzylidineacetone)dipalladium (0.004 mmol, 4.12 mg), tricyclohexylphosphine (0.096 mmol, 3.1 mg) and potassium phosphate (0.16 mmol, 39.0 mg) were suspended in dioxane (1 ml) and water (0.5 ml) and heated at 120° C. in the microwave for 20 min. The reaction was diluted with DCM (2 ml) and water (2 ml) then passed through a hydrophobic fritted tube. The organic phase was concentrated and the residue purified on basic HPLC to give 3-(4-(2-cyclopropyl-1-oxoisoindolin-5-yl)benzyl)-1-methylimidazoline-2,4-dione (Example 3a) (685 mg, 55%) $^1$H NMR (400 MHz, CDCl$_3$) δ 7.87 (d, 1H) 7.64 (d, 1H) 7.57-7.50 (m, 5H) 4.71 (s, 2H) 4.37 (s, 2H) 3.89 (s, 2H) 3.01 (s, 3H) 2.95 (m, 1H) 0.95-0.88 (m, 4H) LCMS m/z (M+H) 376.0.

The following compounds were prepared in a similar way replacing one or more of 3D1, 3D2 or 1A5 with equivalent reagents:

| Ex. | Structure | Name | M/S |
|---|---|---|---|
| 3b | 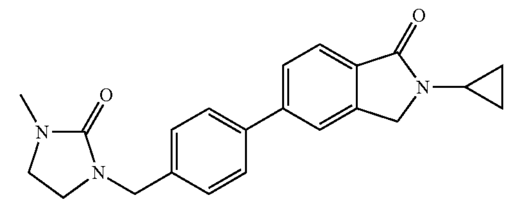 [SMILES: CN1CCN(Cc2ccc(-c3ccc4c(c3)CN(C3CC3)C4=O)cc2)C1=O] | 2-cyclopropyl-5-(4-((3-methyl-2-oxoimidazolidin-1-yl)methyl)phenyl)isoindolin-1-one | 362.2 |
| 3c | 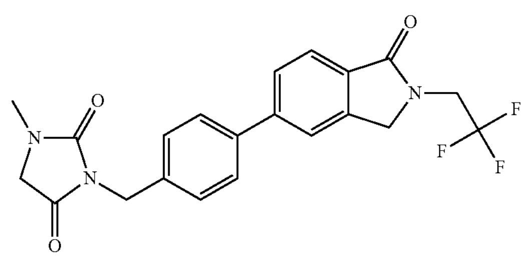 [SMILES: CN1CC(=O)N(Cc2ccc(-c3ccc4c(c3)CN(CC(F)(F)F)C4=O)cc2)C1=O] | 1-methyl-3-(4-(1-oxo-2-(2,2,2-trifluoroethyl)isoindolin-5-yl)benzyl)imidazolidine-2,4-dione | 418.0 |
| 3d | 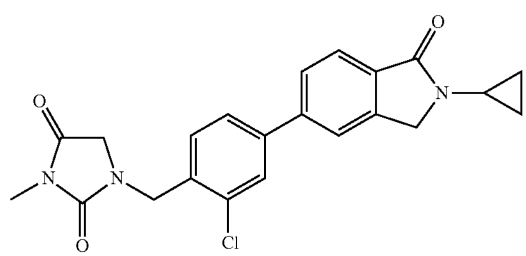 | 1-(2-chloro-4-(2-cyclopropyl-1-oxoisoindolin-5-yl)benzyl)-3-methylimidazolidine-2,4-dione | 410.0 |
| 3e | 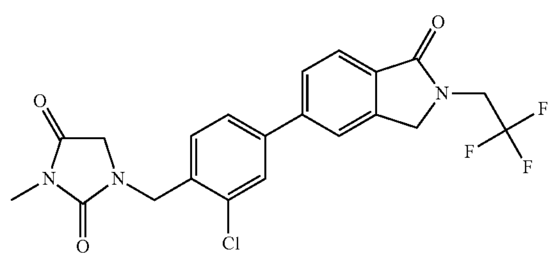 [SMILES: CN1C(=O)CN(Cc2ccc(-c3ccc4c(c3)CN(CC(F)(F)F)C4=O)cc2Cl)C1=O] | 1-(2-chloro-4-(1-oxo-2-(2,2,2-trifluoroethyl)isoindolin-5-yl)benzyl)-3-methylimidazolidine-2,4-dione | 452 |

-continued

| Ex. | Structure | Name | M/S |
|---|---|---|---|
| 3f | 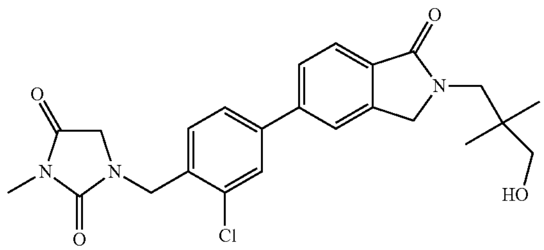 [SMILES: CN1C(=O)CN(Cc2ccc(-c3ccc4c(c3)CN(CC(C)(C)CO)C4=O)cc2Cl)C1=O] | 1-(2-chloro-4-(2-(3-hydroxy-2,2-dimethylpropyl)-1-oxoisoindolin-5-yl)benzyl)-3-methylimidazolidine-2,4-dione | 456.2 |
| 3g | 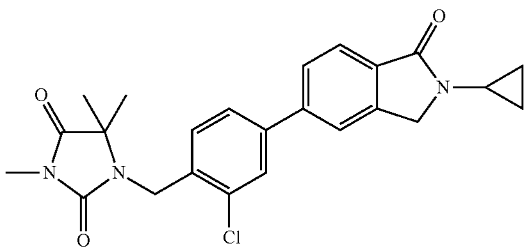 [SMILES: CN1C(=O)N(Cc2ccc(-c3ccc4c(c3)CN(C3CC3)C4=O)cc2Cl)C(C)(C)C1=O] | 1-(2-chloro-4-(2-cyclopropyl-1-oxoisoindolin-5-yl)benzyl)-3,5,5-trimethylimidazolidine-2,4-dione | 438.2 |
| 3h | 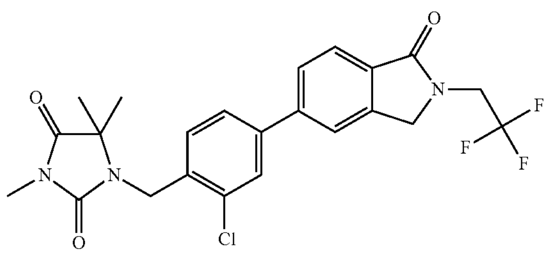 [SMILES: CN1C(=O)N(Cc2ccc(-c3ccc4c(c3)CN(CC(F)(F)F)C4=O)cc2Cl)C(C)(C)C1=O] | 1-(2-chloro-4-(1-oxo-2-(2,2,2-trifluoroethyl)isoindolin-5-yl)benzyl)-3,5,5-trimethylimidazolidine-2,4-dione | 480.0 |
| 3i | 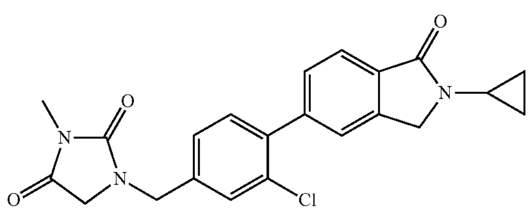 [SMILES: CN1C(=O)CN(Cc2ccc(-c3ccc4c(c3)CN(C3CC3)C4=O)c(Cl)c2)C1=O] | 1-(3-chloro-4-(2-cyclopropyl-1-oxoisoindolin-5-yl)benzyl)-3-methylimidazolidine-2,4-dione | 410.0 |
| 3j | 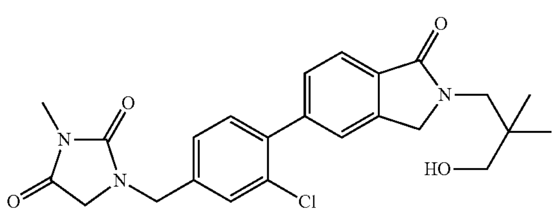 [SMILES: CN1C(=O)CN(Cc2ccc(-c3ccc4c(c3)CN(CC(C)(C)CO)C4=O)c(Cl)c2)C1=O] | 1-(3-chloro-4-(2-(3-hydroxy-2,2-dimethylpropyl)-1-oxoisoindolin-5-yl)benzyl)-3-methylimidazolidine-2,4-dione | 456.0 |
| 3k | 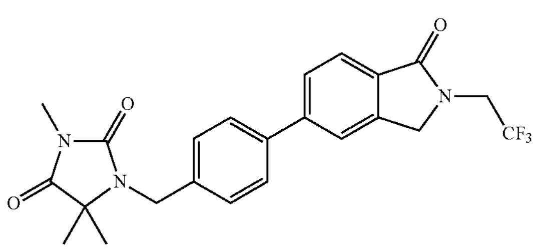 [SMILES: CN1C(=O)N(Cc2ccc(-c3ccc4c(c3)CN(CC(F)(F)F)C4=O)cc2)C(C)(C)C1=O] | 3,5,5-trimethyl-1-(4-(1-oxo-2-(2,2,2-trifluoroethyl)isoindolin-5-yl)benzyl)imidazolidine-2,4-dione | 446.0 |

-continued

| Ex. | Structure | Name | M/S |
|---|---|---|---|
| 3l | 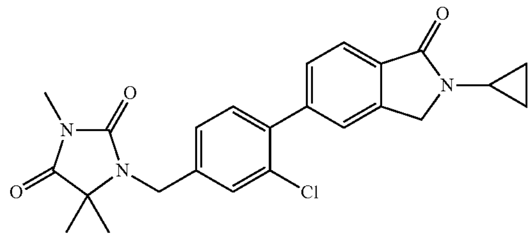 [SMILES: CN1C(=O)N(Cc2ccc(-c3ccc4c(c3)CN(C3CC3)C4=O)c(Cl)c2)C(C)(C)C1=O] | 1-(3-chloro-4-(2-cyclopropyl-1-oxoisoindolin-5-yl)benzyl)-3,5,5-trimethylimidazolidine-2,4-dione | 438.0 |
| 3m | 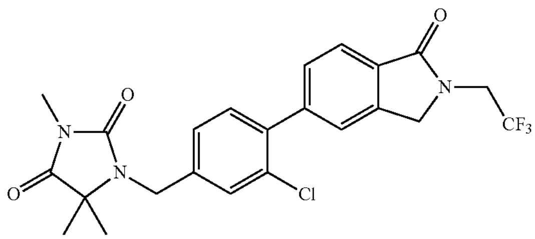 [SMILES: CN1C(=O)N(Cc2ccc(-c3ccc4c(c3)CN(CC(F)(F)F)C4=O)c(Cl)c2)C(C)(C)C1=O] | 1-(3-chloro-4-(1-oxo-2-(2,2,2-trifluoroethyl)isoindolin-5-yl)benzyl)-3,5,5-trimethylimidazolidine-2,4-dione | 480.0 |
| 3n | 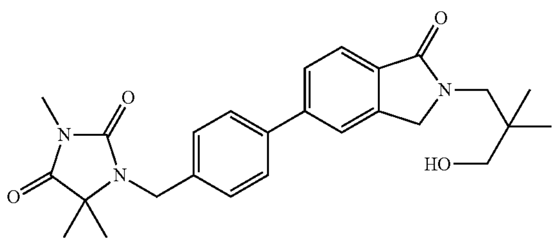 [SMILES: CN1C(=O)N(Cc2ccc(-c3ccc4c(c3)CN(CC(C)(C)CO)C4=O)cc2)C(C)(C)C1=O] | 1-(4-(2-(3-hydroxy-2,2-dimethylpropyl)-1-oxoisoindolin-5-yl)benzyl)-3,5,5-trimethylimidazolidine-2,4-dione | 450.2 |
| 3o | 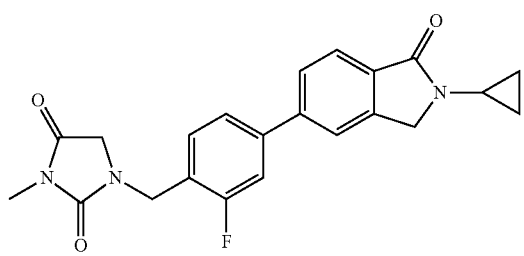 [SMILES: CN1C(=O)CN(Cc2ccc(-c3ccc4c(c3)CN(C3CC3)C4=O)cc2F)C1=O] | 1-(4-(2-cyclopropyl-1-oxoisoindolin-5-yl)-2-fluorobenzyl)-3-methylimidazolidine-2,4-dione | 394.0 |
| 3p | 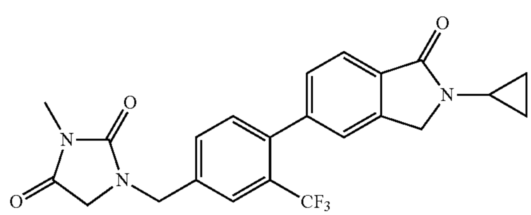 [SMILES: CN1C(=O)CN(Cc2ccc(-c3ccc4c(c3)CN(C3CC3)C4=O)c(C(F)(F)F)c2)C1=O] | 1-(4-(2-cyclopropyl-1-oxoisoindolin-5-yl)-3-(trifluoromethyl)benzyl)-3-methylimidazolidine-2,4-dione | 444.2 |
| 3q | 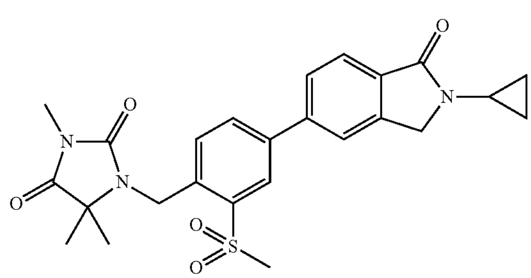 [SMILES: CN1C(=O)N(Cc2ccc(-c3ccc4c(c3)CN(C3CC3)C4=O)cc2S(C)(=O)=O)C(C)(C)C1=O] | 1-(4-(2-cyclopropyl-1-oxoisoindolin-5-yl)-2-(methylsulfonyl)benzyl)-3,5,5-trimethylimidazolidine-2,4-dione | 482.2 |

-continued

| Ex. | Structure | Name | M/S |
|---|---|---|---|
| 3r | 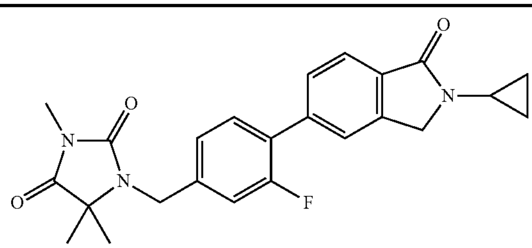 | 1-(4-(2-cyclopropyl-1-oxoisoindolin-5-yl)-3-fluorobenzyl)-3,5,5-trimethylimidazolidine-2,4-dione | 422.2 |
| 3s | 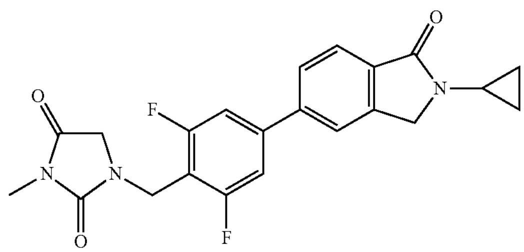 [SMILES: CN1C(=O)CN(Cc2c(F)cc(-c3ccc4c(c3)CN(C3CC3)C4=O)cc2F)C1=O] | 1-(4-(2-cyclopropyl-1-oxoisoindolin-5-yl)-2,6-difluorobenzyl)-3-methylimidazolidine-2,4-dione | 412.2 |

Example 4a 1-(4-(2-Isopropyl-1-oxoisoindolin-5-yl)benzyl)-3-methylimidazolidine-2,4-dione

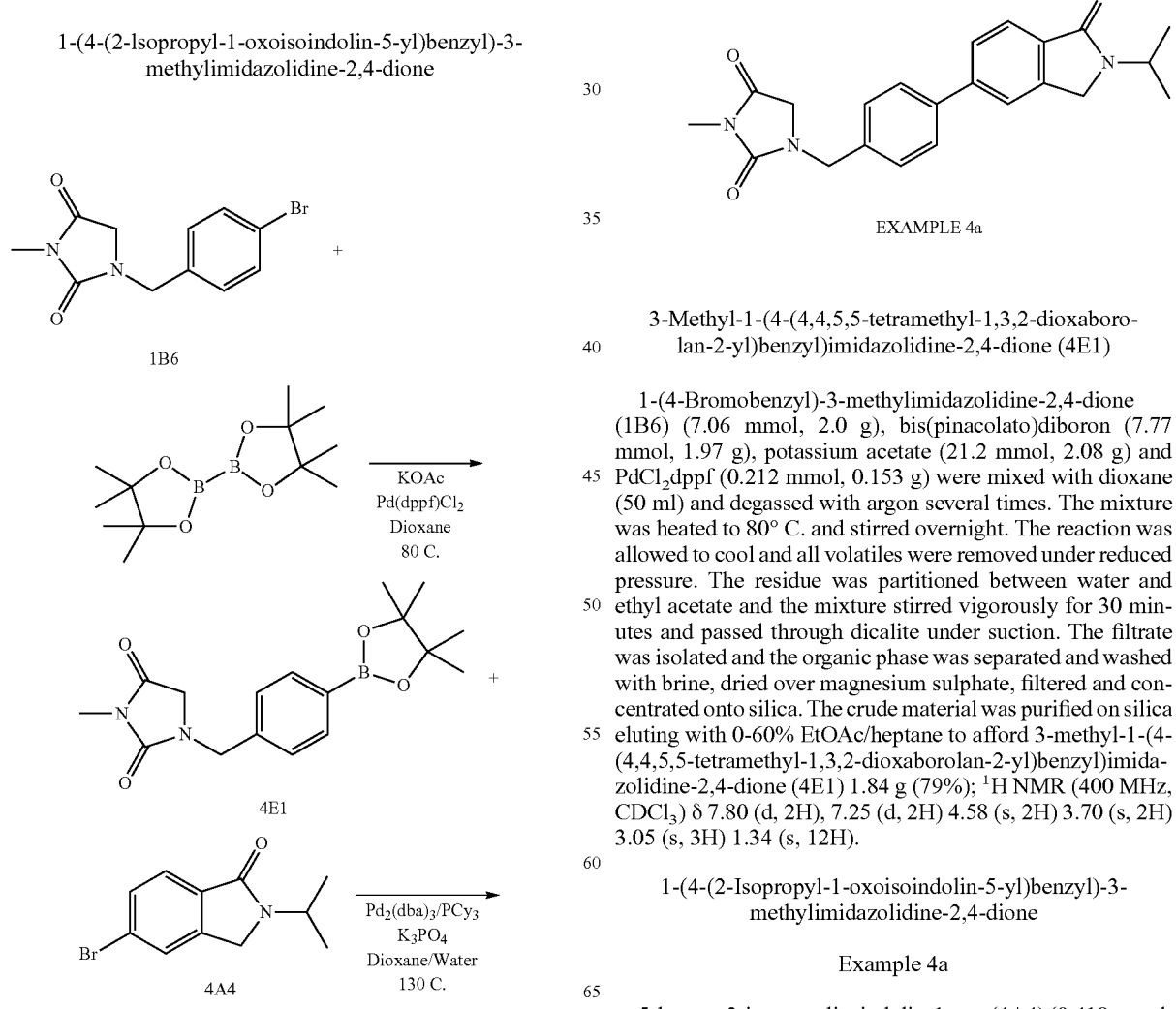

EXAMPLE 4a

3-Methyl-1-(4-(4,4,5,5-tetramethyl-1,3,2-dioxaborolan-2-yl)benzyl)imidazolidine-2,4-dione (4E1)

1-(4-Bromobenzyl)-3-methylimidazolidine-2,4-dione (1B6) (7.06 mmol, 2.0 g), bis(pinacolato)diboron (7.77 mmol, 1.97 g), potassium acetate (21.2 mmol, 2.08 g) and PdCl$_2$dppf (0.212 mmol, 0.153 g) were mixed with dioxane (50 ml) and degassed with argon several times. The mixture was heated to 80° C. and stirred overnight. The reaction was allowed to cool and all volatiles were removed under reduced pressure. The residue was partitioned between water and ethyl acetate and the mixture stirred vigorously for 30 minutes and passed through dicalite under suction. The filtrate was isolated and the organic phase was separated and washed with brine, dried over magnesium sulphate, filtered and concentrated onto silica. The crude material was purified on silica eluting with 0-60% EtOAc/heptane to afford 3-methyl-1-(4-(4,4,5,5-tetramethyl-1,3,2-dioxaborolan-2-yl)benzyl)imidazolidine-2,4-dione (4E1) 1.84 g (79%); $^1$H NMR (400 MHz, CDCl$_3$) δ 7.80 (d, 2H), 7.25 (d, 2H) 4.58 (s, 2H) 3.70 (s, 2H) 3.05 (s, 3H) 1.34 (s, 12H).

1-(4-(2-Isopropyl-1-oxoisoindolin-5-yl)benzyl)-3-methylimidazolidine-2,4-dione

Example 4a 5-bromo-2-isopropylisoindolin-1-one (4A4) (0.418 mmol, 106 mg) was mixed with 3-methyl-1-(4-(4,4,5,5-tetramethyl- 1,3,2-dioxaborolan-2-yl)benzyl)imidazolidine-2,4-dione (4E1) (0.418 mmol, 138 mg), tricyclohexylphosphine (0.050 mmol, 14 mg), tris(dibenzylidineacetone) dipalladium chloroform adduct (0.021 mmol, 22 mg) and potassium phosphate (0.710 mmol, 151 mg) in dioxane (2 ml) and water (1 ml). The mixture was heated to 130° C. for 15 minutes in the microwave before addition of DCM (2 ml) and water (2 ml). The reaction was stirred vigorously for 30 minutes before collection of the organic layer using a hydrophobic fritted tube followed by concentration. Purification was achieved using basic HPLC and the desired fractions concentrated to give 1-(4-(2-isopropyl-1-oxoisoindolin-5-yl)benzyl)-3-methylimidazolidine-2,4-dione (Example 4a) 49.2 mg (31.2%); $^1$H NMR (400 MHz, CDCl$_3$) δ 7.91 (d, 1H) 7.67-7.59 (m, 4H) 7.37 (d, 2H) 4.7 (sept, 1H) 4.62 (s, 2H) 4.4 (s, 2H) 3.79 (s, 2H) 3.07 (s, 3H) 1.31 (d, 6H) LCMS m/z (M+H) 378.2.

The following compounds were prepared in a similar way replacing one or both of 1B6 and 4A4 with equivalent reagents:

| Ex. | Structure | Name | M/S |
|---|---|---|---|
| 4b | 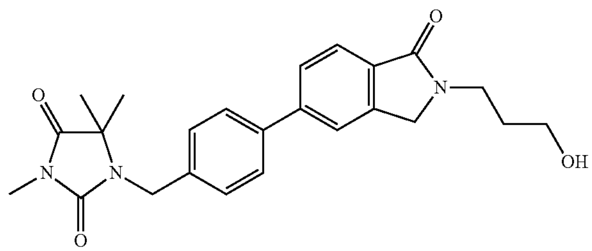 [SMILES: CN1C(=O)N(Cc2ccc(-c3ccc4c(c3)CN(CCCO)C4=O)cc2)C(C)(C)C1=O] | 1-(4-(2-(3-hydroxypropyl)-1-oxoisoindolin-5-yl)benzyl)-3,5,5-trimethylimidazolidine-2,4-dione | 422.2 |
| 4c | 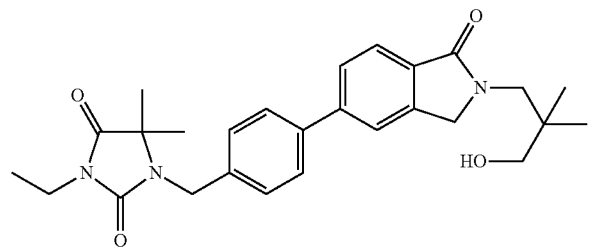 [SMILES: CCN1C(=O)N(Cc2ccc(-c3ccc4c(c3)CN(CC(C)(C)CO)C4=O)cc2)C(C)(C)C1=O] | 3-ethyl-1-(4-(2-(3-hydroxy-2,2-dimethylpropyl)-1-oxoisoindolin-5-yl)benzyl)-5,5-dimethylimidazolidine-2,4-dione | 464.2 |
| 4d | 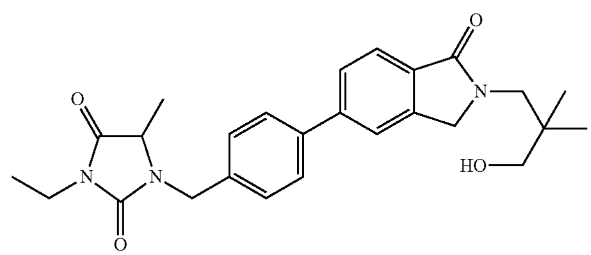 [SMILES: CCN1C(=O)C(C)N(Cc2ccc(-c3ccc4c(c3)CN(CC(C)(C)CO)C4=O)cc2)C1=O] | 3-ethyl-1-(4-(2-(3-hydroxy-2,2-dimethylpropyl)-1-oxoisoindolin-5-yl)benzyl)-5-methylimidazolidine-2,4-dione | 450.2 |
| 4e | 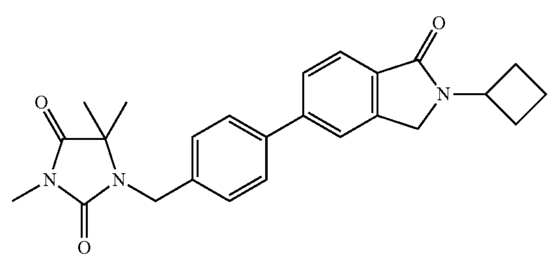 [SMILES: CN1C(=O)N(Cc2ccc(-c3ccc4c(c3)CN(C3CCC3)C4=O)cc2)C(C)(C)C1=O] | 1-(4-(2-cyclobutyl-1-oxoisoindolin-5-yl)benzyl)-3,5,5-trimethylimidazolidine-2,4-dione | 418.2 |
| 4f | 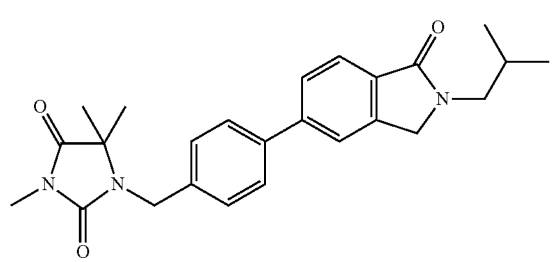 [SMILES: CC(C)CN1Cc2cc(-c3ccc(CN4C(=O)N(C)C(=O)C4(C)C)cc3)ccc2C1=O] | 1-(4-(2-isobutyl-1-oxoisoindolin-5-yl)benzyl)-3,5,5-trimethylimidazolidine-2,4-dione | 420.2 |

-continued

| Ex. | Structure | Name | M/S |
|---|---|---|---|
| 4g | 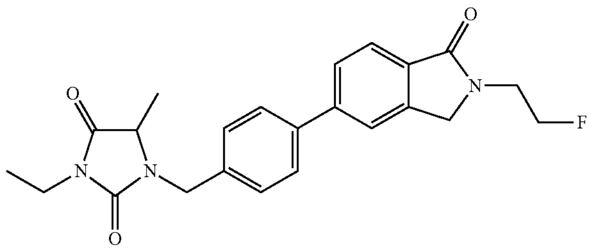 [SMILES: CCN1C(=O)C(C)N(Cc2ccc(-c3ccc4c(c3)CN(CCF)C4=O)cc2)C1=O] | 3-ethyl-1-(4-(2-(2-fluoroethyl)-1-oxoisoindolin-5-yl)benzyl)-5-methylimidazolidine-2,4-dione | 410.2 |
| 4h | 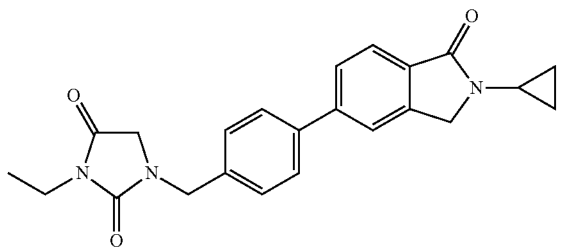 [SMILES: CCN1C(=O)CN(Cc2ccc(-c3ccc4c(c3)CN(C3CC3)C4=O)cc2)C1=O] | 1-(4-(2-cyclopropyl-1-oxoisoindolin-5-yl)benzyl)-3-ethylimidazolidine-2,4-dione | 390.2 |
| 4i | 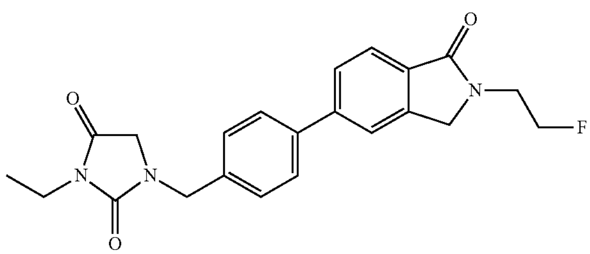 [SMILES: CCN1C(=O)CN(Cc2ccc(-c3ccc4c(c3)CN(CCF)C4=O)cc2)C1=O] | 3-ethyl-1-(4-(2-(2-fluoroethyl)-1-oxoisoindolin-5-yl)benzyl)imidazolidine-2,4-dione | 396.0 |
| 4j | 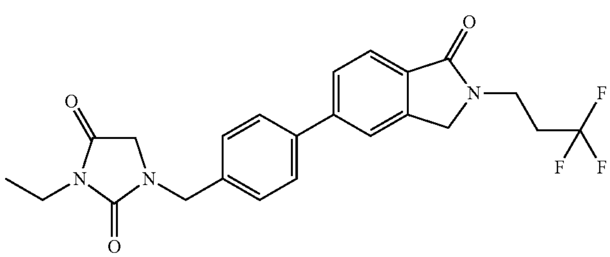 [SMILES: CCN1C(=O)CN(Cc2ccc(-c3ccc4c(c3)CN(CCC(F)(F)F)C4=O)cc2)C1=O] | 3-ethyl-1-(4-(1-oxo-2-(3,3,3-trifluoropropyl)isoindolin-5-yl)benzyl)imidazolidine-2,4-dione | 446.2 |
| 4k | 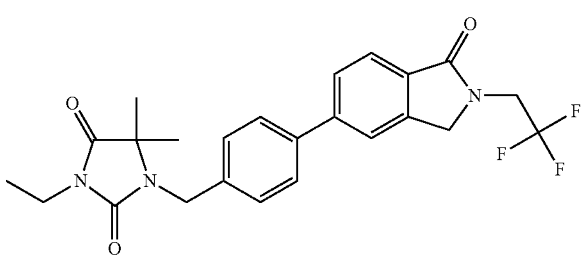 [SMILES: CCN1C(=O)N(Cc2ccc(-c3ccc4c(c3)CN(CC(F)(F)F)C4=O)cc2)C(C)(C)C1=O] | 3-ethyl-5,5-dimethyl-1-(4-(1-oxo-2-(2,2,2-trifluoroethyl)isoindolin-5-yl)benzyl)imidazolidine-2,4-dione | 460.0 |
| 4l | 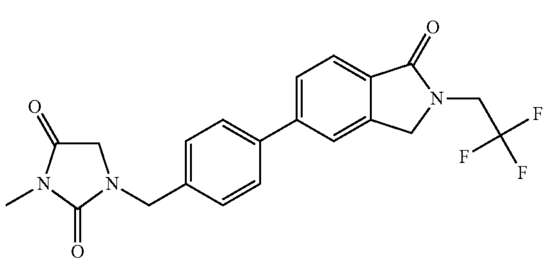 [SMILES: CN1C(=O)CN(Cc2ccc(-c3ccc4c(c3)CN(CC(F)(F)F)C4=O)cc2)C1=O] | 3-methyl-1-(4-(1-oxo-2-(2,2,2-trifluoroethyl)isoindolin-5-yl)benzyl)imidazolidine-2,4-dione | 418.0 |

-continued

| Ex. | Structure | Name | M/S |
|---|---|---|---|
| 4m | 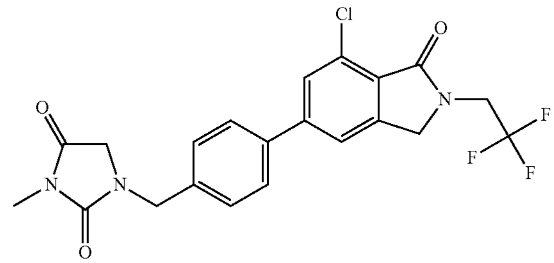 [SMILES: CN1C(=O)CN(Cc2ccc(-c3cc(Cl)c4c(c3)CN(CC(F)(F)F)C4=O)cc2)C1=O] | 1-(4-(7-chloro-1-oxo-2-(2,2,2-trifluoroethyl)isoindolin-5-yl)benzyl)-3-methylimidazolidine-2,4-dione | 452.0 |
| 4n | 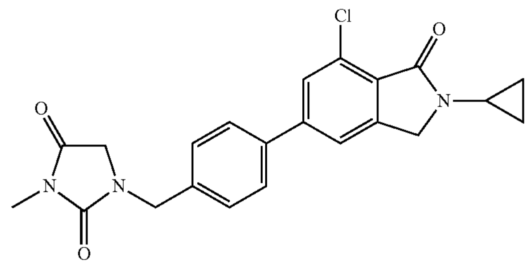 [SMILES: CN1C(=O)CN(Cc2ccc(-c3cc(Cl)c4c(c3)CN(C3CC3)C4=O)cc2)C1=O] | 1-(4-(7-chloro-2-cyclopropyl-1-oxoisoindolin-5-yl)benzyl)-3-methylimidazolidine-2,4-dione | 410.0 |
| 4o | 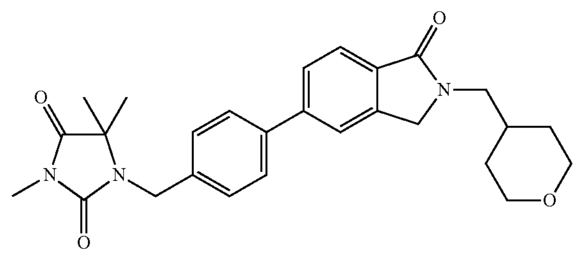 [SMILES: CN1C(=O)N(Cc2ccc(-c3ccc4c(c3)CN(CC3CCOCC3)C4=O)cc2)C(C)(C)C1=O] | 3,5,5-trimethyl-1-(4-(1-oxo-2-((tetrahydro-2H-pyran-4-yl)methyl)isoindolin-5-yl)benzyl)imidazolidine-2,4-dione | 462.2 |
| 4p | 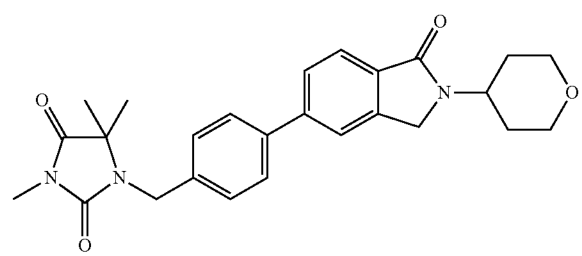 [SMILES: CN1C(=O)N(Cc2ccc(-c3ccc4c(c3)CN(C3CCOCC3)C4=O)cc2)C(C)(C)C1=O] | 3,5,5-trimethyl-1-(4-(1-oxo-2-(tetrahydro-2H-pyran-4-yl)isoindolin-5-yl)benzyl)imidazolidine-2,4-dione | 448.2 |
| 4q | 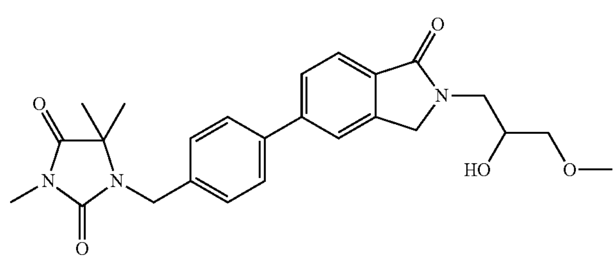 | 1-(4-(2-(2-hydroxy-3-methoxypropyl)-1-oxoisoindolin-5-yl)benzyl)-3,5,5-trimethylimidazolidine-2,4-dione | 452.2 |
| 4r | 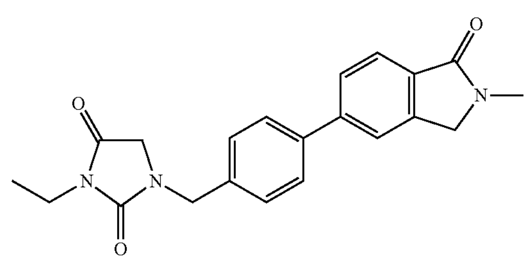 [SMILES: CCN1C(=O)CN(Cc2ccc(-c3ccc4c(c3)CN(C)C4=O)cc2)C1=O] | 3-ethyl-1-(4-(2-methyl-1-oxoisoindolin-5-yl)benzyl)imidazolidine-2,4-dione | 364.2 |

| Ex. | Structure | Name | M/S |
|---|---|---|---|
| 4s | 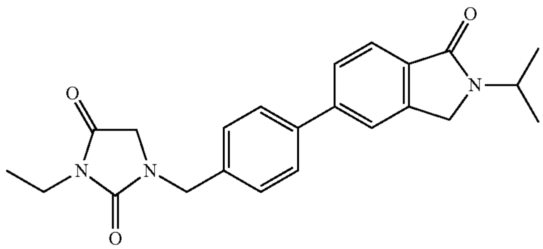 [SMILES: CCN1C(=O)CN(Cc2ccc(-c3ccc4c(c3)CN(C(C)C)C4=O)cc2)C1=O] | 3-ethyl-1-(4-(2-isopropyl-1-oxoisoindolin-5-yl)benzyl)imidazolidine-2,4-dione | 392.2 |
| 4t | 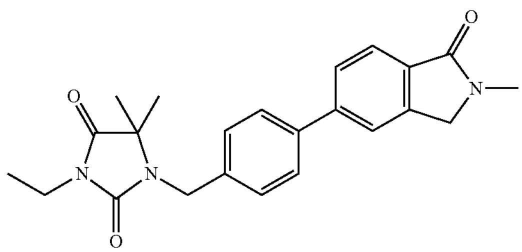 [SMILES: CCN1C(=O)N(Cc2ccc(-c3ccc4c(c3)CN(C)C4=O)cc2)C(C)(C)C1=O] | 3-ethyl-5,5-dimethyl-1-(4-(2-methyl-1-oxoisoindolin-5-yl)benzyl)imidazolidine-2,4-dione | 392.2 |
| 4u | 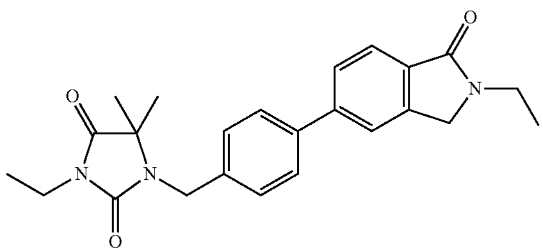 [SMILES: CCN1Cc2cc(-c3ccc(CN4C(=O)N(CC)C(=O)C4(C)C)cc3)ccc2C1=O] | 3-ethyl-1-(4-(2-ethyl-1-oxoisoindolin-5-yl)benzyl)-5,5-dimethylimidazolidine-2,4-dione | 406.2 |
| 4v | 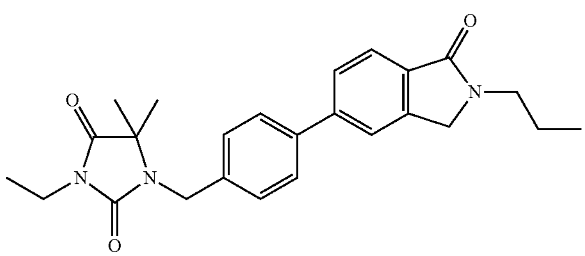 [SMILES: CCCN1Cc2cc(-c3ccc(CN4C(=O)N(CC)C(=O)C4(C)C)cc3)ccc2C1=O] | 3-ethyl-5,5-dimethyl-1-(4-(1-oxo-2-propylisoindolin-5-yl)benzyl)imidazolidine-2,4-dione | 420.2 |
| 4w | 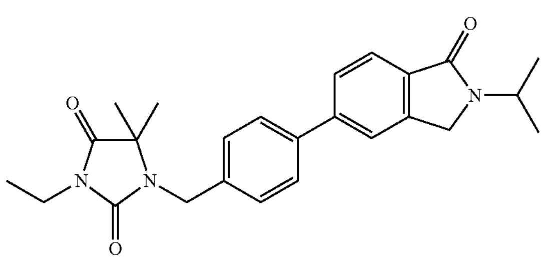 [SMILES: CCN1C(=O)N(Cc2ccc(-c3ccc4c(c3)CN(C(C)C)C4=O)cc2)C(C)(C)C1=O] | 3-ethyl-1-(4-(2-isopropyl-1-oxoisoindolin-5-yl)benzyl)-5,5-dimethylimidazolidine-2,4-dione | 420.2 |
| 4x | 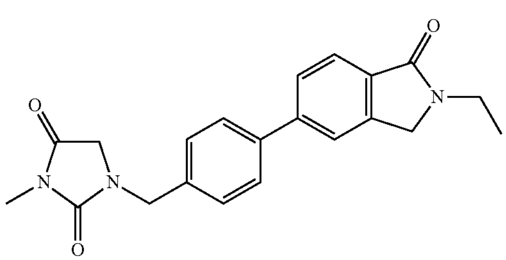 [SMILES: CCN1Cc2cc(-c3ccc(CN4CC(=O)N(C)C4=O)cc3)ccc2C1=O] | 1-(4-(2-ethyl-1-oxoisoindolin-5-yl)benzyl)-3-methylimidazolidine-2,4-dione | 364.2 |

| Ex. | Structure | Name | M/S |
|---|---|---|---|
| 4y | 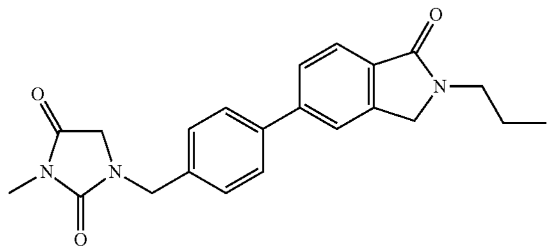 [SMILES: CCCN1Cc2cc(-c3ccc(CN4CC(=O)N(C)C4=O)cc3)ccc2C1=O] | 3-methyl-1-(4-(1-oxo-2-propylisoindolin-5-yl)benzyl)imidazolidine-2,4-dione | 378.2 |
| 4z | 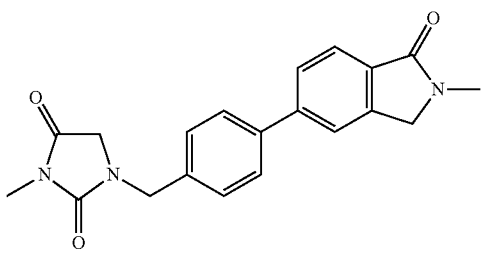 | 3-methyl-1-(4-(2-methyl-1-oxoisoindolin-5-yl)benzyl)imidazolidine-2,4-dione | 350.2 |
| 4aa | 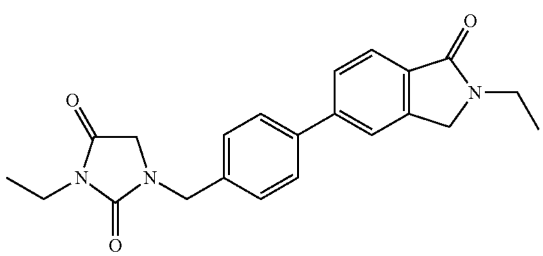 [SMILES: CCN1Cc2cc(-c3ccc(CN4CC(=O)N(CC)C4=O)cc3)ccc2C1=O] | 3-ethyl-1-(4-(2-ethyl-1-oxoisoindolin-5-yl)benzyl)imidazolidine-2,4-dione | 378.2 |
| 4ab | 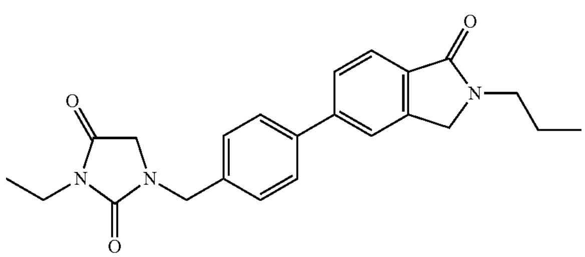 [SMILES: CCCN1Cc2cc(-c3ccc(CN4CC(=O)N(CC)C4=O)cc3)ccc2C1=O] | 3-ethyl-1-(4-(1-oxo-2-propylisoindolin-5-yl)benzyl)imidazolidine-2,4-dione | 392.2 |
| 4ac | 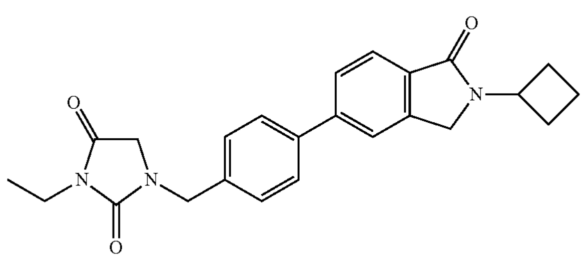 [SMILES: CCN1C(=O)CN(Cc2ccc(-c3ccc4c(c3)CN(C3CCC3)C4=O)cc2)C1=O] | 1-(4-(2-cyclobutyl-1-oxoisoindolin-5-yl)benzyl)-3-ethylimidazolidine-2,4-dione | 404.2 |
| 4ad | 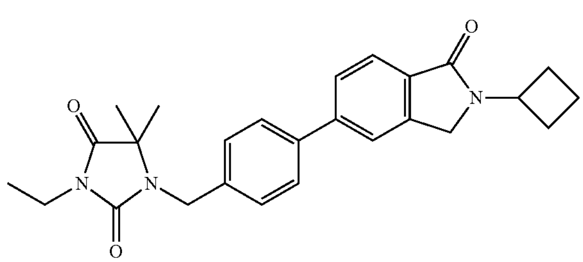 [SMILES: CCN1C(=O)N(Cc2ccc(-c3ccc4c(c3)CN(C3CCC3)C4=O)cc2)C(C)(C)C1=O] | 1-(4-(2-cyclobutyl-1-oxoisoindolin-5-yl)benzyl)-3-ethyl-5,5-dimethylimidazolidine-2,4-dione | 432.2 |

-continued

| Ex. | Structure | Name | M/S |
|---|---|---|---|
| 4ae | 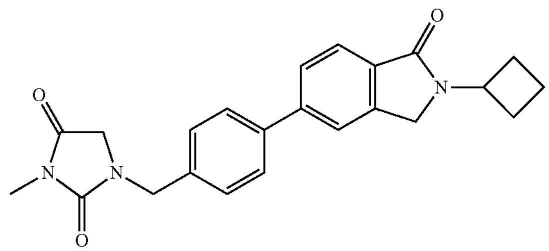 [SMILES: CN1C(=O)CN(Cc2ccc(-c3ccc4c(c3)CN(C3CCC3)C4=O)cc2)C1=O] | 1-(4-(2-cyclobutyl-1-oxoisoindolin-5-yl)benzyl)-3-methylimidazolidine-2,4-dione | 390.2 |
| 4af | 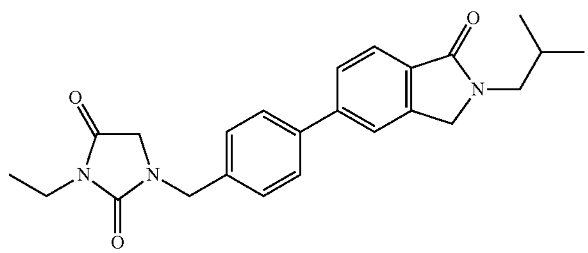 [SMILES: CCN1C(=O)CN(Cc2ccc(-c3ccc4c(c3)CN(CC(C)C)C4=O)cc2)C1=O] | 3-ethyl-1-(4-(2-isobutyl-1-oxoisoindolin-5-yl)benzyl)imidazolidine-2,4-dione | 406.2 |
| 4ag | 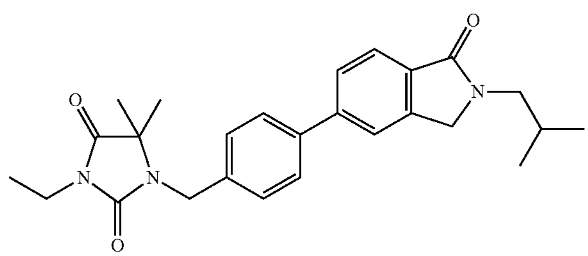 [SMILES: CCN1C(=O)N(Cc2ccc(-c3ccc4c(c3)CN(CC(C)C)C4=O)cc2)C(C)(C)C1=O] | 3-ethyl-1-(4-(2-isobutyl-1-oxoisoindolin-5-yl)benzyl)-5,5-dimethylimidazolidine-2,4-dione | 434.2 |
| 4ah | 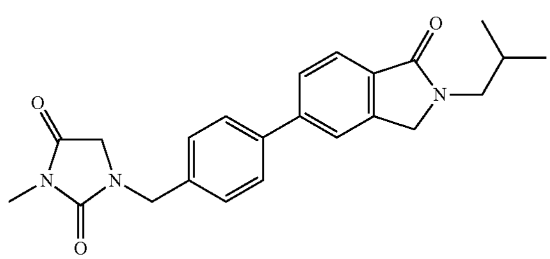 [SMILES: CC(C)CN1Cc2cc(-c3ccc(CN4CC(=O)N(C)C4=O)cc3)ccc2C1=O] | 1-(4-(2-isobutyl-1-oxoisoindolin-5-yl)benzyl)-3-methylimidazolidine-2,4-dione | 392.2 |
| 4ai | 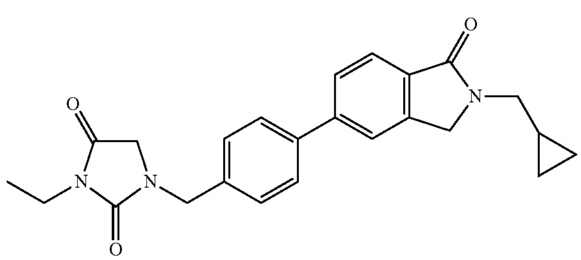 [SMILES: CCN1C(=O)CN(Cc2ccc(-c3ccc4c(c3)CN(CC3CC3)C4=O)cc2)C1=O] | 1-(4-(2-(cyclopropylmethyl)-1-oxoisoindolin-5-yl)benzyl)-3-ethylimidazolidine-2,4-dione | 404.2 |
| 4aj | 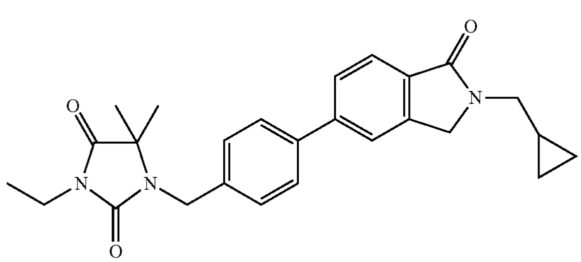 [SMILES: CCN1C(=O)N(Cc2ccc(-c3ccc4c(c3)CN(CC3CC3)C4=O)cc2)C(C)(C)C1=O] | 1-(4-(2-(cyclopropylmethyl)-1-oxoisoindolin-5-yl)benzyl)-3-ethyl-5,5-dimethylimidazolidine-2,4-dione | 432.2 |

-continued

| Ex. | Structure | Name | M/S |
|---|---|---|---|
| 4ak | 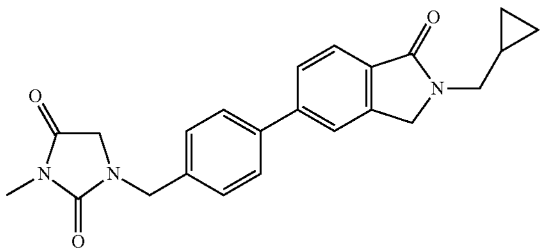 [SMILES: CN1C(=O)CN(Cc2ccc(-c3ccc4c(c3)CN(CC3CC3)C4=O)cc2)C1=O] | 1-(4-(2-(cyclopropylmethyl)-1-oxoisoindolin-5-yl)benzyl)-3-methylimidazolidine-2,4-dione | 390.2 |
| 4al | 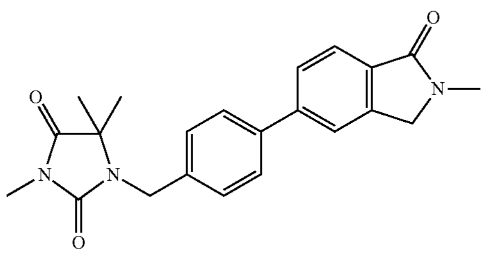 | 3,5,5-trimethyl-1-(4-(2-methyl-1-oxoisoindolin-5-yl)benzyl)imidazolidine-2,4-dione | 378.2 |
| 4am | 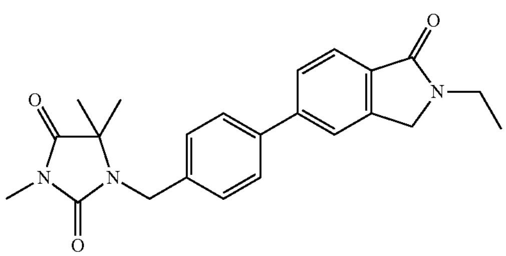 [SMILES: CCN1Cc2cc(-c3ccc(CN4C(=O)N(C)C(=O)C4(C)C)cc3)ccc2C1=O] | 1-(4-(2-ethyl-1-oxoisoindolin-5-yl)benzyl)-3,5,5-trimethylimidazolidine-2,4-dione | 392.2 |
| 4an | 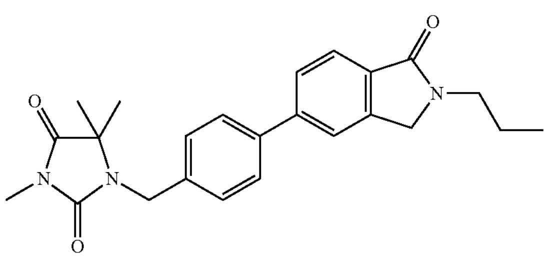 [SMILES: CCCN1Cc2cc(-c3ccc(CN4C(=O)N(C)C(=O)C4(C)C)cc3)ccc2C1=O] | 3,5,5-trimethyl-1-(4-(1-oxo-2-propylisoindolin-5-yl)benzyl)imidazolidine-2,4-dione | 406.2 |
| 4ao | 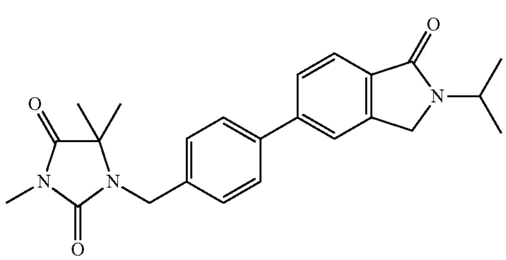 [SMILES: CC(C)N1Cc2cc(-c3ccc(CN4C(=O)N(C)C(=O)C4(C)C)cc3)ccc2C1=O] | 1-(4-(2-isopropyl-1-oxoisoindolin-5-yl)benzyl)-3,5,5-trimethylimidazolidine-2,4-dione | 406.2 |
| 4ap | 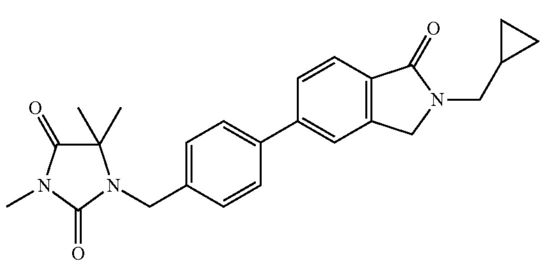 [SMILES: CN1C(=O)N(Cc2ccc(-c3ccc4c(c3)CN(CC3CC3)C4=O)cc2)C(C)(C)C1=O] | 1-(4-(2-(cyclopropylmethyl)-1-oxoisoindolin-5-yl)benzyl)-3,5,5-trimethylimidazolidine-2,4-dione | 418.2 |

| Ex. | Structure | Name | M/S |
|---|---|---|---|
| 4aq | 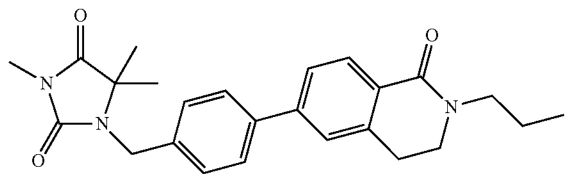 [SMILES: CCCN1CCc2cc(-c3ccc(CN4C(=O)N(C)C(=O)C4(C)C)cc3)ccc2C1=O] | 3,5,5-trimethyl-1-(4-(1-oxo-2-propyl-1,2,3,4-tetrahydroisoquinolin-6-yl)benzyl)imidazolidine-2,4-dione | 462.2 |
| 4ar | 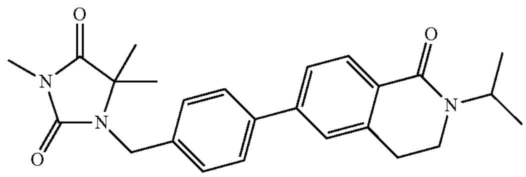 [SMILES: CC(C)N1CCc2cc(-c3ccc(CN4C(=O)N(C)C(=O)C4(C)C)cc3)ccc2C1=O] | 1-(4-(2-isopropyl-1-oxo-1,2,3,4-tetrahydroisoquinolin-6-yl)benzyl)-3,5,5-trimethylimidazolidine-2,4-dione | 448.2 |
| 4as | 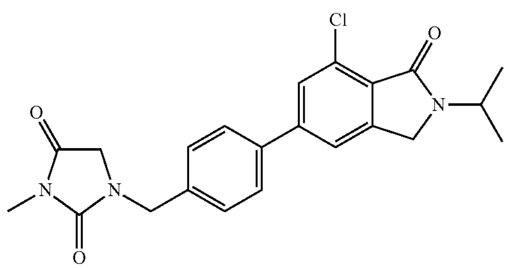 [SMILES: CC(C)N1Cc2cc(-c3ccc(CN4CC(=O)N(C)C4=O)cc3)cc(Cl)c2C1=O] | 1-(4-(7-chloro-2-isopropyl-1-oxoisoindolin-5-yl)benzyl)-3-methylimidazolidine-2,4-dione | 412.0 |
| 4at | 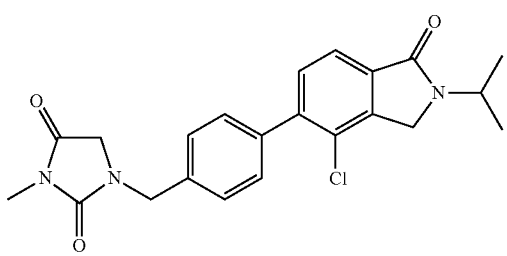 [SMILES: CC(C)N1Cc2c(ccc(-c3ccc(CN4CC(=O)N(C)C4=O)cc3)c2Cl)C1=O] | 1-(4-(4-chloro-2-isopropyl-1-oxoisoindolin-5-yl)benzyl)-3-methylimidazolidine-2,4-dione | 412.0 |
| 4au | 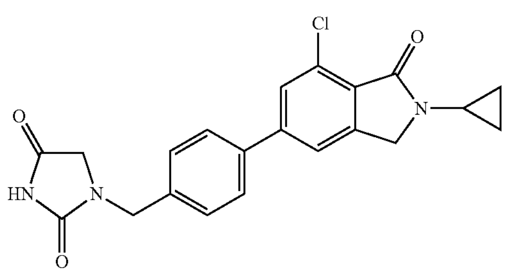 [SMILES: O=C1CN(Cc2ccc(-c3cc(Cl)c4c(c3)CN(C3CC3)C4=O)cc2)C(=O)N1] | 1-(4-(7-chloro-2-cyclopropyl-1-oxoisoindolin-5-yl)benzyl)imidazolidine-2,4-dione | 396.0 |
| 4av | 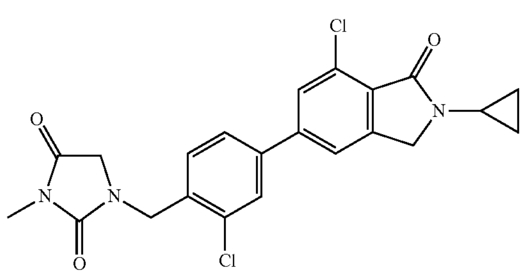 [SMILES: CN1C(=O)CN(Cc2ccc(-c3cc(Cl)c4c(c3)CN(C3CC3)C4=O)cc2Cl)C1=O] | 1-(2-chloro-4-(7-chloro-2-cyclopropyl-1-oxoisoindolin-5-yl)benzyl)-3-methylimidazolidine-2,4-dione | 446.0 |

| Ex. | Structure | Name | M/S |
|---|---|---|---|
| 4aw | 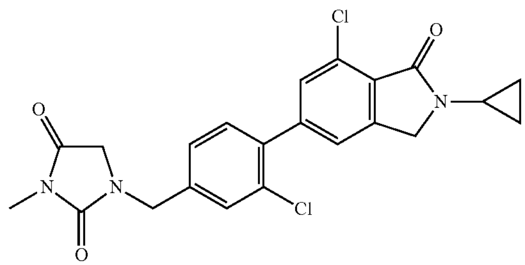 [SMILES: CN1C(=O)CN(Cc2ccc(-c3cc(Cl)c4c(c3)CN(C3CC3)C4=O)c(Cl)c2)C1=O] | 1-(3-chloro-4-(7-chloro-2-cyclopropyl-1-oxoisoindolin-5-yl)benzyl)-3-methylimidazolidine-2,4-dione | 446.0 |
| 4ax | 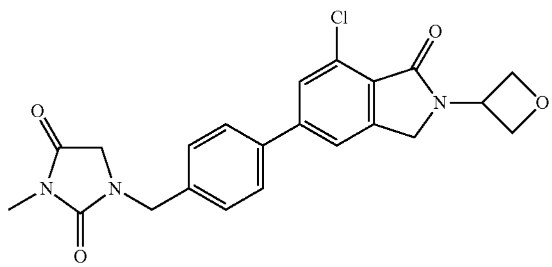 [SMILES: CN1C(=O)CN(Cc2ccc(-c3cc(Cl)c4c(c3)CN(C3COC3)C4=O)cc2)C1=O] | 1-(4-(7-chloro-2-(oxetan-3-yl)-1-oxoisoindolin-5-yl)benzyl)-3-methylimidazolidine-2,4-dione | 426.0 |
| 4ay | 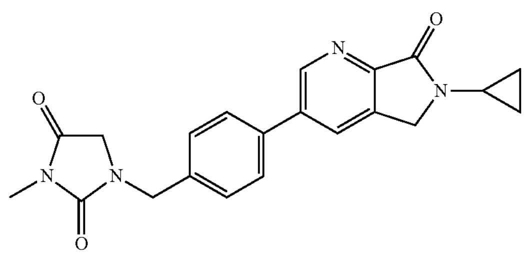 [SMILES: CN1C(=O)CN(Cc2ccc(-c3cnc4c(c3)CN(C3CC3)C4=O)cc2)C1=O] | 1-(4-(6-cyclopropyl-7-oxo-6,7-dihydro-5H-pyrrolo[3,4-b]pyridin-3-yl)benzyl)-3-methylimidazolidine-2,4-dione | 377.2 |
| 4az | 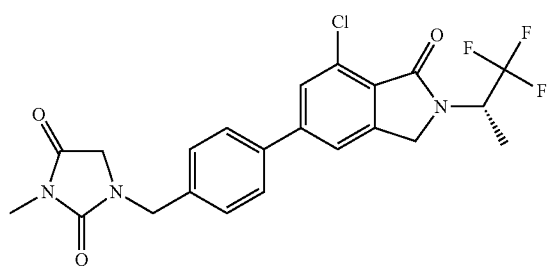 [SMILES: C[C@H](N1Cc2cc(-c3ccc(CN4CC(=O)N(C)C4=O)cc3)cc(Cl)c2C1=O)C(F)(F)F] | (S)-1-(4-(7-chloro-1-oxo-2-(1,1,1-trifluoropropan-2-yl)isoindolin-5-yl)benzyl)-3-methylimidazolidine-2,4-dione | 466.0 |
| 4ba | 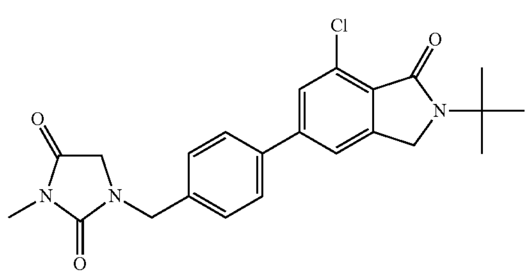 [SMILES: CN1C(=O)CN(Cc2ccc(-c3cc(Cl)c4c(c3)CN(C(C)(C)C)C4=O)cc2)C1=O] | 1-(4-(2-tert-butyl-7-chloro-1-oxoisoindolin-5-yl)benzyl)-3-methylimidazolidine-2,4-dione | 426.2 |
| 4bb | 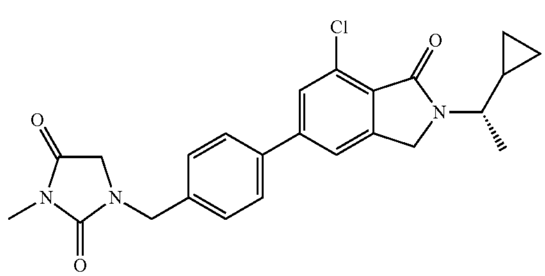 [SMILES: C[C@@H](C1CC1)N1Cc2cc(-c3ccc(CN4CC(=O)N(C)C4=O)cc3)cc(Cl)c2C1=O] | (S)-1-(4-(7-chloro-2-(1-cyclopropylethyl)-1-oxoisoindolin-5-yl)benzyl)-3-methylimidazolidine-2,4-dione | 438.2 |

-continued

| Ex. | Structure | Name | M/S |
|---|---|---|---|
| 4bc | 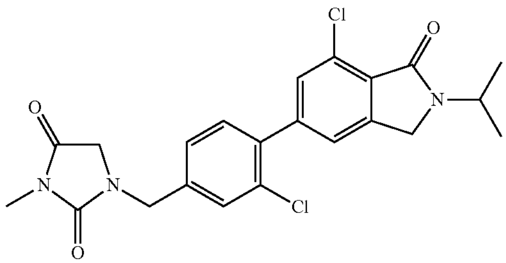 [SMILES: CC(C)N1Cc2cc(-c3ccc(CN4CC(=O)N(C)C4=O)cc3Cl)cc(Cl)c2C1=O] | 1-(3-chloro-4-(7-chloro-2-isopropyl-1-oxoisoindolin-5-yl)benzyl)-3-methylimidazolidine-2,4-dione | 448.0 |
| 4bd | 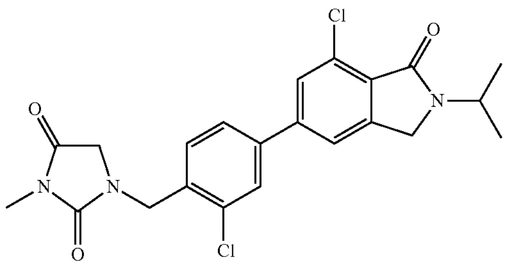 [SMILES: CC(C)N1Cc2cc(-c3ccc(CN4CC(=O)N(C)C4=O)c(Cl)c3)cc(Cl)c2C1=O] | 1-(2-chloro-4-(7-chloro-2-isopropyl-1-oxoisoindolin-5-yl)benzyl)-3-methylimidazolidine-2,4-dione | 448.0 |
| 4be | 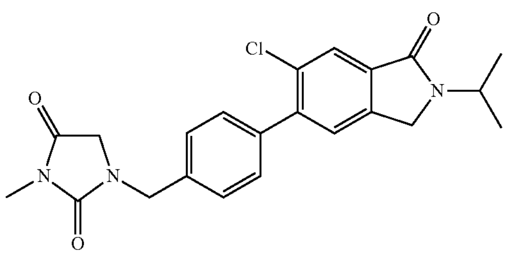 [SMILES: CC(C)N1Cc2cc(-c3ccc(CN4CC(=O)N(C)C4=O)cc3)c(Cl)cc2C1=O] | 1-(4-(6-chloro-2-isopropyl-1-oxoisoindolin-5-yl)benzyl)-3-methylimidazolidine-2,4-dione | 412.0 |
| 4bf | 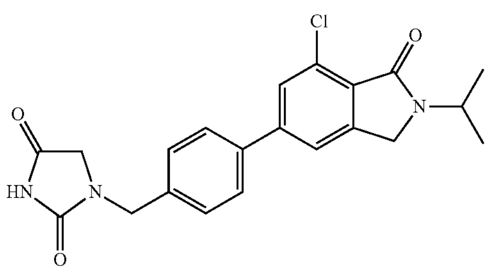 [SMILES: CC(C)N1Cc2cc(-c3ccc(CN4CC(=O)NC4=O)cc3)cc(Cl)c2C1=O] | 1-(4-(7-chloro-2-isopropyl-1-oxoisoindolin-5-yl)benzyl)imidazolidine-2,4-dione | 398.0 |
| 4bg | 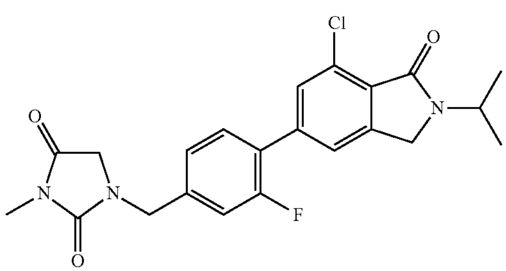 [SMILES: CC(C)N1Cc2cc(-c3ccc(CN4CC(=O)N(C)C4=O)cc3F)cc(Cl)c2C1=O] | 1-(4-(7-chloro-2-isopropyl-1-oxoisoindolin-5-yl)-3-fluorobenzyl)-3-methylimidazolidine-2,4-dione | 430.0 |
| 4bh | 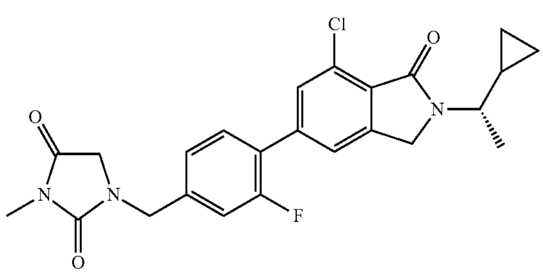 [SMILES: C[C@@H](C1CC1)N1Cc2cc(-c3ccc(CN4CC(=O)N(C)C4=O)cc3F)cc(Cl)c2C1=O] | (S)-1-(4-(7-chloro-2-(1-cyclopropylethyl)-1-oxoisoindolin-5-yl)-3-fluorobenzyl)-3-methylimidazolidine-2,4-dione | 456.2 |

Example 5a

(R)-3-(4-(2-Cyclopropyl-1-oxoisoindolin-5-yl)benzyl)-5-methyloxazolidin-2-one

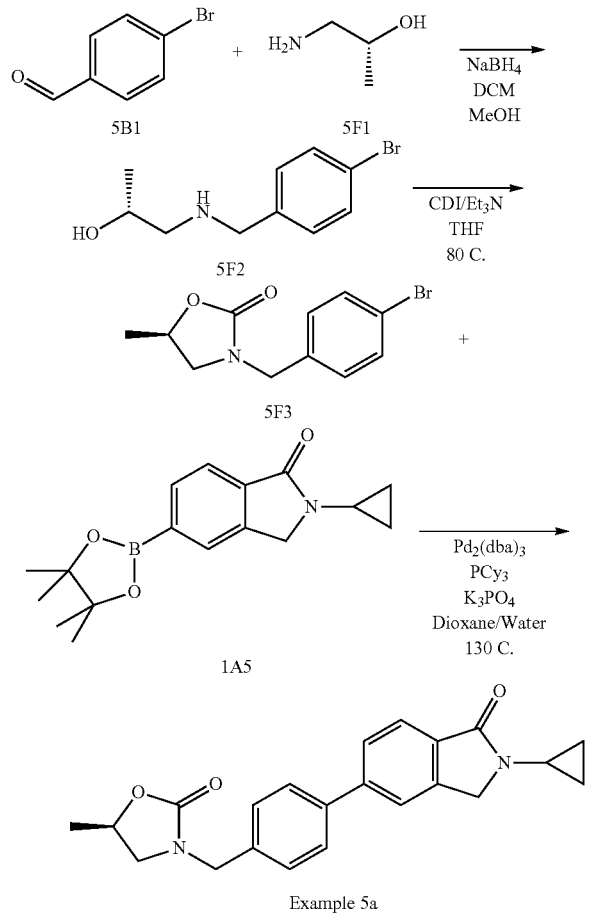

(R)-1-(4-Bromobenzylamino)propan-2-ol (5F2)

Bromobenzaldehyde (5B1) (0.027 mol, 5.0 g), (R)-1-aminopropan-2-ol (5F1) (0.027 mol, 2.02 g) and magnesium sulphate (0.05 mol, 6.0 g) were dissolved/suspended in DCM (60 ml) and methanol (40 ml) and stirred at room temperature overnight. The reaction mixture was filtered through a celite plug and washed with water before addition of sodium borohydride (0.054 mol, 2.05 g). The reaction was stirred for 30 min, concentrated under reduced pressure and the residue dissolved in water and extracted three times with EtOAc. The combined organic layers were washed with water and brine then dried over sodium sulphate, filtered and concentrated under reduced pressure to afford (R)-1-(4-bromobenzylamino)propan-2-ol (5F2) 6.1 g (92%); m/z (M+H) 246.0.

(R)-3-(4-Bromobenzyl)-5-methyloxazolidin-2-one (5F3)

(R)-1-(4-bromobenzylamino)propan-2-ol (5F2) (0.034 mol, 8.2 g) was dissolved in THF (150 ml) and triethylamine (0.051 mol, 5.12 g) was added, followed by carbonyldiimidazole (0.037 mol, 6.0 g). The mixture was stirred at room temperature for 2 hours then heated to reflux for 20 hours. The reaction mixture was diluted with water and extracted three times with EtOAc. The combined organics were washed with water and brine before drying over sodium sulphate. The crude mixture was purified on silica eluting with 35% EtOAc/Petroleum Ether to give (R)-3-(4-bromobenzyl)-5-methyloxazolidin-2-one (5F3) 6.7 g (74%); $^1$H NMR (400 MHz, CDCl$_3$) δ 7.48 (d, 2H) 7.16 (d, 2H) 4.62 (m, 1H) 4.41-4.32 (m, 2H) 3.49 (m, 1H) 2.95 (m, 1H) 1.39 (d, 3H).

(R)-3-(4-(2-Cyclopropyl-1-oxoisoindolin-5-yl)benzyl)-5-methyloxazolid in-2-one

Example 5a

2-Cyclopropyl-5-(4,4,5,5-tetramethyl-1,3,2-dioxaborolan-2-yl)isoindolin-1-one (1A5) (0.204 mmol, 60.9 mg) was mixed with (R)-3-(4-bromobenzyl)-5-methyloxazolidin-2-one (5F3) (0.185 mmol, 50 mg), tricyclohexylphosphine (0.022 mmol, 8.5 mg), tris(dibenzylidineacetone) dipalladium (0.009 mmol, 8.5 mg) and potassium phosphate (0.315 mmol, 66.7 mg) in dioxane (1ml) and water (0.5 ml). The mixture was heated to 130° C. for 10 minutes in the microwave before addition of DCM (3 ml) and water (2 ml). The phases were mixed and the organic phase collected using a hydrophobic fritted tube and concentrated under reduced pressure. Purification was achieved using basic HPLC to afford (R)-3-(4-(2-cyclopropyl-1-oxoisoindolin-5-yl)benzyl)-5-methyloxazolid in-2-one (Example 5a) 24.1 mg (36%); $^1$H NMR (400 MHz, CDCl$_3$) δ 7.88 (d, 1H) 7.66 (d, 1H) 7.59 (m, 3H) 7.38 (d, 2H) 4.64 (m, 1H) 4.51-4.41 (m, 2H) 4.37 (s, 2H) 3.54 (m, 1H) 3.03 (m, 1H) 2.97 (m, 1H) 1.43 (d, 3H) 0.95-0.89 (m, 4H) m/z (M+H) 363.2.

The following compounds were prepared in a similar way replacing one or more of 5B1, 5F1 and 1A5 with equivalent reagents:

| Ex. | Structure | Name | M/S |
| --- | --- | --- | --- |
| 5b | 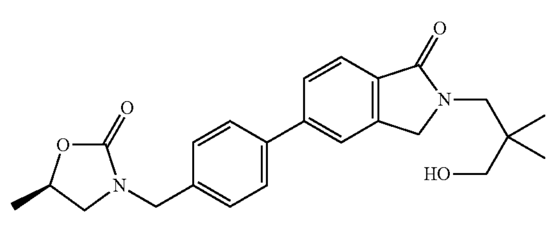 [SMILES: C[C@@H]1CN(Cc2ccc(-c3ccc4c(c3)CN(CC(C)(C)CO)C4=O)cc2)C(=O)O1] | (R)-3-(4-(2-(3-hydroxy-2,2-dimethylpropyl)-1-oxoisoindolin-5-yl)benzyl)-5-methyloxazolidin-2-one | 409.2 |

| Ex. | Structure | Name | M/S |
|---|---|---|---|
| 5c | 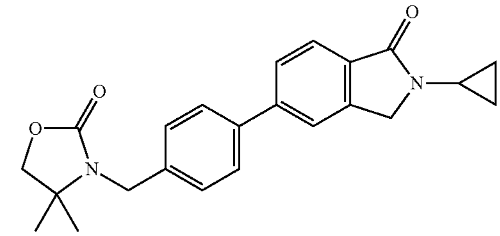 [SMILES: CC1(C)COC(=O)N1Cc1ccc(-c2ccc3c(c2)CN(C2CC2)C3=O)cc1] | 3-(4-(2-cyclopropyl-1-oxoisoindolin-5-yl)benzyl)-4,4-dimethyloxazolidin-2-one | 377.2 |
| 5d | 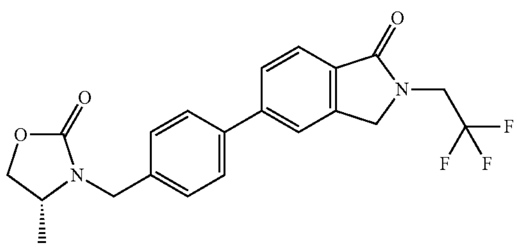 [SMILES: C[C@@H]1COC(=O)N1Cc1ccc(-c2ccc3c(c2)CN(CC(F)(F)F)C3=O)cc1] | (R)-3-(4-(1-oxo-2-(2,2,2-trifluoroethyl)isoindolin-5-yl)benzyl)-4-methyloxazolidin-2-one | 405.0 |
| 5e | 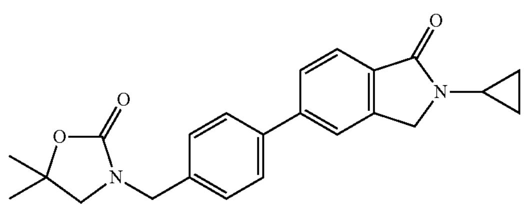 [SMILES: CC1(C)CN(Cc2ccc(-c3ccc4c(c3)CN(C3CC3)C4=O)cc2)C(=O)O1] | 3-(4-(2-cyclopropyl-1-oxoisoindolin-5-yl)benzyl)-5,5-dimethyloxazolidin-2-one | 377.2 |
Example 6a
(R)-1-(1-(4-(2-Cyclopropyl-1-oxoisoindolin-5-yl)phenyl)ethyl)-3-ethylimidazolidine-2,4-dione
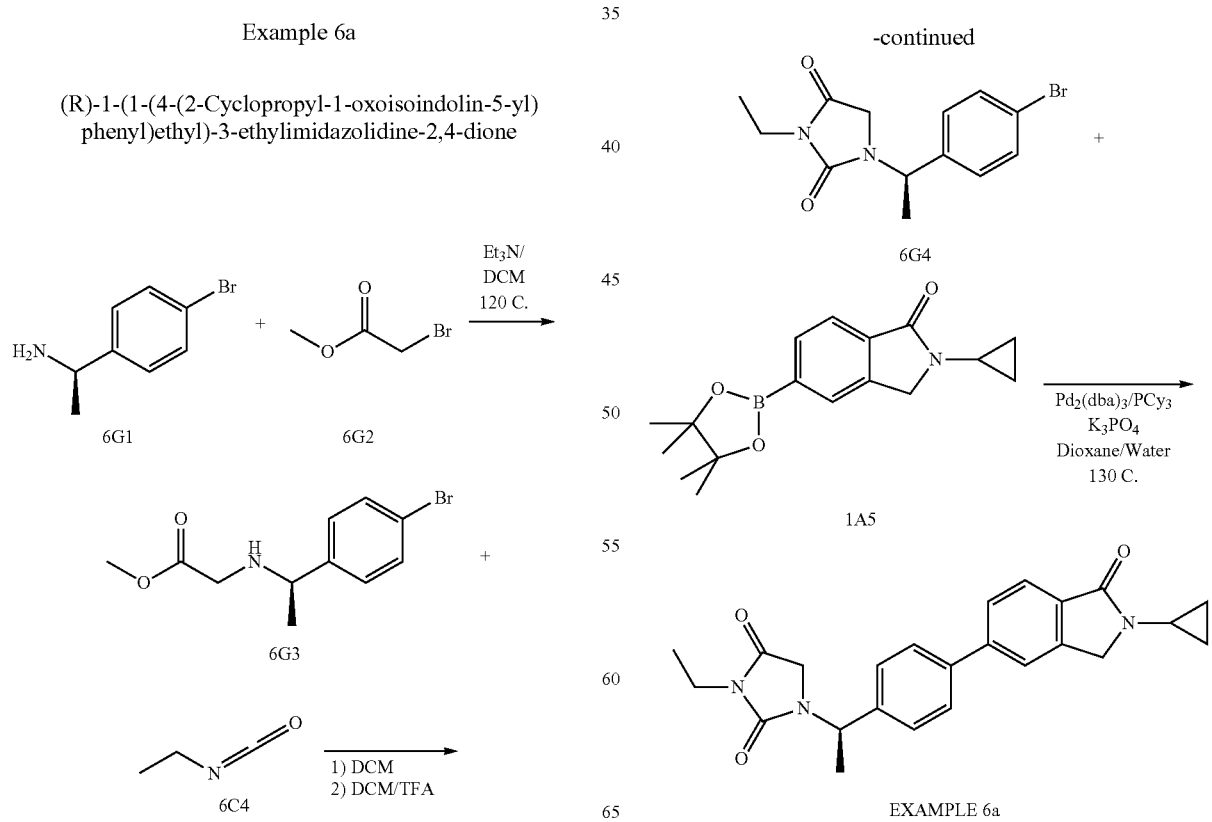

(R)-Methyl 2-(1-(4-bromophenyl)ethylamino)acetate (6G3)

(R)-1-(4-Bromophenyl)ethanamine (6G1) (2.10 mmol, 419 mg), methyl 2-bromoacetate (6G2) (2.10 mmol, 320 mg) and triethylamine (4.19 mmol, 424 mg) were dissolved in DCM (3 ml) and heated in the microwave at 120° C. for 20 min. The crude mixture was concentrated before purification on silica eluting with 20% EtOAc/heptane to give (R)-methyl 2-(1-(4-bromophenyl)ethylamino)acetate (6G3) 230 mg (40.1%); $^1$H NMR (400 MHz, CDCl$_3$) δ 7.44 (d, 2H) 7.20 (d, 2H) 3.77 (q, 1H) 3.69 (s, 3H) 3.4-3.18 (dd, 2H) 1.34 (d, 3H)

(R)-1-(1-(4-Bromophenyl)ethyl)-3-ethylimidazolidine-2,4-dione (6G4)

(R)-Methyl 2-(1-(4-bromophenyl)ethylamino)acetate (6G3) (0.845 mmol, 230 mg) was dissolved in DCM (10 ml) and ethyl isocyanate (6C4) (1.690 mmol, 120 mg) added. The mixture was stirred at room temperature for 3 hours, then concentrated and re-dissolved in DCM (5 ml) and trifluoroacetic acid (0.845 mmol, 96 mg) added. Stirring was continued for 1 h and the reaction diluted with DCM (15 ml) and water (20 ml) and the organic phase separated using a hydrophobic fritted tube. Concentration afforded (R)-1-(1-(4-bromophenyl)ethyl)-3-ethylimidazolidine-2,4-dione (6G4) which was used without further purification; $^1$H NMR (400 MHz, CDCl$_3$) δ 7.50 (d, 2H) 7.18 (d, 2H) 5.43 (q, 1H) 3.76 (d, 1H) 3.56 (q, 2H) 3.46 (d, 1H) 1.57 (d, 3H) 1.22 (t, 3H).

(R)-1-(1-(4-(2-Cyclopropyl-1-oxoisoindolin-5-yl)phenyl)ethyl)-3-ethylimidazolidine-2,4-dione

Example 6a 2-cyclopropyl-5-(4,4,5,5-tetramethyl-1,3,2-dioxaborolan-2-yl)isoindolin-1-one (1A5) (0.096 mmol, 28.8 mg), (R)-1-(1-(4-bromophenypethyl)-3-ethylimidazolidine-2,4-dione (6G4) (0.096 mmol, 30.0 mg), tris(dibenzylidineacetone)dipalladium (0.0048 mmol, 4.41 mg), tricyclohexylphosphine (0.012 mmol, 3.24 mg) and potassium phosphate (0.288 mmol, 61 mg) were suspended in dioxane (2 ml) and water (1 ml) and heated to 130° C. in the microwave for 15 min. The crude mixture was diluted with DCM (3 ml) and water (2 ml) and the phases mixed and separated using a hydrophobic fritted tube. Concentration of the organic layer followed by purification on basic HPLC gave (R)-1-(1-(4-(2-cyclopropyl-1-oxoisoindolin-5-yl)phenypethyl)-3-ethylimidazolidine-2,4-dione (Example 6a) 20.4 mg (52.7%); $^1$H NMR (400 MHz, CDCl$_3$) δ 7.99 (d, 1H) 7.65-7.58 (m, 4H) 7.40 (d, 2H) 5.54 (q, 1H) 4.38 (s, 2H) 3.82 (d, 1H) 3.62-3.52 (m, 3H) 2.97 (m, 1H) 1.65 (d, 3H) 1.24 (t, 3H) 0.96-0.87 (m, 4H) LCMS m/z (M+H) 404.2.

The following compounds were prepared in a similar way replacing one or more of 6G1, 6G2, 6C4 or 1A5 with equivalent reagents:

| Ex. | Structure | Name | M/S |
|---|---|---|---|
| 6b | 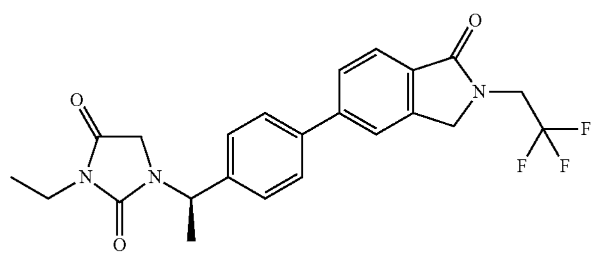 [SMILES: CCN1C(=O)CN([C@H](C)c2ccc(-c3ccc4c(c3)CN(CC(F)(F)F)C4=O)cc2)C1=O] | (R)-3-ethyl-1-(1-(4-(1-oxo-2-(2,2,2-trifluoroethyl)isoindolin-5-yl)phenyl)ethyl)imidazolidine-2,4-dione | 446.2 |
| 6c | 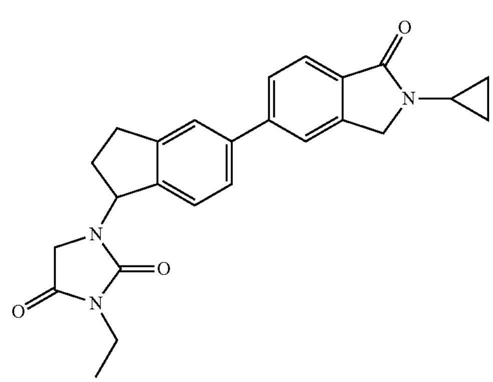 [SMILES: CCN1C(=O)CN(C2CCc3cc(-c4ccc5c(c4)CN(C4CC4)C5=O)ccc32)C1=O] | 1-(5-(2-cyclopropyl-1-oxoisoindolin-5-yl)-2,3-dihydro-1H-inden-1-yl)-3-ethylimidazolidine-2,4-dione | 416.2 |

-continued

| Ex. | Structure | Name | M/S |
|---|---|---|---|
| 6d | 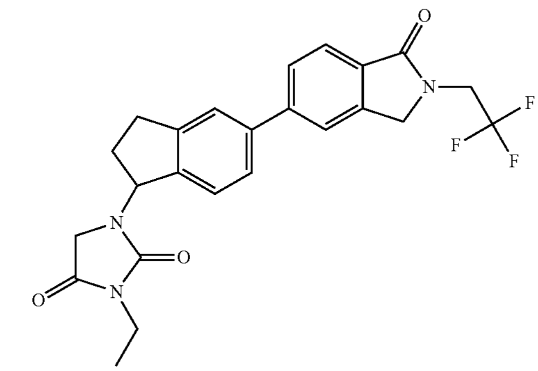 [SMILES: CCN1C(=O)CN(C2CCc3cc(-c4ccc5c(c4)CN(CC(F)(F)F)C5=O)ccc32)C1=O] | 3-ethyl-1-(5-(1-oxo-2-(2,2,2-trifluoroethyl)isoindolin-5-yl)-2,3-dihydro-1H-inden-1-yl)imidazolidine-2,4-dione | 458.0 |
| 6e | 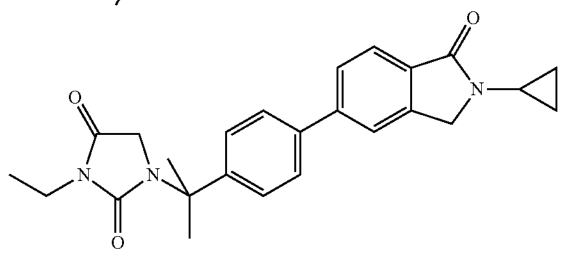 | 1-(2-(4-(2-cyclopropyl-1-oxoisoindolin-5-yl)phenyl)propan-2-yl)-3-ethylimidazolidine-2,4-dione | 418.2 |
| 6f | 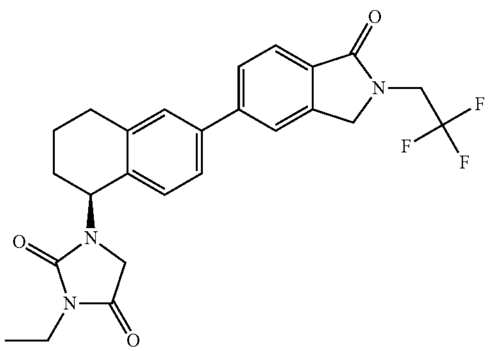 [SMILES: CCN1C(=O)CN([C@H]2CCCc3cc(-c4ccc5c(c4)CN(CC(F)(F)F)C5=O)ccc32)C1=O] | (S)-3-ethyl-1-(6-(1-oxo-2-(2,2,2-trifluoroethyl)isoindolin-5-yl)-1,2,3,4-tetrahydronaphthalen-1-yl)imidazolidine-2,4-dione | 472.2 |

Example 7a

3-Cyclopropyl-1-(4-(2-cyclopropyl-1-oxoisoindolin-5-yl)benzyl)imidazolidine-2,4-dione

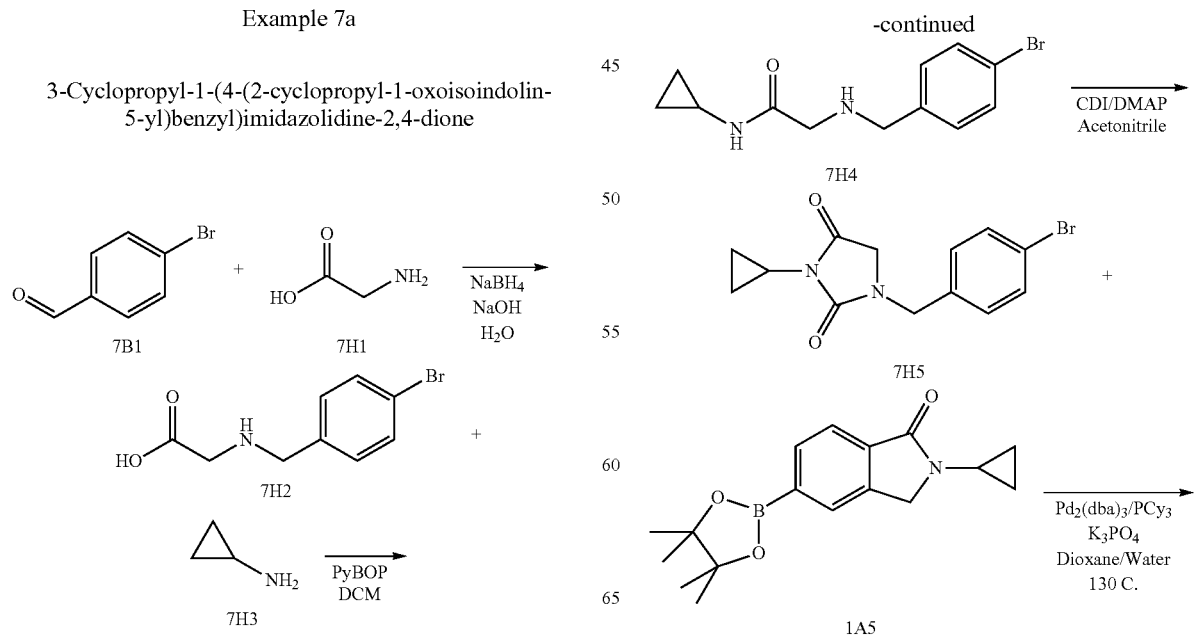

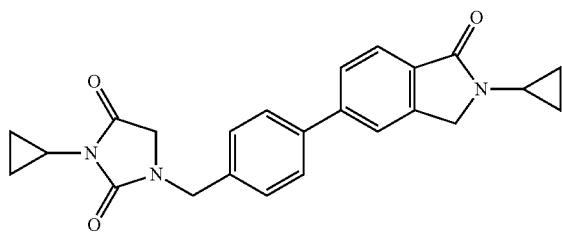

Example 7a

2-(4-Bromobenzylamino)acetic acid (7H2)

To water (40 ml) was added glycine (246 mmol, 18.5 g) and aqueous sodium hydroxide (10M; 100 mmol, 10 ml). 4-Bromobenzaldehyde (130 mmol, 24 g) was added to afford a suspension. Ethanol (40 ml) and THF (90 ml) were added, followed by sodium borohydride (174 mmol, 6.6 g) and the mixture stirred at room temperature overnight. The reaction mixture was concentrated and washed with ether (×3) and the aqueous layer acidified to pH ~6.5 at which point precipitation occurred. The solid was filtered and washed with water and diethyl ether before co-evaporation with toluene to give 2-(4-bromobenzylamino)acetic acid (7H2) 11.3 g; $^1$H NMR (400 MHz, DMSO$_{d6}$) δ 7.56 (d, 2H) 7.38 (d, 2H) 3.85 (s, 2H) 3.10 (s, 2H).

2-(4-Bromobenzylamino)-N-cyclopropylacetamide (7H4)

To a suspension of 2-(4-bromobenzylamino)acetic acid (7H2) (109 mmol, 26.5 g) in dichloromethane (300 ml) was added triethylamine (326 mmol, 33.0 g), cyclopropylamine (7H3) (163 mmol, 9.30 g) and PyBOP (109 mmol, 56.5 g). The suspension was stirred at room temperature overnight before concentration and purification on silica eluting with EtOAc/MeOH 1:0 to 9:1 to give 2-(4-bromobenzylamino)-N-cyclopropylacetamide (7H4) 9.38 g (30.3%); $^1$H NMR (400 MHz, MeOD$_{d4}$) 7.57 (d, 2H) 7.34 (d, 2H) 4.13 (m, 2H) 3.63 (s, 2H) 2.68 (m 1H) 0.76 (m, 2H) 0.56 (m, 2H).

1-(4-Bromobenzyl)-3-cyclopropylimidazolidine-2,4-dione (7H5)

To a solution of 2-(4-bromobenzylamino)-N-cyclopropylacetamide (7H4) (28.3 mmol, 8.0 g) in acetonitrile (200 ml) was added carbonyldiimidazole (56.5 mmol, 9.16 g) and 4-dimethylaminopyridine (56.5 mmol, 6.90 g). The reaction mixture was heated to 60° C. and stirred overnight before cooling to room temperature. Saturated sodium bicarbonate solution was added and the mixture extracted with EtOAc (×3). The combined organic layers were washed with brine, dried over MgSO$_4$, filtered and concentrated and the residue purified on silica eluting with heptane/acetone 9:1 to 7:3 to give 1-(4-bromobenzyl)-3-cyclopropylimidazolidine-2,4-dione (7H5) 8.3 g (98%); $^1$H NMR (400 MHz, CDCl$_3$) δ 7.50 (d, 2H) 7.13 (d, 2H) 4.50 (s, 2H) 3.66 (s, 2H) 2.62 (m, 1H) 0.97 (d, 4H).

3-Cyclopropyl-1-(4-(2-cyclopropyl-1-oxoisoindolin-5-yl)benzyl)imidazolidine-2,4-dione

Example 7a 1-(4-bromobenzyl)-3-cyclopropylimidazolidine-2,4-dione (7H5) (0.1 mmol, 30 mg), 2-cyclopropyl-5-(4,4,5,5-tetramethyl-1,3,2-dioxaborolan-2-yl)isoindolin-1-one (1A5) (0.1 mmol, 31.0 mg), tris(dibenzylidineacetone)dipalladium (0.005 mmol, 4.59 mg), tricyclohexylphosphine (0.012 mmol, 3.37 mg) and potassium phosphate (0.17 mmol, 36.1 mg) were suspended in dioxane (1 ml) and water (0.5 ml) and heated to 130° C. in the microwave for 15 min. The reaction mixture was quenched with 2 ml of water and 3 ml of DCM and the organic phase separated using a hydrophobic fritted tube. The organic phase was concentrated and the residue purified by prep basic HPLC to give 3-cyclopropyl-1-(4-(2-cyclopropyl-1-oxoisoindolin-5-yl)benzyl)imidazolidine-2,4-dione (Example 7a) 21.3 mg (53%); $^1$H NMR (400 MHz, CDCl$_3$) δ 7.88 (d, 1H) 7.63 (d, 1H) 7.58 (m, 3H) 7.35 (d, 2H) 4.59 (s, 2H) 4.37 (s, 2H) 3.71 (s, 2H) 2.96 (m, 1H) 2.64 (m, 1H) 1.01-0.86 (m, 8H) LCMS m/z (M+H) 402.2.

The following compounds were prepared in a similar way replacing one or more of 7B1, 7H1, 7H3 and 1A5 with equivalent reagents:

| Ex. | Structure | Name | M/S |
|---|---|---|---|
| 7b | 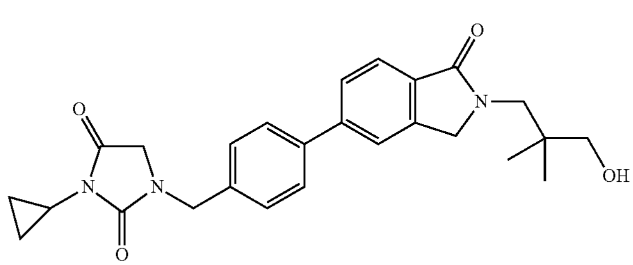 [SMILES: CC(C)(CO)CN1Cc2cc(-c3ccc(CN4CC(=O)N(C5CC5)C4=O)cc3)ccc2C1=O] | 3-cyclopropyl-1-(4-(2-(3-hydroxy-2,2-dimethylpropyl)-1-oxoisoindolin-5-yl)benzyl)imidazolidine-2,4-dione | 448.2 |

| Ex. | Structure | Name | M/S |
|---|---|---|---|
| 7c | 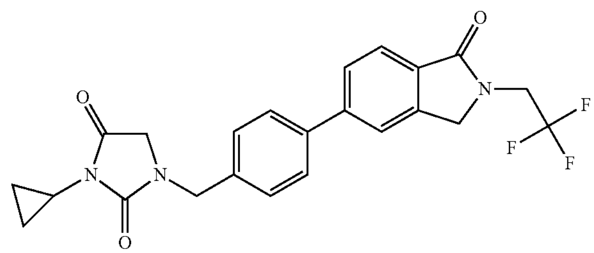 [SMILES: O=C1c2ccc(-c3ccc(CN4CC(=O)N(C5CC5)C4=O)cc3)cc2CN1CC(F)(F)F] | 3-cyclopropyl-1-(4-(1-oxo-2-(2,2,2-trifluoroethyl)isoindolin-5-yl)benzyl)imidazolidine-2,4-dione | 444.0 |

Example 8a 1-(4-(2-Cyclopropyl-1-oxoisoindolin-5-yl)benzyl)-3,5,5-trimethylimidazolidine-2,4-dione

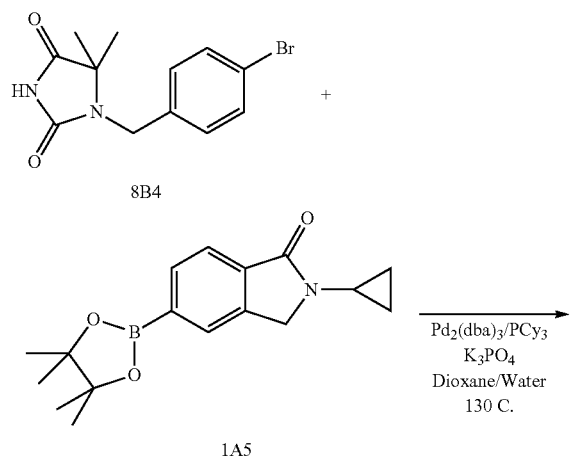

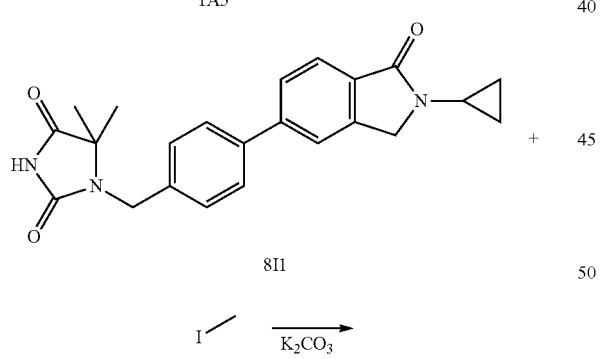

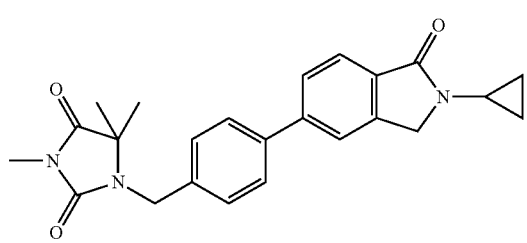

Example 8a

1-(4-(2-Cyclopropyl-1-oxoisoindolin-5-yl)benzyl)-5,5-dimethylimidazolidine-2,4-dione (8I1)

1-(4-bromobenzyl)-5,5-dimethylimidazolidine-2,4-dione (8B4) (0.168 mmol, 50 mg) (prepared according to the method described for intermediate (1B4), 2-cyclopropyl-5-(4,4,5,5-tetramethyl-1,3,2-dioxaborolan-2-yl)isoindolin-1-one (1A5) (0.1 mmol, 53.0 mg), tris(dibenzylidineacetone)dipalladium (0.008 mmol, 8.1 mg), tricyclohexylphosphine (0.02 mmol, 5.7 mg) and potassium phosphate (0.27 mmol, 60.7 mg) were suspended in dioxane (3 ml) and water (1 ml) and heated to 130° C. in the microwave for 15 min. The reaction mixture was quenched with water (6 ml) and DCM (9 ml) and the organic layer separated using a hydrophobic fritted tube. The organic phase was concentrated and the residue purified on silica eluting with 0-100% EtOAc/heptane to give 1-(4-(2-cyclopropyl-1-oxoisoindolin-5-yl)benzyl)-5,5-dimethylimidazolidine-2,4-dione (8I1) 21.3 mg (53%); $^1$H NMR (400 MHz, CDCl$_3$) δ 7.88 (d, 1H) 7.54 (d, 1H) 7.57 (m, 3H) 7.43 (d, 2H) 7.33 (bs, 1H) 4.56 (s, 2H) 4.37 (s, 2H) 3.94 (m, 1H) 1.34 (s, 6H) 0.95-0.88 (m, 4H).

1-(4-(2-Cyclopropyl-1-oxoisoindolin-5-yl)benzyl)-3,5,5-trimethylimidazolidine-2,4-dione

Example 8a 1-(4-(2-cyclopropyl-1-oxoisoindolin-5-yl)benzyl)-5,5-dimethylimidazolidine-2,4-dione (8I1) (0.082 mmol, 32 mg), potassium carbonate (0.246 mmol, 34.1 mg) and iodomethane (8I2) (0.164 mmol, 10.23 μl, 23.32 mg) were dissolved in DMF (822 μl) and stirred under nitrogen at 50° C. overnight. The mixture was partitioned between water and DCM and the organic phase collected using a hydrophobic fritted tube and concentrated under reduced pressure. The crude material that was purified by acidic HPLC to give 1-(4-(2-cyclopropyl-1-oxoisoindolin-5-yl)benzyl)-3,5,5-trimethylimidazolidine-2,4-dione (Example 8a) 13.3 mg (40.1%); $^1$H NMR (400 MHz, CDCl$_3$) δ 7.88 (d, 1H) 7.64 (d, 1H) 7.57 (m, 3H) 7.43 (d, 2H) 4.59 (s, 2H) 4.37 (s, 2H) 3.09 (s, 3H) 2.95 (m, 1H) 1.31 (s, 6H) 0.95-0.87 (m, 4H) LCMS m/z (M+H) 404.2.

The following compounds were prepared in a similar way replacing one or more of 8B4, 1A5 and 8I2 with equivalent reagents:

| Ex. | Structure | Name | M/S |
|---|---|---|---|
| 8b | 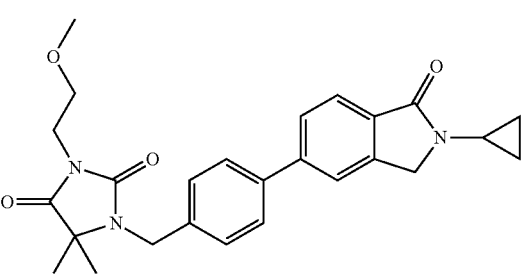 [SMILES: COCCN1C(=O)N(Cc2ccc(-c3ccc4c(c3)CN(C3CC3)C4=O)cc2)C(C)(C)C1=O] | 1-(4-(2-cyclopropyl-1-oxoisoindolin-5-yl)benzyl)-3-(2-methoxyethyl)-5,5-dimethylimidazolidine-2,4-dione | 448.2 |
| 8c | 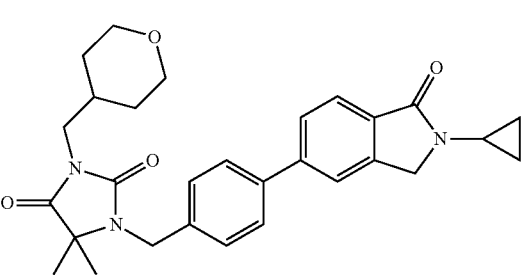 [SMILES: CC1(C)C(=O)N(CC2CCOCC2)C(=O)N1Cc1ccc(-c2ccc3c(c2)CN(C2CC2)C3=O)cc1] | 1-(4-(2-cyclopropyl-1-oxoisoindolin-5-yl)benzyl)-5,5-dimethyl-3-((tetrahydro-2H-pyran-4-yl)methyl)imidazolidine-2,4-dione | 488.2 |
| 8d | 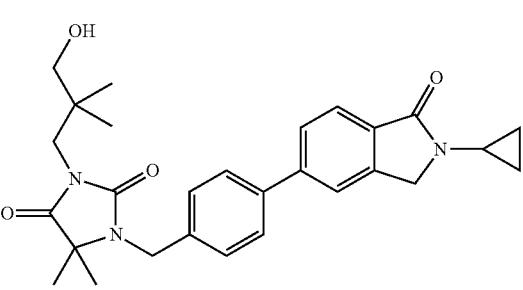 [SMILES: CC(C)(CO)CN1C(=O)N(Cc2ccc(-c3ccc4c(c3)CN(C3CC3)C4=O)cc2)C(C)(C)C1=O] | 1-(4-(2-cyclopropyl-1-oxoisoindolin-5-yl)benzyl)-3-(3-hydroxy-2,2-dimethylpropyl)-5,5-dimethylimidazolidine-2,4-dione | 476.2 |
| 8e | 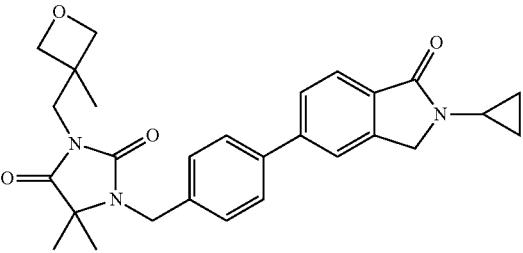 [SMILES: CC1(CN2C(=O)N(Cc3ccc(-c4ccc5c(c4)CN(C4CC4)C5=O)cc3)C(C)(C)C2=O)COC1] | 1-(4-(2-cyclopropyl-1-oxoisoindolin-5-yl)benzyl)-5,5-dimethyl-3-((3-methyloxetan-3-yl)methyl)imidazolidine-2,4-dione | 474.2 |
| 8f | 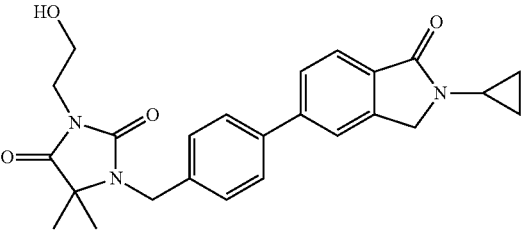 [SMILES: CC1(C)C(=O)N(CCO)C(=O)N1Cc1ccc(-c2ccc3c(c2)CN(C2CC2)C3=O)cc1] | 1-(4-(2-cyclopropyl-1-oxoisoindolin-5-yl)benzyl)-3-(2-hydroxyethyl)-5,5-dimethylimidazolidine-2,4-dione | 434.0 |

Example 9a 1-((5-(2-Cyclopropyl-1-oxoisoindolin-5-yl)pyridin-2-yl)methyl)-3-methylimidazolidine-2,4-dione

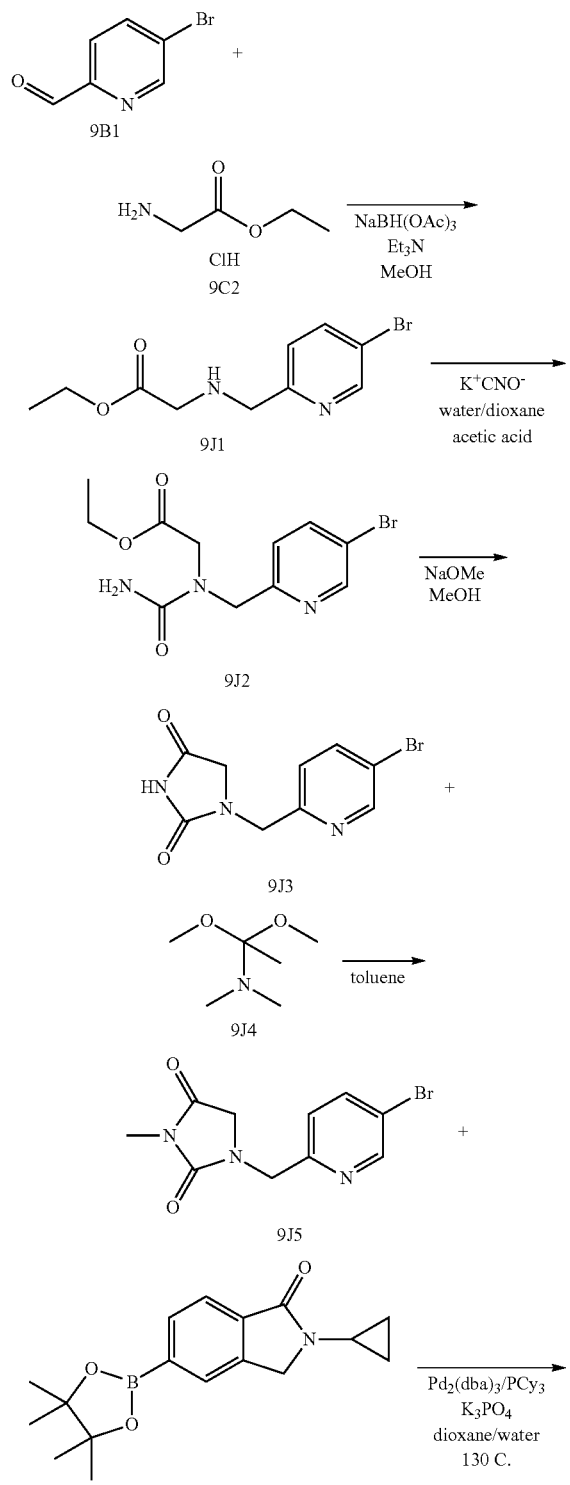

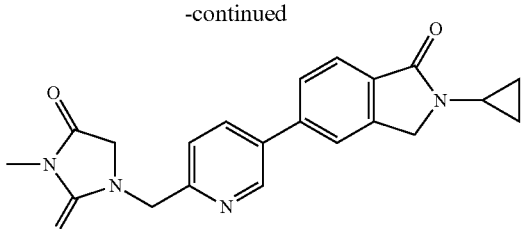

Example 9a

Ethyl 2((5-bromopyridin-2-yl)methylamino)acetate (9J1)

Glycine ethyl ester hydrochloride (9C2) (161 mmol, 22.51 g) was dried under vacuum then dissolved in methanol (200 ml). Triethylamine (137 mmol, 13.87 g) was added with stirring and the resulting solution was added dropwise to a solution of 5-bromo-2-formylpyridine (9B1) (81 mmol, 15 g) in methanol (200 ml) under nitrogen. After 30 min, sodium triacetoxyborohydride (194 mmol, 41.0 g) was added portionwise over 30 min and the reaction was then stirred at room temperature under nitrogen overnight. The reaction was quenched with saturated sodium bicarbonate solution and extracted three times with DCM. The combined organic layers were washed with water, brine and dried using a hydrophobic frit, then concentrated under reduced pressure. The reside was purified on silica eluting with heptane/EtOAc/EtOH 8/1.6/0.4 to 5/4/1 to give ethyl 2-((5-bromopyridin-2-yl)methylamino)acetate (9J1) 11.4 g (51.6%); $^1$H NMR (400 MHz, CDCl$_3$) 8.61 (s, 1H) 7.78 (d, 1H) 7.27 (d, 1H) 4.20 (q, 2H) 3.91 (s, 2H) 3.46 (s, 2H) 2.31 (bs, 1H) 1.27 (t, 3H).

Ethyl 2-(1((5-bromopyridin-2-yl)methyl)ureido)acetate (9J2)

Ethyl 2-((5-bromopyridin-2-yl)methylamino)acetate (9J1) (41.6 mmol, 11.37 g) was dissolved in dioxane (80 ml) and water (80 ml) and potassium cyanate (62.4 mmol, 5.07 g) added. After 10 min, acetic acid (133 mmol, 8.00 g) was added and the reaction mixture stirred at room temperature under nitrogen overnight. The reaction mixture was quenched with saturated sodium bicarbonate (to pH 8-9) and then extracted with dichloromethane (3×). The organic layers were combined, washed with water, brine and dried using a hydrophobic frit, then concentrated under reduced pressure to give ethyl 2-(1-((5-bromopyridin-2-yl)methyl)ureido)acetate (9J2) 11.08 g (84%) which was used without further purification. $^1$H NMR (400 MHz, CDCl$_3$) 8.61 (d, 1H) 7.84 (dd 1H) 7.39 (d, 1H) 5.35 (bs, 2H) 4.51 (s, 2H) 4.17 (q, 2H) 4.11 (s, 2H) 1.25 (t, 3H)

1-((5-Bromopyridin-2-yl)methyl)imidazolidine-2,4-dione (9J3)

2-(1-((5-Bromopyridin-2-yl)methyl)ureido)acetate (9J2) (35.0 mmol, 11.08 g) was dissolved in dry methanol (150 ml), and sodium methoxide (70.1 mmol, 3.79 g) added and the solution stirred at room temperature for 3 hours. The reaction was quenched with water and acidified with saturated ammonium chloride solution to ~pH 7. The mixture was extracted with DCM (3×) and the combined organics washed with brine and dried over sodium sulphate, filtered and concentrated to afford a crude product which was purified on silica eluting with Heptane/EtOAc/EtOH 5/4/1 to give 1-((5-bromopyridin-2-yl)methyl)imidazolidine-2,4-dione. (9J3) 6.12 g (64%); $^1$H NMR (400 MHz, CDCl$_3$) 8.68 (bs, 1H) 8.63 (d, 1H) 7.86 (dd, 1H) 7.22 (d, 1H) 4.61 (s, 2H) 4.04 (s, 2H).

1-((5-Bromopyridin-2-yl)methyl)-3-methylimidazolidine-2,4-dione (9J5)

1-((5-bromopyridin-2-yl)methyl)imidazolidine-2,4-dione (9J3) (0.926 mmol, 250 mg) was mixed with toluene (2.5 ml) and N,N-dimethylacetamide dimethyl acetal (9J4) (3.70 mmol, 490 mg) and heated in the microwave at 150° C. for 15 minutes. The volatile components were removed under high vacuum and the resulting oil purified on silica eluting with 0-100% ethyl acetate/heptane to afford 1-((5-bromopyridin-2-yl)methyl)-3-methylimidazolidine-2,4-dione (9J5) 220 mg (84%); $^1$H NMR (400 MHz, CDCl$_3$) 8.62 (d, 1H) 7.81 (dd, 1H) 7.20 (d, 1H) 4.63 (s, 2H) 3.98 (s, 2H) 3.05 (s, 3H).

1-((5-(2-Cyclopropyl-1-oxoisoindolin-5-yl)pyridin-2-yl)methyl)-3-methylimidazolidine-2,4-dione Example 9a 1-((5-Bromopyridin-2-yl)methyl)-3-methylimidazolidine-2,4-dione (9J5) (0.229 mmol, 65 mg), 2-cyclopropyl-5-(4,4,5,5-tetramethyl-1,3,2-dioxaborolan-2-yl)isoindolin-1-one (1A5) (0.229 mmol, 68.0 mg), tris(dibenzylideneacetone)dipalladium (0.011 mmol, 10.5 mg), tricyclohexylphosphine (0.027 mMol, 7.7 mg) and potassium phosphate (0.389 mmol, 83.0 mg) were suspended in dioxane (1 ml) and water (0.5 ml) and heated to 130° C. in the microwave for 15 min. The reaction mixture was quenched with 2 ml of water and 3 ml of DCM and then passed through a hydrophobic fritted tube, washing with DCM. The organic layers were concentrated and the residue purified by basic prep HPLC to give 1-((5-(2-cyclopropyl-1-oxoisoindolin-5-yl)pyridin-2-yl)methyl)-3-methylimidazolidine-2,4-dione (Example 9a) 27.6 mg (32.1%); $^1$H NMR (400 MHz, CDCl$_3$) 8.79 (dd, 1H) 7.91 (m, 2H) 7.64 (dd, 1H) 7.59 (s, 1H) 7.39 (d, 1H) 4.75 (s, 2H) 4.40 (s, 2H) 4.04 (s, 2H) 3.07 (s, 3H) 2.97 (m, 1H) 0.97-0.88 (m, 4H) LCMS m/z (M+H) 377.2.

The following compounds were prepared in a similar way replacing one or more of 9B1, 9C2, 9J4 and 1A5 with equivalent reagents:

| Ex. | Structure | Name | M/S |
|-----|-----------|------|-----|
| 9b  | 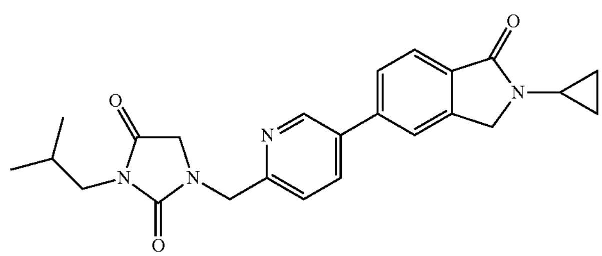 [SMILES: CC(C)CN1C(=O)CN(Cc2ccc(-c3ccc4c(c3)CN(C3CC3)C4=O)cn2)C1=O]          | 1-((5-(2-cyclopropyl-1-oxoisoindolin-5-yl)pyridin-2-yl)methyl)-3-isobutylimidazolidine-2,4-dione | 419.2 |
| 9c  | 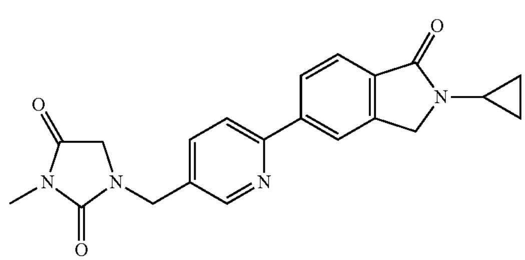 [SMILES: CN1C(=O)CN(Cc2ccc(-c3ccc4c(c3)CN(C3CC3)C4=O)nc2)C1=O]          | 1-((6-(2-cyclopropyl-1-oxoisoindolin-5-yl)pyridin-3-yl)methyl)-3-methylimidazolidine-2,4-dione | 377.2 |
| 9d  | 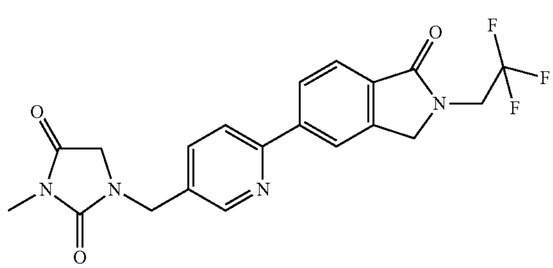 [SMILES: CN1C(=O)CN(Cc2ccc(-c3ccc4c(c3)CN(CC(F)(F)F)C4=O)nc2)C1=O]          | 3-methyl-1-((6-(1-oxo-2-(2,2,2-trifluoroethyl)isoindolin-5-yl)pyridin-3-yl)methyl)imidazolidine-2,4-dione | 419.0 |

Example 10a

2-Isopropyl-6-(4-((3-methyl-2,4-dioxoimidazolidin-1-yl)methyl)phenyl)-3-oxoisoindoline-4-carbonitrile

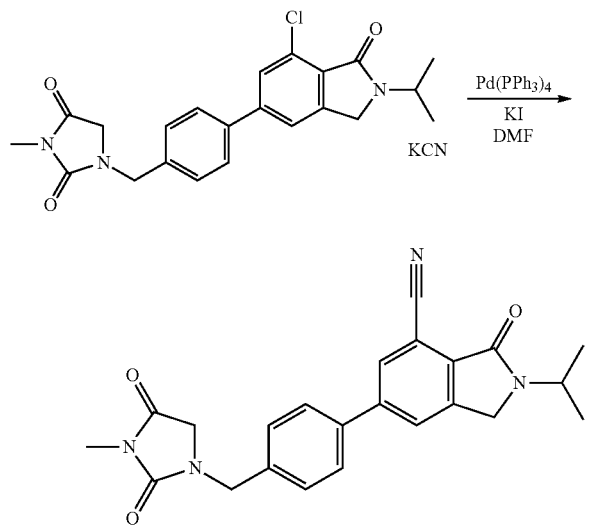

1-(4-(7-chloro-2-isopropyl-1-oxoisoindolin-5-yl)benzyl)-3-methylimidazolidine-2,4-dione (0.049 mmol, 20 mg), tetrakis(triphenylphosphine)palladium(0) (0.015 mmol, 16.83 mg), potassium iodide (0.073 mmol, 12.09 mg) and potassium cyanide (0.073 mmol, 4.74 mg) were mixed in dimethylformamide (1 ml) and heated at 150° C. in the microwave for 20 min. TLC (100% EtOAc) showed mainly starting material with a minor slightly slower running spot. A further 20 mg of tetrakis(triphenylphosphine)palladium(0) and 20 mg of potassium cyanide were added and the reaction mixture was microwaved at 200° C. for 30 mins. TLC showed no starting material remaining.

The reaction mixture was quenched with water and extracted with EtOAc. The combined organics were passed through a celite pad and then concentrated. The crude product was purified by basic prep HPLC to afford 2-isopropyl-6-(4-((3-methyl-2,4-dioxoimidazolidin-1-yl)methyl)phenyl)-3-oxoisoindoline-4-carbonitrile (1.4 mg, 7%); $^1$H NMR (400 MHz, CDCl$_3$) 7.93 (s, 1H), 7.83 (s, 1H), 7.58 (d, 2H), 7.41 (d, 2H), 4.71 (m, 1H), 4.65 (s, 2H), 4.44 (s, 2H), 3.80 (s, 2H), 3.08 (s, 3H), 1.34 (d, 6H). LCMS m/z (M+H) 403.2.

Example 11a 1-(4-(2-Cyclopropyl-1-oxoisoindolin-5-yl)-3-methylbenzyl)-3-methyl imidazolidine-2,4-dione

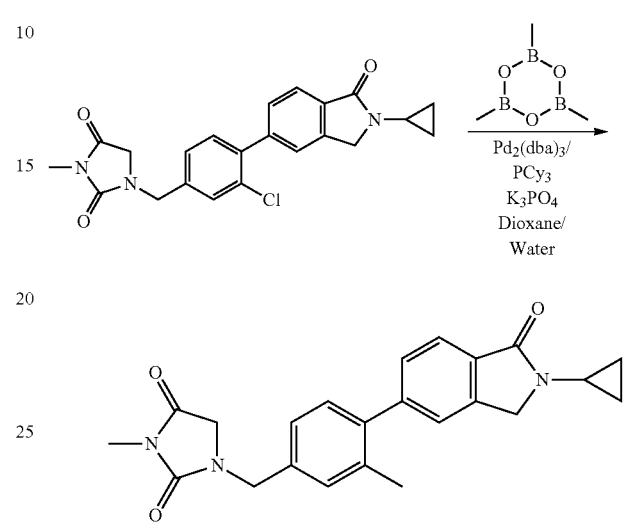

1-(3-chloro-4-(2-cyclopropyl-1-oxoisoindolin-5-yl)benzyl)-3-methylimidazolidine-2,4-dione (0.073 mmol, 30 mg), trimethylboroxine (0.110 mmol, 27.6 mg), tris(dibenzylideneacetone)dipalladium(0) (3.66 μmol, 3.4 mg), tricyclohexylphosphine (8.78 μmol, 2.5 mg) and potassium phosphate, tribasic (0.124 mmol, 26.4 mg) were suspended in dioxane (750 μL) and water (250 μL) and heated under microwave irradiation at 130° C. for 30 minutes. The solvent was removed under reduced pressure and the mixture partitioned between water and dichloromethane. The organic layer was separated using a hydrophobic frit and concentrated. Purified by acidic prep HPLC to afford 1-(4-(2-cyclopropyl-1-oxoisoindolin-5-yl)-3-methylbenzyl)-3-methylimidazolidine-2,4-dione (11.2 mg, 39%); 1H NMR (400 MHz, CDCl$_3$) 7.86 (d, 1H), 7.36 (dd, 1H), 7.31 (d, 1H), 7.21-7.12 (m, 3H), 4.58 (s, 2H), 4.36 (s, 2H), 3.79 (s, 2H), 3.07 (s, 3H), 2.96 (m, 1H), 2.24 (s, 3H), 0.97-0.87 (m, 4H). LCMS (M+H) 390.2.

The following compounds were prepared in a similar way using equivalent reagents:

| Ex. | Structure | Name | M/S |
|---|---|---|---|
| 11b | (structure shown) | 1-(4-(2-cyclopropyl-1-oxoisoindolin-5-yl)-2-methylbenzyl)-3-methylimidazolidine-2,4-dione | 390.2 |

| Ex. | Structure | Name | M/S |
|---|---|---|---|
| 11c | 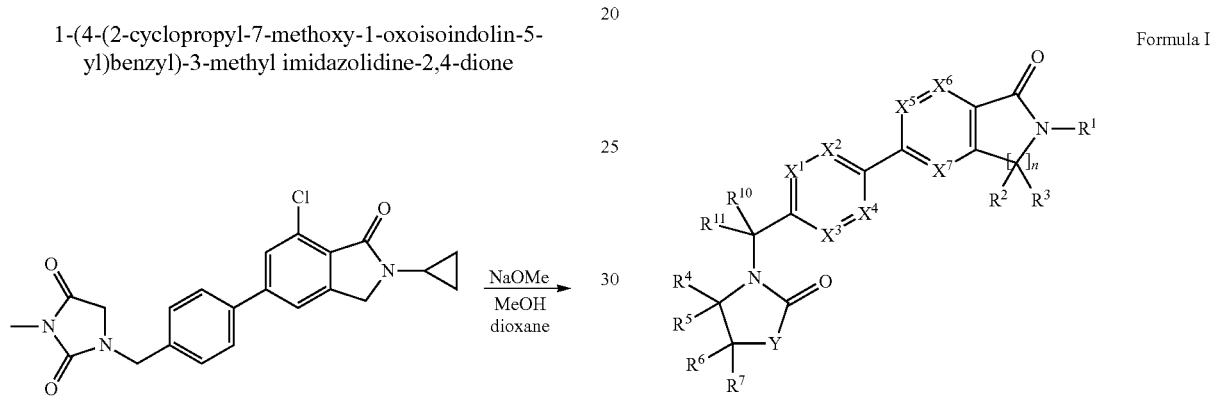 | 1-(4-(2-cyclopropyl-7-methyl-1-oxoisoindolin-5-yl)benzyl)-3-methylimidazolidine-2,4-dione | 390.2 |

Example 12a 1-(4-(2-cyclopropyl-7-methoxy-1-oxoisoindolin-5-yl)benzyl)-3-methyl imidazolidine-2,4-dione

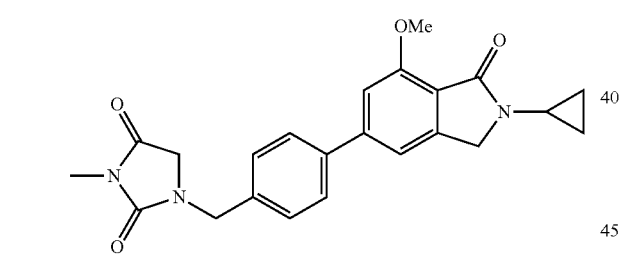

1-(4-(7-chloro-2-cyclopropyl-1-oxoisoindolin-5-yl)benzyl)-3-methylimidazolidine-2,4-dione (0.122 mmol, 50 mg) was placed in a microwave vial, which was then capped. Dry dioxane (2 ml) was added and the vial purged with argon. Sodium methoxide (25 wt. % in methanol, 0.52 mmol, 120 µL) was then added and the mixture was heated under microwave irradiation at 100° C. for 10 mins.

The mixture was quenched with water and the products extracted with dichloromethane and filtered through a hydrophobic frit. The combined organics were dried and purified by basic prep HPLC to afford 1-(4-(2-cyclopropyl-7-methoxy-1-oxoisoindolin-5-yl)benzyl)-3-methyl imidazolidine-2,4-dione as a white solid (5.4 mg, 11%); 1H NMR (400 MHz, CDCl$_3$) 7.58 (d, 2H), 7.35 (d, 2H), 7.12 (s, 1H), 7.02 (s, 1H), 4.62 (s, 2H), 4.30 (s, 2H), 4.01 (s, 3H), 3.78 (s, 2H), 3.07 (s, 3H), 2.89 (m, 1H), 0.93-0.83 (m, 4H). LCMS (M+H) 406.2.

The invention claimed is:

1. A heterocyclic derivative of formula I

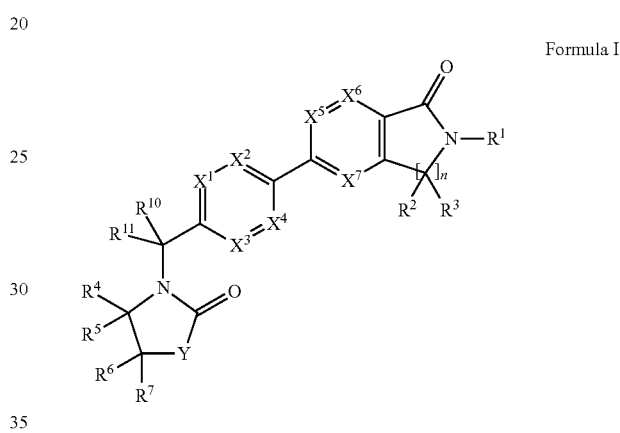

Formula I wherein

R$^1$ is C$_{1-4}$alkyl, C$_{0-4}$alkylC$_{3-8}$cycloalkyl, or C$_{0-4}$alkylZ$^1$, said C$_{1-4}$alkyl and C$_{0-4}$alkylC$_{3-8}$cycloalkyl being optionally substituted with one or more substituent independently selected from hydroxy, C$_{1-4}$alkyl, C$_{1-4}$alkyloxy, CN and halogen;

Z$^1$ is a 4-7 membered saturated ring containing a heteroatom selected from O, S and SO$_2$;

n is 1 or 2;

each R$^2$ and R$^3$ is independently H or C$_{1-4}$alkyl;

Y is O or NR$^8$;

R$^4$, R$^5$, R$^6$ and R$^7$ are independently H or C$_{1-4}$alkyl; or when Y is NR$^8$, either R$^4$ and R$^5$, or R$^6$ and R$^7$, may together represent oxo;

R$^8$ is C$_{1-4}$alkyl, C$_{0-4}$alkylC$_{3-8}$cycloalkyl, or C$_{0-4}$alkylZ$^2$, said C$_{1-4}$alkyl and C$_{0-4}$alkylC$_{3-8}$cycloalkyl being optionally substituted with one or more substituent independently selected from hydroxy, C$_{1-4}$alkyl, C$_{1-4}$alkyloxy, oxo, CN and halogen;

Z$^2$ is a 4-7 membered saturated ring containing a heteroatom selected from O, S and SO$_2$;

X$^1$-X$^7$ are CR$^9$; or one of X$^1$-X$^7$ may be N;

each R$^9$ is independently selected from H, C$_{1-4}$alkyl, C$_{1-4}$alkyloxy, nitrile and halogen, said C$_{1-4}$alkyl and C$_{1-4}$alkyloxy being optionally substituted with one or more substituent independently selected from hydroxy and halogen;

R$^{10}$ and R$^{11}$ are independently H or C$_{1-4}$alkyl; or, when R$^{10}$ is alkyl and X$^1$ is CR$^9$, R$^{10}$ and R$^9$ together with the atoms to which they are bonded may form a fused ring optionally comprising a heteroatomic moiety selected from O, S and SO$_2$;

or a pharmaceutically acceptable salt thereof.

2. The heterocyclic derivative according to claim 1 or a pharmaceutically acceptable salt thereof, wherein $R^1$ is $C_{1-4}$alkyl or $C_{3-8}$cycloalkyl.

3. The heterocyclic derivative according to claim 1 or a pharmaceutically acceptable salt thereof, wherein n is 1.

4. The heterocyclic derivative according to claim 1 or a pharmaceutically acceptable salt thereof, wherein each $R^2$ and $R^3$ is H.

5. The heterocyclic derivative according to claim 1 or a pharmaceutically acceptable salt thereof, wherein $R^4$ and $R^5$ are independently H or $C_{1-4}$alkyl.

6. The heterocyclic derivative according to claim 5 or a pharmaceutically acceptable salt thereof, wherein Y is $NR^8$ and $R^6$ and $R^7$ together represent oxo.

7. The heterocyclic derivative according to claim 6 or a pharmaceutically acceptable salt thereof, wherein $R^8$ is $C_{1-4}$alkyl or $C_{3-8}$cycloalkyl.

8. The heterocyclic derivative according to claim 1 or a pharmaceutically acceptable salt thereof, wherein $X^1$-$X^7$ are $CR^9$ and each $R^9$ is independently selected from H, $C_{1-4}$alkyl, $C_{1-4}$alkyloxy, nitrile and halogen, said $C_{1-4}$alkyl or $C_{1-4}$alkyloxy groups being optionally substituted with one or more halogen.

9. The heterocyclic derivative according to claim 1 or a pharmaceutically acceptable salt thereof, wherein $R^{10}$ and $R^{11}$ are H.

10. A heterocyclic derivative according to claim 1 selected from:
- 1-(4-(2-cyclopropyl-1-oxoisoindolin-5-yl)benzyl)-3-methylimidazolidine-2,4-dione;
- 1-(2-chloro-4-(2-cyclopropyl-1-oxoisoindolin-5-yl)benzyl)-3-ethylimidazolidine-2,4-dione;
- 1-(4-(2-cyclopropyl-1-oxoisoindolin-5-yl)benzyl)-3-ethyl-5,5-dimethylimidazolidine-2,4-dione;
- 1-(4-(7-chloro-2-(3-hydroxy-2,2-dimethylpropyl)-1-oxoisoindolin-5-yl)benzyl)-3-ethylimidazolidine-2,4-dione;
- 3-ethyl-1-(4-(1-oxo-2-(2,2,2-trifluoroethyl)isoindolin-5-yl)benzyl)imidazolidine-2,4-dione;
- 3-(4-(2-cyclopropyl-1-oxoisoindolin-5-yl)benzyl)-1-methylimidazolidine-2,4-dione;
- 2-cyclopropyl-5-(4-((3-methyl-2-oxoimidazolidin-1-yl)methyl)phenyl)isoindolin-1-one;
- 1-(2-chloro-4-(2-cyclopropyl-1-oxoisoindolin-5-yl)benzyl)-3-methylimidazolidine-2,4-dione;
- 1-(2-chloro-4-(1-oxo-2-(2,2,2-trifluoroethyl)isoindolin-5-yl)benzyl)-3-methylimidazolidine-2,4-dione;
- 1-(2-chloro-4-(2-(3-hydroxy-2,2-dimethylpropyl)-1-oxoisoindolin-5-yl)benzyl)-3-methylimidazolidine-2,4-dione;
- 1-(2-chloro-4-(2-cyclopropyl-1-oxoisoindolin-5-yl)benzyl)-3,5,5-trimethylimidazolidine-2,4-dione;
- 1-(2-chloro-4-(1-oxo-2-(2,2,2-trifluoroethyl)isoindolin-5-yl)benzyl)-3,5,5-trimethylimidazolidine-2,4-dione;
- 1-(3-chloro-4-(2-cyclopropyl-1-oxoisoindolin-5-yl)benzyl)-3-methylimidazolidine-2,4-dione;
- 1-(3-chloro-4-(2-(3-hydroxy-2,2-dimethylpropyl)-1-oxoisoindolin-5-yl)benzyl)-3-methylimidazolidine-2,4-dione;
- 3,5,5-trimethyl-1-(4-(1-oxo-2-(2,2,2-trifluoroethyl)isoindolin-5-yl)benzyl)imidazolidine-2,4-dione;
- 1-(3-chloro-4-(2-cyclopropyl-1-oxoisoindolin-5-yl)benzyl)-3,5,5-trimethylimidazolidine-2,4-dione;
- 1-(3-chloro-4-(1-oxo-2-(2,2,2-trifluoroethyl)isoindolin-5-yl)benzyl)-3,5,5-trimethylimidazolidine-2,4-dione;
- 1-(4-(2-(3-hydroxy-2,2-dimethylpropyl)-1-oxoisoindolin-5-yl)benzyl)-3,5,5-trimethylimidazolidine-2,4-dione;
- 1-(4-(2-isopropyl-1-oxoisoindolin-5-yl)benzyl)-3-methylimidazolidine-2,4-dione;
- 1-(4-(2-cyclobutyl-1-oxoisoindolin-5-yl)benzyl)-3,5,5-trimethylimidazolidine-2,4-dione;
- 1-(4-(2-isobutyl-1-oxoisoindolin-5-yl)benzyl)-3,5,5-trimethylimidazolidine-2,4-dione;
- 1-(4-(2-cyclopropyl-1-oxoisoindolin-5-yl)benzyl)-3-ethylimidazolidine-2,4-dione;
- 3-methyl-1-(4-(1-oxo-2-(2,2,2-trifluoroethyl)isoindolin-5-yl)benzyl)imidazolidine-2,4-dione;
- 1-(4-(7-chloro-1-oxo-2-(2,2,2-trifluoroethyl)isoindolin-5-yl)benzyl)-3-methylimidazolidine-2,4-dione;
- 1-(4-(7-chloro-2-cyclopropyl-1-oxoisoindolin-5-yl)benzyl)-3-methylimidazolidine-2,4-dione;
- 3-ethyl-1-(4-(2-methyl-1-oxoisoindolin-5-yl)benzyl)imidazolidine-2,4-dione;
- 3-ethyl-1-(4-(2-isopropyl-1-oxoisoindolin-5-yl)benzyl)imidazolidine-2,4-dione;
- 3-ethyl-5,5-dimethyl-1-(4-(2-methyl-1-oxoisoindolin-5-yl)benzyl)imidazolidine-2,4-dione;
- 3-ethyl-1-(4-(2-ethyl-1-oxoisoindolin-5-yl)benzyl)-5,5-dimethylimidazolidine-2,4-dione;
- 3-ethyl-5,5-dimethyl-1-(4-(1-oxo-2-propylisoindolin-5-yl)benzyl)imidazolidine-2,4-dione;
- 3-ethyl-1-(4-(2-isopropyl-1-oxoisoindolin-5-yl)benzyl)-5,5-dimethylimidazolidine-2,4-dione;
- 1-(4-(2-ethyl-1-oxoisoindolin-5-yl)benzyl)-3-methylimidazolidine-2,4-dione;
- 3-methyl-1-(4-(1-oxo-2-propylisoindolin-5-yl)benzyl)imidazolidine-2,4-dione;
- 3-ethyl-1-(4-(2-ethyl-1-oxoisoindolin-5-yl)benzyl)imidazolidine-2,4-dione;
- 3-ethyl-1-(4-(1-oxo-2-propylisoindolin-5-yl)benzyl)imidazolidine-2,4-dione;
- 1-(4-(2-cyclobutyl-1-oxoisoindolin-5-yl)benzyl)-3-ethylimidazolidine-2,4-dione;
- 1-(4-(2-cyclobutyl-1-oxoisoindolin-5-yl)benzyl)-3-methylimidazolidine-2,4-dione;
- 1-(4-(2-isobutyl-1-oxoisoindolin-5-yl)benzyl)-3-methylimidazolidine-2,4-dione;
- 1-(4-(2-(cyclopropylmethyl)-1-oxoisoindolin-5-yl)benzyl)-3-ethylimidazolidine-2,4-dione;
- 1-(4-(2-(cyclopropylmethyl)-1-oxoisoindolin-5-yl)benzyl)-3-ethyl-5,5-dimethylimidazolidine-2,4-dione;
- 1-(4-(2-(cyclopropylmethyl)-1-oxoisoindolin-5-yl)benzyl)-3-methylimidazolidine-2,4-dione;
- 3,5,5-trimethyl-1-(4-(2-methyl-1-oxoisoindolin-5-yl)benzyl)imidazolidine-2,4-dione;
- 1-(4-(2-ethyl-1-oxoisoindolin-5-yl)benzyl)-3,5,5-trimethylimidazolidine-2,4-dione;
- 3,5,5-trimethyl-1-(4-(1-oxo-2-propylisoindolin-5-yl)benzyl)imidazolidine-2,4-dione;
- 1-(4-(2-isopropyl-1-oxoisoindolin-5-yl)benzyl)-3,5,5-trimethylimidazolidine-2,4-dione;
- 1-(4-(2-(cyclopropylmethyl)-1-oxoisoindolin-5-yl)benzyl)-3,5,5-trimethylimidazolidine-2,4-dione;
- 3,5,5-trimethyl-1-(4-(1-oxo-2-propyl-1,2,3,4-tetrahydroisoquinolin-6-yl)benzyl)imidazolidine-2,4-dione;
- 1-(4-(2-isopropyl-1-oxo-1,2,3,4-tetrahydroisoquinolin-6-yl)benzyl)-3,5,5-trimethylimidazolidine-2,4-dione;
- (R)-3-(4-(2-cyclopropyl-1-oxoisoindolin-5-yl)benzyl)-5-methyloxazolidin-2-one;
- (R)-3-(4-(2-(3-hydroxy-2,2-dimethylpropyl)-1-oxoisoindolin-5-yl)benzyl)-5-methyloxazolidin-2-one;

(R) -1-(1-(4-(2-cyclopropyl-1-oxoisoindolin-5-yl)phenyl)ethyl)-3-ethylimidazolidine-2,4-dione;

(R)-3-ethyl-1-(1-(4-(1-oxo-2-(2,2,2-trifluoroethyl)isoindolin-5-yl)phenyl)ethyl)imidazolidine-2,4-dione;

1-(5-(2-cyclopropyl-1-oxoisoindolin-5-yl)-2,3-dihydro-1H-inden-1-yl)-3-ethylimidazolidine-2,4-dione;

3-ethyl-1-(5-(1-oxo-2-(2,2,2-trifluoroethyl)isoindolin-5-yl)-2,3-dihydro-1H-inden-1-yl)imidazolidine-2,4-dione;

3-cyclopropyl- 1-(4-(2-cyclopropyl-1-oxoisoindolin-5-yl)benzyl)imidazolidine-2,4-dione;

3-cyclopropyl- 1-(4-(2-(3-hydroxy-2,2-dimethylpropyl)-1-oxoisoindolin-5-yl)benzyl)imidazolidine-2,4-dione;

3-cyclopropyl-1-(4-(1-oxo-2-(2,2,2-rifluoroethyl)isoindolin-5-yl)benzyl)imidazolidine-2,4-dione;

1-(4-(2-cyclopropyl-1-oxoisoindolin-5-yl)benzyl)-3,5,5-trimethylimidazolidine-2,4-dione;

1-((5-(2-cyclopropyl-1-oxoisoindolin-5-yl)pyridin-2-yl)methyl)-3-methylimidazolidine-2,4-dione;

1-((5-(2-cyclopropyl-1-oxoisoindolin-5-yl)pyridin-2-yl)methyl)-3-isobutylimidazolidine-2,4-dione;

1-((6-(2-cyclopropyl-1-oxoisoindolin-5-yl)pyridin-3-yl)methyl)-3 -methylimidazolidine-2,4-dione;

3-methyl-1-((6-(1-oxo-2-(2,2,2-trifluoroethyl)isoindolin-5-yl)pyridin-3-yl)methyl)imidazolidine-2,4-dione;

or a pharmaceutically acceptable salt thereof.

11. A method for treating schizophrenia or generalised anxiety disorder, the method comprising administering to a subject in need thereof a therapeutically effective amount of a compound according to claim 1 or a pharmaceutically acceptable salt thereof.

12. A pharmaceutical composition comprising a heterocyclic derivative according to claim 1 or a pharmaceutically acceptable salt thereof in admixture with one or more pharmaceutically acceptable excipient.

* * * * *